(12) United States Patent
Fadli et al.

(10) Patent No.: US 7,582,123 B2
(45) Date of Patent: Sep. 1, 2009

(54) COLORING COMPOSITION COMPRISING AT LEAST ONE AZOMETHINE COMPOUND WITH A PYRAZOLINONE UNIT

(75) Inventors: Aziz Fadli, Chelles (FR); Eric Metais, St Leu la Forêt (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 12/213,441

(22) Filed: Jun. 19, 2008

(65) Prior Publication Data
US 2009/0044348 A1 Feb. 19, 2009

Related U.S. Application Data

(60) Provisional application No. 60/929,600, filed on Jul. 5, 2007.

(30) Foreign Application Priority Data
Jun. 22, 2007 (FR) ................... 07 55968

(51) Int. Cl.
*A61Q 5/10* (2006.01)
*C07D 231/44* (2006.01)
(52) U.S. Cl. ............. 8/405; 8/406; 8/435; 8/565; 8/568; 8/570; 548/367.7
(58) Field of Classification Search ............ 8/405, 8/406, 435, 565, 568, 570, 573; 548/367.7
See application file for complete search history.

(56) References Cited

U.S. PATENT DOCUMENTS

| | | | |
|---|---|---|---|
| 2,194,201 A | 3/1940 | Eisenstaedt | |
| 3,617,167 A | 11/1971 | Berth et al. | |
| 4,003,699 A | 1/1977 | Rose et al. | |
| RE30,199 E | 1/1980 | Rose et al. | |
| 4,295,853 A | 10/1981 | Kasahara et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,596,025 A * | 1/1997 | Oxman et al. ............... | 523/109 |
| 5,663,366 A | 9/1997 | Neunhoeffer et al. | |
| 5,708,151 A | 1/1998 | Mockli | |
| 5,766,576 A | 6/1998 | Lowe et al. | |
| 5,792,221 A | 8/1998 | Lagrange et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,022,143 B2 | 4/2006 | Vidal et al. | |
| 7,030,121 B2 | 4/2006 | Akahane et al. | |
| 7,060,110 B2 | 6/2006 | Vidal et al. | |
| 7,077,873 B2 | 7/2006 | David et al. | |
| 7,261,743 B2 | 8/2007 | Plos et al. | |
| 7,285,137 B2 | 10/2007 | Vidal et al. | |
| 7,288,124 B2 | 10/2007 | Fadli | |
| 7,329,288 B2 | 2/2008 | Sabelle et al. | |
| 2002/0095732 A1 | 7/2002 | Kravtchenko et al. | |
| 2003/0084516 A9 | 5/2003 | Kravtchenko et al. | |
| 2008/0071092 A1 | 3/2008 | Vidal et al. | |

FOREIGN PATENT DOCUMENTS

DE 23 59 399 6/1975

(Continued)

OTHER PUBLICATIONS

STIC Search Report dated Jan. 6, 2009.*

(Continued)

*Primary Examiner*—Eisa B Elhilo
(74) *Attorney, Agent, or Firm*—Finnegan, Henderson, Farabow, Garrett & Dunner LLP

(57) ABSTRACT

The present disclosure relates to a composition for coloring keratin fibers which comprises, in an appropriate dyeing medium, at least one compound chosen from leuco compounds of formula (I), azomethine dyes with a pyrazolinone unit of formula (II), their mesomeric forms, acid addition salts and solvates thereof:

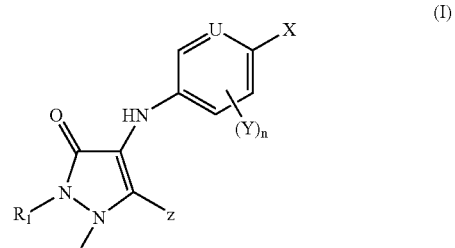

(I)

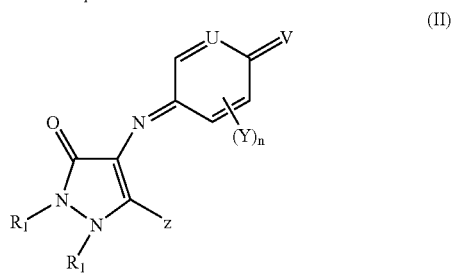

(II)

and dyeing methods and multicompartment devices for use thereof.

22 Claims, No Drawings

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 A1 | 5/1997 |
| EP | 0 714 954 B1 | 6/1996 |
| EP | 0 770 375 B1 | 5/1997 |
| EP | 1 250 909 B1 | 10/2002 |
| EP | 1 550 656 A1 | 7/2005 |
| EP | 1 568 694 A1 | 8/2005 |
| EP | 1 764 082 A2 | 3/2007 |
| EP | 1 634 574 B1 | 5/2008 |
| FR | 1 488 169 | 7/1967 |
| FR | 2 413 660 | 7/1979 |
| FR | 2 586 913 | 3/1987 |
| FR | 2 692 572 | 12/1993 |
| FR | 2 733 749 | 11/1996 |
| FR | 2 750 048 | 12/1997 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 1 026 978 | 4/1966 |
| GB | 1 153 196 | 5/1969 |
| JP | 56-39072 | 4/1981 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/078660 A1 | 10/2002 |
| WO | WO 02/100369 A2 | 12/2002 |
| WO | WO 02/100864 A1 | 12/2002 |

OTHER PUBLICATIONS

Eisenstaedt, E. "The Condensation of Aminoanyipyrine with Aromatic Amines in the Presence of Oxidizing Agents," The Journal of Organic Chemistry, 3: 153-163 (1938).

English Language Abstract for EP 0 770 375. (1997).

English Language Abstract for EP 1 250 909. (2002).

English Language Abstract for JP 20-19576. (1990).

English Language Abstract for JP 2526099. (1996).

English Language Abstract for JP 56-39072. (1981).

English Language Abstract for the journal article by Rubtsov, MV "Synthesis of derivatives of naphthoquinone for the treatment of tuberculosis." Zhumal Obshchei Khimii, 16: 221-234 (1946).

English Language Abstract for the journal article by Elguero, J. et al. "Structure of the 4-phenylazo-5- pyrazolones," Bulletin De La Societe Chimique De France, 9: 2990-2995 (1966).

English Language Abstract for the journal article by Galal, EE et al. "Preliminary Study of the Anti-Inflammatory and Anti-Spasmodic Effects of 4-Anisylidino(Aminoantipyrine)," Journal of Drug Research, 7(1): 53-63 (1975).

English Language Abstract for the journal article by Kallmayer HJ et al. "The Emerson Reaction by Salbutamol," Scientia Pharmaceutica, 72(1): 1-13 (2004).

English Language Translation for journal article by Svobodova et al., Substance Identification Listing, Citation No. 2802977, Collection of Czechoslovak Chemical Communications, 35(1): 31-44 (1970).

English Language Abstract for journal article by Svobodova et al. "Color reaction of phenols with 4-aminoantipyrine," Collection of Czechoslovak Chemical Communications, 35(1): 31-44 (1970).

English Language Translation for journal article by Kawamura et al., Substance Identification Listing, Citation No. 2802977, Chem. Pharm. Bull. 16(4): 626 (1968).

English Language Translation for journal article by Saito, Y. et al. Substance Identification Listing, Citation No. 5671846, Chem. Pharm. Bull. 35(2): 869-872 (1987).

English Language Translation for journal article by Tang, B. et al. Substance Identification Listing, Citation No. 6393131, Spectrochim. Acta Part A. 58(1-2): 2557-2562 (2002).

English Language Translation for journal article by Meyer, V. Substance Identification Listing, Citation No. 676595, Ann. Chim. (Paris) 10(17): 271, 348, 353 (1932).

European Search Report for EP 08 15 8622 dated Nov. 27, 2008, Examiner D. Frelon.

French Search Report for FR 0755 968 (French priority application for the present application) dated Apr. 7, 2008, Examiner D. Frelon.

Jones, PF et al. "Estimation of Phenols by the 4-Aminoantipyrine Method: Identification of the Colored Reaction Products by Proton Magnetic Resonance Spectroscopy," Can. J. Chem., 51: 2860-2868 (1973).

Kumar, KS et al. "Novel Reactions for the Simple and Sensitive Spectrophotometric Determination of Traces of Selenium in Environmental Samples," Helvetica Chimica Acta, 88: 343-348 (2005).

Stahly, GP "Synthesis of unsymmetrical biphenyls by reaction of nitroarenes with phenols," The Journal of Organic Chemistry, 50(17): 3091-3094 (1985).

\* cited by examiner

COLORING COMPOSITION COMPRISING AT LEAST ONE AZOMETHINE COMPOUND WITH A PYRAZOLINONE UNIT

This application claims benefit of U.S. Provisional Application No. 60/929,600, filed Jul. 5, 2007, the contents of which are incorporated herein by reference. This application also claims benefit of priority under 35 U.S.C. § 119 to French Patent Application No. FR 0755968, filed Jun. 22, 2007, the contents of which are also incorporated herein by reference.

The present disclosure relates to a composition for coloring keratin fibers, for example human keratin fibers, such as the hair, which comprises, in an appropriate dyeing medium, at least one azomethine compound with a pyrazolinone unit.

It is known practice to dye keratin fibers with dyeing compositions comprising direct dyes. These compounds are colored and coloring molecules which have an affinity for the fibers. It is known practice, for example, to use direct dyes of the nitrobenzene type, anthraquinone dyes, nitropyridine dyes, and dyes of azo, xanthene, acridine, azine or triarylmethane type.

It is also known practice to apply these dyes to the fibers, optionally in the presence of an oxidant, if a simultaneous fiber-lightening effect is desired. When the leave-in time has elapsed, the fibers are rinsed, optionally washed and dried.

The colorations which result from the use of direct dyes are often chromatic colorations that are nevertheless temporary or semi-permanent. The nature of the interactions that bond the direct dyes to the keratin fiber and their desorption from the surface and/or from the core of the fiber are responsible for their low tinctorial strength and their relatively poor resistance to washing or to perspiration. These direct dyes, moreover, are generally sensitive to light, since the resistance of the chromophore towards photochemical attack is low, which leads to a fading of the coloring of the hair over time. The sensitivity of these dyes to light depends on their uniform distribution or distribution as aggregates in and/or on the keratin fiber.

In order to obtain the same result, it is likewise possible to use the non-colored reduced form of these dyes and to apply it to the keratin fibers in the presence of an oxidant in order to generate the colored and coloring oxidized form.

The present inventors have discovered, surprisingly, novel direct dyes that do not exhibit the drawbacks of the existing direct dyes.

Thus, one aspect of the present disclosure is direct dyes that make it possible to obtain a coloration in various shades that is strong, chromatic, aesthetic, of low selectivity and highly resistant to the various attacks to which hair may be subjected, such as shampooing, light, sweat and perming, and that is easily erased.

For example, one aspect of the present disclosure is a dyeing composition comprising, in an appropriate dyeing medium, at least one compound chosen from leuco compounds of formula (I), azomethine dyes with a pyrazolinone unit of formula (II), their mesomeric forms, and also their acid addition salts and solvates thereof:

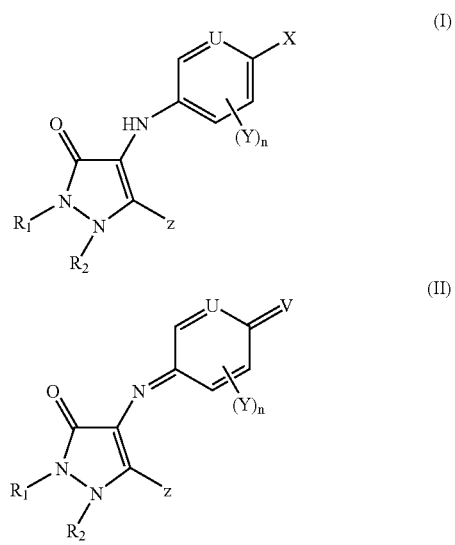

wherein:
n is an integer ranging from 0 to 3;
U is CR or N;
R is chosen from:
a hydrogen atom;
$C_1$-$C_4$ alkyl radicals optionally substituted by a hydroxyl radical;
$C_1$-$C_4$ alkoxy radicals optionally substituted by a hydroxyl radical; and
(di)alkyl($C_1$-$C_4$)amino radicals wherein the alkyl moiety is optionally substituted by a hydroxyl radical;
X is chosen from:
a hydroxyl radical; and
$NR'_1R''_1$ radicals, wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino and (di)alkyl($C_1$-$C_2$)amino radicals; phenyl radicals optionally substituted by at least one radical chosen from hydroxyl, amino and ($C_1$-$C_2$)alkoxy radicals; and when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$) amino, hydroxyl, carboxyl, carboxamido, ($C_1$-$C_2$) alkoxy, and $C_1$-$C_4$ alkyl radicals which are optionally substituted by at least one radical chosen from hydroxyl, amino, (di)alkylamino, alkoxy, carboxyl, and sulfonyl radicals;
when X is $NHR'_1$ and when U is CR wherein R is an alkoxy radical, then X and U may form a 6-membered ring of morpholine type which is optionally substituted by at least one $C_1$-$C_4$ alkyl group;
V is chosen from:
an oxygen atom;
$NR'_1$ radicals wherein $R'_1$ is chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and phenyl radicals optionally substituted by at least one radical chosen from a hydroxyl, amino and ($C_1$-$C_2$)alkoxy radicals; and $N^+R'_1R''_1$ radicals wherein $R'_1$ and $R''_1$ are independently chosen from a hydrogen atom; $C_1$-$C_6$ alkyl radicals optionally substituted by at least one radical chosen from hydroxyl, ($C_1$-$C_2$) alkoxy, amino, and (di)alkyl ($C_1$-$C_2$)amino radicals; and phenyl radicals optionally substituted by at least one radical chosen from hydroxyl, amino, and ($C_1$-$C_2$)alkoxy radicals;

when V is $N^+R'_1R''_1$, the electroneutrality of the structure (II) is ensured by an anion An-;

when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$) amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;

when V is $NR'_1$ and when U is CR wherein R is an alkoxy radical, then V and U may form a 6-membered ring of morpholine type which is optionally substituted by at least one $C_1$-$C_4$ alkyl group;

each instance of Y, which may be identical or different, Y is chosen from:
 a hydroxyl radical;
 $C_1$-$C_4$ alkyl radicals;
 $C_1$-$C_4$ hydroxyalkyl radicals;
 halogen atoms such as chlorine, iodine, fluorine and bromine atoms;
 an oxygen atom substituted by a radical chosen from $C_1$-$C_4$ alkyl, aryl and heteroaryl radicals, it being possible for the $C_1$-$C_4$ alkyl, aryl and heteroaryl radicals to be substituted by at least one hydroxyl radical; and
 $NR'_2R'_3$ radicals, wherein $R'_2$ and $R'_3$, which are identical or different, are chosen from:
  a hydrogen atom;
  $C_1$-$C_4$ alkylcarbonyl radicals optionally substituted by a quaternary ammonium group such as a trialkylammonium or by a cationic or non-cationic nitrogen-containing heterocycle, for example, an imidazole group, a thiazole group, a pyridine group, a piperidine group, a pyrrolidine group, a pyrimidine group, a pyrazine group, an imidazolium group, a pyridinium group, a thiazolium group, a pyrrolidinium group, a piperidinium group, and a pyrimidinium group, wherein these nitrogen-containing heterocycles are optionally substituted by at least one $C_1$-$C_4$ alkyl radical;
  aminocarbonyl radicals;
  $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and
  phenyl radicals optionally substituted by at least one radical chosen from hydroxyl, amino, and ($C_1$-$C_2$) alkoxy radicals;
 $R'_2$ and $R'_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals; and when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, for example a benzene, pyrrole, pyrrolidine, pyrazole, furan, pyrrolidine, morpholine or imidazole ring, optionally substituted by at least one $C_1$-$C_4$ alkyl radical;

Z is chosen from:
 linear and branched $C_1$-$C_4$ alkyl radicals;
 $NR_3R_4$ radicals; and
 $OR_5$ radicals;

$R_1$, $R_2$, $R_3$, $R_4$ and $R_5$, which are identical or different, are chosen from:
 $C_1$-$C_6$ alkyl radicals optionally substituted by at least one radical chosen from $OR_6$ radicals, $NR_7R_8$ radicals, carboxyl radicals, $C_1$-$C_4$ alkyl carboxylate radicals, sulfonic radicals, (di)alkylcarboxamido $CONR_7R_8$ radicals, sulfonamido $SO_2NR_7R_8$ radicals, and 5- or 6-membered heteroaryl and phenyl radicals optionally substituted by at least one radical chosen from ($C_1$-$C_4$) alkyl, hydroxyl, $C_1$-$C_2$ alkoxy, amino, (di)alkyl($C_1$-$C_2$) amino and $C_1$-$C_4$ hydroxyalkyl radicals; phenyl radicals optionally substituted by at least one radical chosen from ($C_1$-$C_4$)alkyl, hydroxy($C_1$-$C_4$)alkyl, hydroxyl, $C_1$-$C_2$ alkoxy, amino, and (di)alkyl($C_1$-$C_2$)amino radicals; and
 5- or 6-membered heteroaryl radicals optionally substituted by at least one radical chosen from ($C_1$-$C_4$)alkyl and ($C_1$-$C_2$)alkoxy radicals;

$R_3$, $R_4$ and $R_5$ may also be chosen from a hydrogen atom;

$R_6$, $R_7$ and $R_8$, which are identical or different, are chosen from a hydrogen atom; linear and branched $C_1$-$C_4$ alkyl radicals optionally substituted by at least one radical chosen from hydroxyl, $C_1$-$C_2$ alkoxy, (di)alkylcarboxamido $CONR_9R_{10}$, sulfonyl $SO_2R_9$, and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals; and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals;

$R_7$ and $R_8$, which are identical or different, may also be chosen from (di)alkylcarboxamido $CONR_9R_{10}$ radicals and sulfonyl $SO_2R_9$ radicals;

$R_9$ and $R_{10}$, which are identical or different, are chosen from a hydrogen atom and linear and branched $C_1$-$C_4$ alkyl radicals optionally substituted by at least one radical chosen from a hydroxyl radical and $C_1$-$C_2$ alkoxy radicals;

$R_1$ and $R_2$, and independently $R_3$ and $R_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl($C_1$-$C_4$)amino, (di)hydroxyalkyl($C_1$-$C_4$) amino, hydroxyl, carboxyl, (di)alkylcarboxamido, ($C_1$-$C_2$) alkoxy, and $C_1$-$C_4$ alkyl radicals optionally substituted by at least one radical chosen from hydroxyl, amino, (di)alkyl($C_1$-$C_4$)amino, $C_1$-$C_2$ alkoxy, carboxyl, and sulfonyl radicals; and An- is an anion or a mixture of anions which allows the electroneutrality of the structures to be ensured;

with the proviso that, when Z is an alkyl radical, $R_1$ is not an optionally substituted phenyl radical and $R_2$ is not an alkyl radical;

with the exception of the following compound:

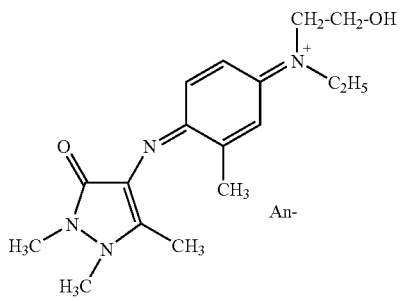

and also its mesomeric forms, its acid addition salts and its solvates thereof.

In another aspect of the present disclosure, the at least one compound in the dyeing composition is chosen from leuco compounds of formula (I), azomethine dyes with a pyrazolinone unit of formula (II), their mesomeric forms, their acid addition salts and their solvates thereof:

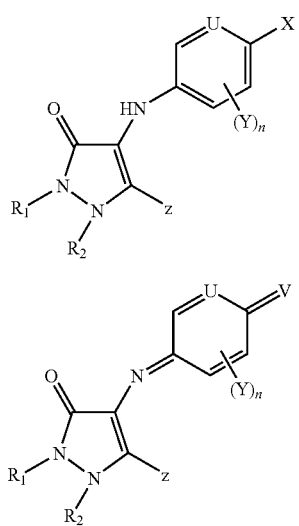

wherein:
n is an integer ranging from 0 to 3;
U is CR or N;
R is chosen from
a hydrogen atom,
$C_1$-$C_4$ alkyl radicals optionally substituted by a hydroxyl radical;
$C_1$-$C_4$ alkoxy radicals optionally substituted by a hydroxyl radical; and
(di)alkyl($C_1$-$C_4$)amino radicals wherein the alkyl moiety is optionally substituted by a hydroxyl radical;
X is chosen from:
a hydroxyl radical;
$NR'_1R''_1$ radicals wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; phenyl radicals optionally substituted by at least one radical chosen from hydroxyl, amino, and ($C_1$-$C_2$)alkoxy radicals; and when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$) amino, hydroxyl, carboxyl, carboxamido, ($C_1$-$C_2$) alkoxy, and $C_1$-$C_4$ alkyl radicals which are optionally substituted by at least one radical chosen from hydroxyl, amino, (di)alkylamino, alkoxy, carboxyl, and sulfonyl radicals;

when X is $NHR'_1$ and when U is CR wherein R is an alkoxy radical, then X and U may form a 6-membered ring of morpholine type which is optionally substituted by at least one $C_1$-$C_4$ alkyl group, V is chosen from:
an oxygen atom;
$NR'_1$ radicals wherein $R'_1$ is chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and phenyl radicals optionally substituted by at least one radical chosen from hydroxyl, amino, and ($C_1$-$C_2$)alkoxy radicals; and $N^+R'_1R''_1$ radicals wherein $R'_1$ and $R''_1$ are independently chosen from a hydrogen atom; $C_1$-$C_6$ alkyl radicals optionally substituted by at least one radical chosen from hydroxyl, ($C_1$-$C_2$) alkoxy, amino, and (di)alkyl ($C_1$-$C_2$)amino radicals; and phenyl radicals optionally substituted by at least one radical chosen from hydroxyl, amino, and ($C_1$-$C_2$)alkoxy radicals;

when V is $N^+R'_1R''_1$, the electroneutrality of the structure (II) is ensured by an anion An-;

when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$) amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;

when V is $NR'_1$ and when U is CR wherein R is an alkoxy radical, then V and U may form a 6-membered ring of morpholine type which is optionally substituted by at least one $C_1$-$C_4$ alkyl group;

each instance of Y, which may be identical or different, Y is chosen from:
a hydroxyl radicals;
$C_1$-$C_4$ alkyl radicals;
$C_1$-$C_4$ hydroxyalkyl radicals;
halogen atoms such as a chlorine, iodine, fluorine and bromine atoms;
an oxygen atom substituted by a radical chosen from $C_1$-$C_4$ alkyl, aryl and heteroaryl radicals, it being possible for the $C_1$-$C_4$ alkyl, aryl and heteroaryl radicals to be substituted by at least one hydroxyl radical; and
$NR'_2R'_3$ radicals;

wherein R'$_2$ and R'$_3$, which are identical or different, are chosen from a hydrogen atom;

C$_1$-C$_4$ alkylcarbonyl radicals optionally substituted by a quaternary ammonium group such as a trialkylammonium or by a cationic or non-cationic nitrogen-containing heterocycle, for example, an imidazole group, a thiazole group, a pyridine group, a piperidine group, a pyrrolidine group, a pyrimidine group, a pyrazine group, an imidazolium group, a pyridinium group, a thiazolium group, a pyrrolidinium group, a piperidinium group, and a pyrimidinium group, wherein these nitrogen-containing heterocycles are optionally substituted by at least one C$_1$-C$_4$ alkyl radical;

aminocarbonyl radicals;

C$_1$-C$_6$ alkyl radicals optionally substituted by at least one radical chosen from hydroxyl, (C$_1$-C$_2$)alkoxy, amino, and (di)alkyl(C$_1$-C$_2$)amino radicals; and phenyl radicals optionally substituted by at least one radical chosen from hydroxyl, amino, and (C$_1$-C$_2$) alkoxy radicals;

R'$_2$ and R'$_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl(C$_1$-C$_4$)amino, hydroxyl, carboxyl, (di)alkylcarboxamido, (C$_1$-C$_2$)alkoxy, and C$_1$-C$_4$ alkyl radicals which are optionally substituted by at least one radical chosen from hydroxyl, amino, (di)alkylamino, alkoxy, carboxyl, and sulfonyl radicals; and when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, for example a benzene, pyrrole, pyrrolidine, pyrazole, furan, pyrrolidine, morpholine or imidazole ring, optionally substituted by at least one C$_1$-C$_4$ alkyl radical;

Z is chosen from:

NR$_3$R$_4$ radicals; and

OR$_5$ radicals;

R$_1$, R$_2$, R$_3$, R$_4$ and R$_5$, which are identical or different, are chosen from:

C$_1$-C$_6$ alkyl radicals optionally substituted by at least one radical chosen from OR$_6$ radicals, NR$_7$R$_8$ radicals, carboxylradicals, C$_1$-C$_4$ alkyl carboxylate radicals, sulfonic radicals, (di)alkylcarboxamido CONR$_7$R$_8$ radicals, sulfonamido SO$_2$NR$_7$R$_8$ radicals, and 5- or 6-membered heteroaryl and phenyl radicals optionally substituted by at least one radical chosen from (C$_1$-C$_4$) alkyl, hydroxyl, C$_1$-C$_2$ alkoxy, amino, (di)alkyl(C$_1$-C$_2$) amino and C$_1$-C$_4$ hydroxyalkyl radicals;

phenyl radicals optionally substituted by at least one radical chosen from (C$_1$-C$_4$)alkyl, hydroxy(C$_1$-C$_4$)alkyl, hydroxyl, C$_1$-C$_2$ alkoxy, amino, and (di)alkyl(C$_1$-C$_2$) amino radicals; and 5- or 6-membered heteroaryl radicals optionally substituted by at least one radical chosen from (C$_1$-C$_4$)alkyl and (C$_1$-C$_2$)alkoxy radicals;

R$_3$, R$_4$ and R$_5$ may also be chosen from a hydrogen atom;

R$_6$, R$_7$ and R$_8$, which are identical or different, are chosen from a hydrogen atom; linear and branched C$_1$-C$_4$ alkyl radicals optionally substituted by at least one radical chosen from hydroxyl, C$_1$-C$_2$ alkoxy, (di)alkylcarboxamido CONR$_9$R$_{10}$, sulfonyl SO$_2$R$_9$, and phenyl radicals optionally substituted by at least one radical chosen from (C$_1$-C$_4$)alkyl, hydroxyl, C$_1$-C$_2$ alkoxy, amino, and (di)alkyl(C$_1$-C$_2$)amino radicals; and phenyl radicals optionally substituted by at least one radical chosen from (C$_1$-C$_4$)alkyl, hydroxyl, C$_1$-C$_2$ alkoxy, amino, and (di)alkyl(C$_1$-C$_2$)amino radicals;

R$_7$ and R$_8$, which are identical or different, may also be chosen from (di)alkylcarboxamido CONR$_9$R$_{10}$ radicals and sulfonyl SO$_2$R$_9$ radicals;

R$_9$ and R$_{10}$, which are identical or different, are chosen—from a hydrogen atom, and linear and branched C$_1$-C$_4$ alkyl radicals optionally substituted by at least one radical chosen from a hydroxyl radical and C$_1$-C$_2$ alkoxy radicals;

R$_1$ and R$_2$, and independently R$_3$ and R$_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl(C$_1$-C$_4$)amino, (di)hydroxyalkyl(C$_1$-C$_4$) amino, hydroxyl, carboxyl, (di)alkylcarboxamido, (C$_1$-C$_2$) alkoxy, and C$_1$-C$_4$ alkyl radicals optionally substituted by at least one radical chosen from hydroxyl, amino, (di)alkyl(C$_1$-C$_4$)amino, C$_1$-C$_2$ alkoxy, carboxyl, and sulfonyl radicals; and An- is an anion or a mixture of anions which allows the electroneutrality of the structures to be ensured.

According to the present disclosure, acid addition salts are salts of physiologically acceptable organic or inorganic acids of the compounds of formula (I) and/or (II).

For example, the acid addition salts which may be used herein may be chosen from hydrochloric acid, hydrobromic acid, sulfuric acid, citric acid, succinic acid, tartaric acid, lactic acid, methanesulfonic acid, para-toluenesulfonic acid, benzenesulfonic acid, phosphoric acid and acetic acid.

The present invention also provides the new compounds selected from the leuco compounds of formula (I), the azomethine dyes with a pyrazolinone unit of formula (II) corresponding to the compounds of formula (I), their mesomeric forms, their addition salts with an acid and their solvates, as defined herein.

Another aspect of the present disclosure relates to the use of leuco compounds of formula (I), azomethine dyes with a pyrazolinone unit of formula (II), their mesomeric forms, their acid addition salts and their solvates thereof, for the coloring of keratinous fibers.

Yet another aspect of the present disclosure relates to a method for the coloring of keratin fibers employing at least one compound chosen from leuco compounds of formula (I), azomethine dyes with a pyrazolinone unit of formula (II), their mesomeric forms, their acid addition salts and their solvates thereof.

Another aspect of the present disclosure relates to a multi-compartment device for the implementation of the method disclosed herein.

The leuco compounds of formula (I), azomethine dyes with a pyrazolinone unit of formula (II), their mesomeric forms, their acid addition salts and their solvates thereof, as disclosed herein, make it possible, for example, to obtain rapid-chromatic colorations that are resistant to the various attacks to which the hair may be subjected, such as shampooing and to light, and which may be obliterated and then rapidly reconstituted.

The leuco compounds of formula (I) are colorless or pale in coloration, and the corresponding azomethine derivatives with a pyrazolinone unit of formula (II) are colored and coloring species. It is possible to modify the structure of the compounds of formula (I) to obtain the compounds of formula (II) by adding at least one oxidant, and conversely, it is possible to modify the structure of the compounds of formula (II) to obtain the compounds of formula (I) by adding at least one reductant. This structural modification may be facilitated by modifying the pH and/or the temperature. The formation of the compounds of formula (I) is therefore favored by an acidic pH and/or a reduction in the temperature; the formation of the compounds of formula (II) is favored by a basic pH and/or an increase in the temperature. Such behavior makes it possible, for instance, to modify the coloration of the keratin fibers with ease.

As disclosed herein, unless indicated otherwise, the end points encompassing a range of values are included in that range.

As disclosed herein, unless indicated otherwise, the alkyl radicals are linear or branched, and an alkoxy radical is a radical alkyl-O—, wherein the alkyl radical is as defined before.

Also as disclosed herein, unless indicated otherwise, (di) alkylamino radical is an amino radical which can be substituted by one or two alkyl radicals, and a (di)alkylcarboxamido radical is a carboxamido radical which may be substituted by one or two alkyl radicals.

According to at least one aspect of the present disclosure, in formula (I), the radicals $R_1$ and $R_2$, which are identical or different, are chosen from:
  $C_1$-$C_4$ alkyl radicals optionally substituted by at least one radical chosen from a hydroxyl radical, ($C_1$-$C_2$)alkoxy radicals, amino radicals, and (di)alkyl($C_1$-$C_2$)amino radicals; and
  phenyl radicals optionally substituted by at least one radical chosen from $C_1$-$C_4$ alkyl radicals and $C_1$-$C_4$ hydroxyalkyl radicals.

In at least one embodiment, the radicals $R_1$ and $R_2$, which are identical or different, are chosen from methyl, ethyl, 2-hydroxyethyl, 3-hydroxypropyl, 2-hydroxypropyl, and phenyl radicals.

In another embodiment, the radicals $R_1$ and $R_2$ are identical and are chosen from methyl, ethyl, and phenyl radicals.

According to another embodiment, the radicals $R_1$ and $R_2$ form, together with the nitrogen atoms to which they are attached, a saturated or unsaturated 5- or 6-membered ring which is optionally substituted.

In yet another embodiment, the radicals $R_1$ and $R_2$ form, together with the nitrogen atoms to which they are attached, a pyrazolidine, pyridazolidine, triazepine ring optionally substituted by at least one radical chosen from $C_1$-$C_4$ alkyl, hydroxyl, ($C_1$-$C_2$)alkoxy, carboxyl, (di)alkylcarboxamido, amino, and (di)alkyl($C_1$-$C_2$)amino radicals.

In yet another embodiment, the radicals $R_1$ and $R_2$ form, together with the nitrogen atoms to which they are attached, a pyrazolidine, pyridazolidine, triazepine ring optionally substituted by a $C_1$-$C_2$ alkyl radical.

According to one aspect of the present disclosure, Z is chosen from:
  linear and branched $C_1$-$C_4$ alkyl radicals; and
  $NR_3R_4$ radicals, wherein $R_3$ and $R_4$ are each independently chosen from a hydrogen atom and $C_1$-$C_4$ alkyl radicals or $R_3$ and $R_4$ form, together with the nitrogen atom to which they are attached, a 5- to 7-membered ring chosen from pyrrolidine, piperidine, and piperazine rings.

According to one embodiment of the present disclosure, Z is chosen from $NR_3R_4$ radicals.

Examples of $R_3$ and $R_4$ radicals, which are identical or different, include, but are not limited to a hydrogen atom; $C_1$-$C_4$ alkyl radicals optionally substituted by at least one radical chosen from hydroxyl, ($C_1$-$C_2$)alkoxy, amino, (di) alkyl($C_1$-$C_2$)amino, carboxyl, and $C_1$-$C_4$ alkyl carboxylate radicals; and phenyl radicals optionally substituted by at least one radical chosen from hydroxyl, amino, and ($C_1$-$C_2$)alkoxy radicals.

In at least one embodiment, $R_3$ and $R_4$, which are identical or different, are chosen from a hydrogen atom, methyl, ethyl, isopropyl, 2-hydroxyethyl, 3-hydroxypropyl, 2-hydroxypropyl, ethyl radicals substituted by an ethyl carboxylate, and ethyl radicals substituted by a carboxyl radical. According to another embodiment, $R_3$, $R_4$ and $R_5$ are a hydrogen atom or methyl radicals.

According to yet another aspect of the present disclosure, $R_3$ and $R_4$ form, together with the nitrogen atom to which they are attached, a 5- to 7-membered heterocyclic ring chosen from pyrrolidine, piperidine, homopiperidine, piperazine, homopiperazine, and morpholine, wherein the heterocycles may be substituted by at least one radical chosen from hydroxyl, amino, (di)alkyl($C_1$-$C_2$)amino, (di)hydroxyalkyl ($C_1$-$C_2$)amino, (di)alkyl($C_1$-$C_2$)carboxamido, carboxyl, and $C_1$-$C_4$ alkyl radicals optionally substituted by at least one radical chosen from hydroxyl, amino, and $C_1$-$C_2$ (di)alkylamino radicals.

According to at least one embodiment of the present disclosure, $R_3$ and $R_4$ form, together with the nitrogen atom to which they are attached, a 5- to 7-membered ring chosen from pyrrolidine, 2,5-dimethylpyrrolidine, pyrrolidine-2-carboxylic acid,
3-hydroxypyrrolidine-2-carboxylic acid, 4-hydroxypyrrolidine-2-carboxylic acid,
2,4-dicarboxypyrrolidine, 3-hydroxy-2-hydroxymethylpyrrolidine, 2-carboxamidopyrrolidine,
3-hydroxy-2-carboxamidopyrrolidine, 2-(diethylcarboxamido)pyrrolidine,
2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylamino pyrrolidine,
3-dimethylaminopyrrolidine, 4-amino-3-hydroxypyrrolidine, 3-hydroxy-4-(2-hydroxyethyl)-aminopyrrolidine, piperidine, 2,6-dimethylpiperidine, 2-carboxypiperidine,
2-carboxamidopiperidine, 2-hydroxymethylpiperidine, 3-hydroxy-2-hydroxymethylpiperidine,
3-hydroxypiperidine, 4-hydroxypiperidine, 3-hydroxymethylpiperidine, homopiperidine,
2-carboxyhomopiperidine, 2-carboxamidohomopiperidine, homopiperazine, N-methyl-homopiperazine, N-(2-hydroxyethyl)homopiperazine, and morpholine.

In at least one embodiment, $R_3$ and $R_4$ form, together with the nitrogen atom to which they are attached, a 5- to 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, 4-hydroxypiperidine, homopiperidine, homopiperazine, N-methyl homopiperazine, N-(2-hydroxyethyl)-homopiperazine, and morpholine.

According to at least one embodiment of the present disclosure, $R_3$ and $R_4$ form, together with the nitrogen atom to which they are attached, a 5-membered ring such as pyrrolidine, 3-hydroxypyrrolidine, 3-aminopyrrolidine, and 3-dimethylaminopyrrolidine.

In another aspect of the present disclosure, Z is a radical chosen from methyl, amino, ethylamino, isopropylamino, and pyrrolidine radicals.

In yet another aspect of the present disclosure, U is CR or N, and R is chosen from a hydrogen atom, methyl radicals, methoxy radicals, 2-hydroxyethoxy radicals, methylamino radicals, dimethylamino radicals, hydroxyethylamino radicals, dihydroxyethylamino radicals and methyl(hydroxyethyl)amino radicals.

According to at least one embodiment, U is CR or N, and R is chosen from a hydrogen atom, methyl radicals, methoxy radicals, and 2-hydroxyethoxy radicals.

According to one aspect of the present disclosure, X is chosen from a hydroxyl radical; $NR'_1R''_1$ radicals wherein $R'_1$ and $R''_1$ are independently chosen from a hydrogen atom; and $C_1$-$C_6$ alkyl radicals optionally substituted by at least one hydroxyl radical. In one embodiment, X is chosen from a hydroxyl radical; and $NR'_1R''_1$ radicals wherein $R'_1$ and $R''_1$ are each independently chosen from a hydrogen atom, methyl radicals, and 2-hydroxyethyl radicals.

According to another aspect of the present disclosure, $R'_1$ and $R''_1$ form a heterocycle chosen from pyrrolidine, piperidine, homopiperidine, piperazine, homopiperazine, and morpholine, wherein the heterocycles are optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals. By way of non-limiting example, these heterocycles are chosen from pyrrolidine, 2,5-dimethylpyrrolidine, pyrrolidine-2-carboxylic acid, 3-hydroxy-pyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido) pyrrolidine, 2-hydroxymethylpyrrolidine, 3,4-dihydroxy-2-hydroxymethylpyrrolidine, 3-hydroxy-pyrrolidine, 3,4-dihydroxypyrrolidine, 3-aminopyrrolidine, 3-methylamino pyrrolidine, 3-dimethylaminopyrrolidine, 4-amino-3-hydroxypyrrolidine, 3-hydroxy-4-(2-hydroxyethyl)-aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methyl-homopiperazine, N-(2-hydroxyethyl)homopiperazine, and morpholine.

In at least one embodiment, these heterocycles are chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, 4-hydroxypiperidine, homopiperidine, homopiperazine, N-methyl homopiperazine, N-(2-hydroxyethyl)homopiperazine, and morpholine.

According to at least one embodiment of the present disclosure, $R_1$ and $R''_1$ form, together with the nitrogen atom to which they are attached, a 5-membered ring such as pyrrolidine, 3-hydroxypyrrolidine, 3-aminopyrrolidine, and 3-dimethylaminopyrrolidine.

According to another aspect of the present disclosure, V is chosen from:
an oxygen atom;
$NR'_1$ wherein $R''_1$ is chosen from a hydrogen atom and $C_1$-$C_6$ alkyl radicals optionally substituted by at least one hydroxyl radical; and
$N+R'_1R''_1$ wherein $R'_1$ and $R''_1$ are independently chosen from a hydrogen atom, and $C_1$-$C_6$ alkyl radicals optionally substituted by at least one hydroxyl radical, or $R'_1$ and $R''_1$ may form, together with the nitrogen atom to which they are attached, a saturated or unsaturated heterocycle comprising 5 to 7 members.

In at least one embodiment, V is chosen from:
an oxygen atom;
$NR'_1$ wherein $R'_1$ is chosen from a hydrogen atom and $C_1$-$C_6$ alkyl radicals optionally substituted by at least one hydroxyl radical; and
$N+R'_1R''_1$ wherein $R'_1$ and $R''_1$ are independently chosen from a hydrogen atom and $C_1$-$C_6$ alkyl radicals.

In another embodiment, $R'_1$ and/or $R''_1$ are chosen from a hydrogen atom, methyl radicals, and 2-hydroxyethyl radicals.

According to another embodiment of the present disclosure, X and U, or independently V and U, form a 6-membered ring of morpholine type which is optionally substituted by at least one $C_1$-$C_4$ alkyl radical.

According to another aspect of the present disclosure, each instance of Y, which may be identical or different, is chosen from a hydroxyl radical, $C_1$-$C_4$ alkyl radicals, halogen atoms, an oxygen atom substituted by a $C_1$-$C_4$ alkyl radical optionally substituted by at least one hydroxyl radical; and $NR'_2R'_3$;

wherein $R'_2$ and $R'_3$, which are identical or different, may be chosen from a hydrogen atom;

$C_1$-$C_4$ alkylcarbonyl radicals optionally substituted by a quaternary ammonium group such as a trialkylammonium or by a cationic or non-cation nitrogen-containing heterocycle such as, for example, an imidazole group, a thiazole group, a pyridine group, a piperidine group, a pyrrolidine group, a pyrimidine group, a pyrazine group, an imidazolium group, a pyridinium group, a thiazolium group, a pyrrolidinium group, a piperidinium group, a pyrimidinium group, wherein these nitrogen-containing heterocycles are optionally substituted by at least one $C_1$-$C_4$ alkyl radical; aminocarbonyl radical; and $C_1$-$C_6$ alkyl radical optionally substituted by at least one hydroxyl radical; or $R'_2$ and $R'_3$ may form, together with the nitrogen atom to which they are attached, a saturated heterocycle comprising 5 to 7 members.

Accordingly, these heterocycles may be chosen from pyrrolidine, piperidine, homopiperidine, piperazine, homopiperazine, and morpholine, wherein the heterocycles are substituted by at least one radical chosen from halogen atoms and amino, (di)alkyl($C_1$-$C_4$)amino, hydroxy, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals.

Two radicals Y carried by two adjacent carbon atoms may form, together with the carbon atoms to which they are attached, an aromatic or non-aromatic, saturated or unsaturated, cyclic or heterocyclic group containing 5 or 6 members.

In at least one embodiment, each instance of Y, which may be identical or different, is a radical chosen from a hydroxyl radical, methyl radicals, chlorine atom, methoxy radicals, 2-hydroxyethoxy radicals, amino radicals, acetylamino radicals, (2-hydroxyethyl)amino radicals, 2-[(3-methyl-1H-imidazol-1-ium)acetyl]amino radicals, pyrrolidin-1-yle radicals, aminocarbonylamino radicals, or two radicals Y carried by two adjacent carbon atoms may form, together with the carbon atoms to which they are attached, a benzene, pyrrole, pyrrolidine, pyrazole, furan, morpholine or imidazole ring, optionally substituted by at least one $C_1$-$C_4$ alkyl radical.

According to another embodiment, An- is chosen from halides, such as chloride, bromide, fluoride, and iodide; hydroxides; sulfates; hydrogen sulfates; phosphates; hydrogen phosphates; alkyl($C_1$-$C_6$)sulfates, for example, methyl sulfate and ethyl sulfate; acetates; tartrates; oxalates; alkyl ($C_1$-$C_6$)sulfonates, such as a methyl sulfonate; aryl sulphonates which is substituted or unsubstituted by a $C_1$-$C_4$ alkyl radical, such as a 4-tolylsulfonate; methosulfates; and perchlorates.

The leuco compounds of formula (I), and the azomethine dyes with a pyrazolinone unit of formula (II), may optionally be salified with strong mineral acids, such as HCl, HBr, HI, $H_2SO_4$, $H_3PO_4$, and organic acids, for example, acetic, lactic, tartaric, citric, succinic, benzenesulfonic, para-toluenesulfonic, formic, and methanesulfonic acid.

They may also be in the form of solvates, for example hydrates and linear and branched alcohol solvates, such as ethanol and isopropanol solvate.

Non-limiting examples of azomethine dyes with a pyrazolinone unit of formula (II) include the compounds presented below, wherein An⁻ is as defined before:

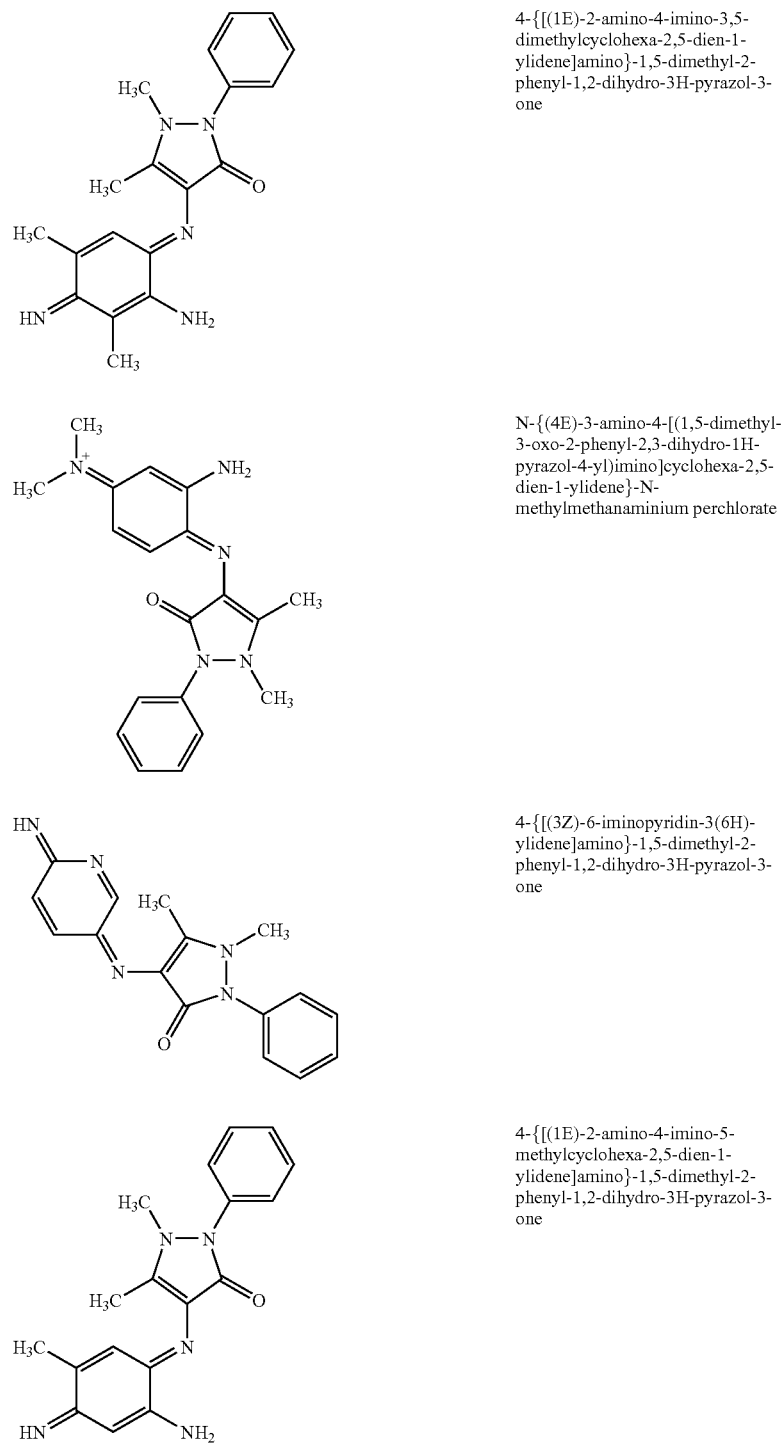

4-{[(1E)-2-amino-4-imino-3,5-dimethylcyclohexa-2,5-dien-1-ylidene]amino}-1,5-dimethyl-2-phenyl-1,2-dihydro-3H-pyrazol-3-one N-{(4E)-3-amino-4-[(1,5-dimethyl-3-oxo-2-phenyl-2,3-dihydro-1H-pyrazol-4-yl)imino]cyclohexa-2,5-dien-1-ylidene}-N-methylmethanaminium perchlorate 4-{[(3Z)-6-iminopyridin-3(6H)-ylidene]amino}-1,5-dimethyl-2-phenyl-1,2-dihydro-3H-pyrazol-3-one 4-{[(1E)-2-amino-4-imino-5-methylcyclohexa-2,5-dien-1-ylidene]amino}-1,5-dimethyl-2-phenyl-1,2-dihydro-3H-pyrazol-3-one -continued

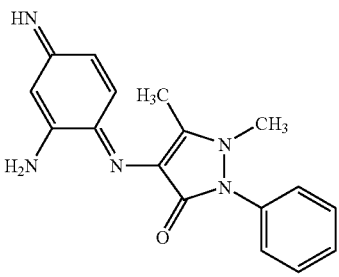

4-{[(1Z)-2-amino-4-iminocyclohexa-2,5-dien-1-ylidene]amino}-1,5-dimethyl-2-phenyl-1,2-dihydro-3H-pyrazol-3-one

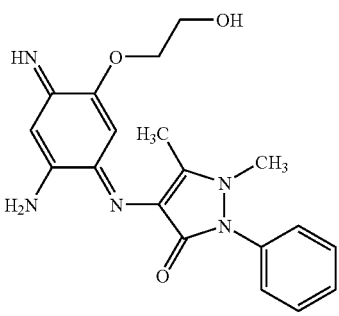

4-{[(1Z)-2-amino-5-(2-hydroxyethoxy)-4-iminocyclohexa-2,5-dien-1-ylidene]amino}-1,5-dimethyl-2-phenyl-1,2-dihydro-3H-pyrazol-3-one

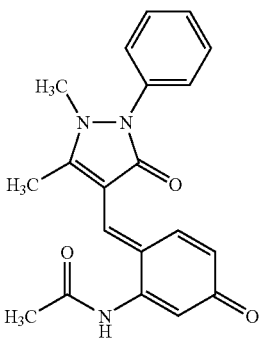

N-{(6E)-6-[(1,5-dimethyl-3-oxo-2-phenyl-2,3-dihydro-1H-pyrazol-4-yl)imino]-3-oxocyclohexa-1,4-dien-1-yl}acetamide

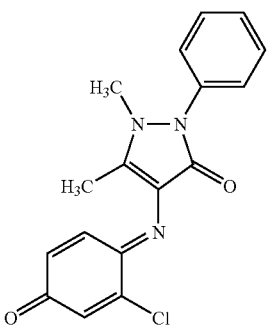

4-{[(1E)-2-chloro-4-oxocyclohexa-2,5-dien-1-ylidene]amino}-1,5-dimethyl-2-phenyl-1,2-dihydro-3H-pyrazol-3-one

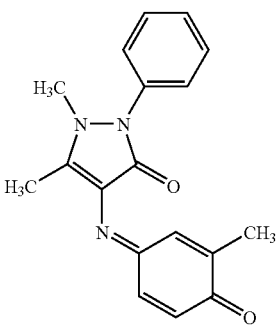

1,5-dimethyl-4-{[(1Z)-3-methyl-4-oxocyclohexa-2,5-dien-1-ylidene]amino}-2-phenyl-1,2-dihydro-3H-pyrazol-3-one -continued

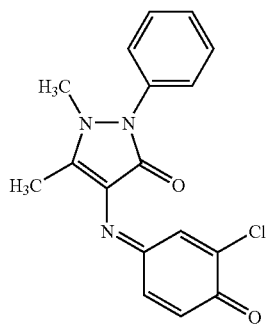

4-{[(1Z)-3-chloro-4-oxocyclohexa-2,5-dien-1-ylidene]amino}-1,5-dimethyl-2-phenyl-1,2-dihydro-3H-pyrazol-3-one

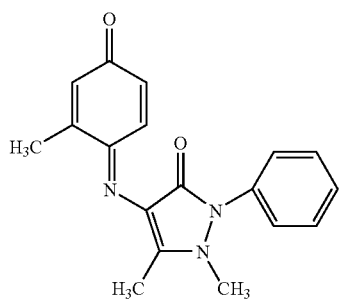

1,5-dimethyl-4-{[(1Z)-2-methyl-4-oxocyclohexa-2,5-dien-1-ylidene]amino}-2-phenyl-1,2-dihydro-3H-pyrazol-3-one

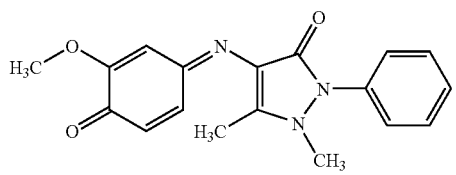

4-{[(1E)-3-methoxy-4-oxocyclohexa-2,5-dien-1-ylidene]amino}-1,5-dimethyl-2-phenyl-1,2-dihydro-3H-pyrazol-3-one

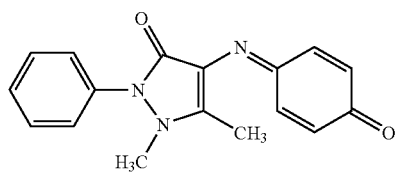

1,5-dimethyl-4-[(4-oxocyclohexa-2,5-dien-1-ylidene)amino]-2-phenyl-1,2-dihydro-3H-pyrazol-3-one

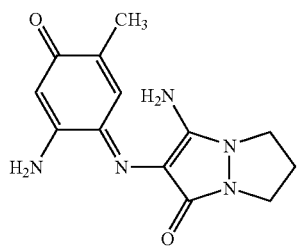

3-amino-2-{[(1E)-2-amino-5-methyl-4-oxocyclohexa-2,5-dien-1-ylidene]amino}-6,7-dihydro-1H,5H-pyrazolo[1,2-a]pyrazol-1-one

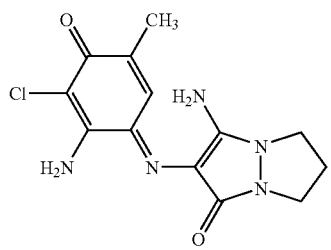

3-amino-2-{[(1E)-2-amino-3-chloro-5-methyl-4-oxocyclohexa-2,5-dien-1-ylidene]amino}-6,7-dihydro-1H,5H-pyrazolo[1,2-a]pyrazol-1-one

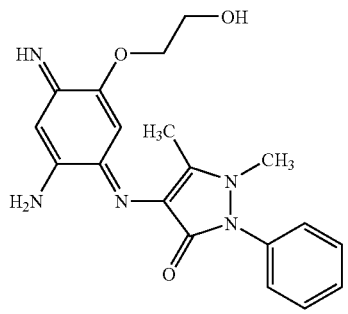

4-{[(1Z)-2-amino-5-(2-hydroxyethoxy)-4-iminocyclohexa-2,5-dien-1-ylidene]amino}-1,5-dimethyl-2-phenyl-1,2-dihydro-3H-pyrazol-3-one

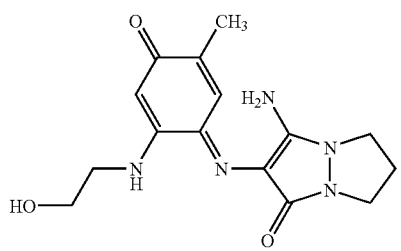

3-amino-2-({(1E)-2-[(2-hydroxyethyl)amino]-5-methyl-4-oxocyclohexa-2,5-dien-1-ylidene}amino)-6,7-dihydro-1H,5H-pyrazolo[1,2-a]pyrazol-1-one

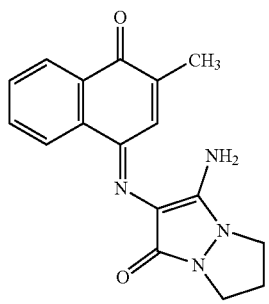

3-amino-2-{[(1E)-3-methyl-4-oxonaphthalen-1(4H)-ylidene]amino}-6,7-dihydro-1H,5H-pyrazolo[1,2-a]pyrazol-1-one

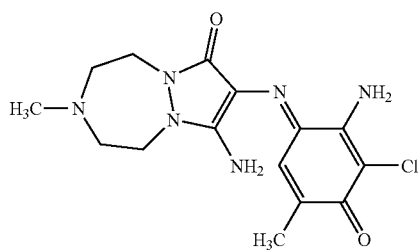

9-amino-8-[(2-amino-3-chloro-5-methyl-4-oxocyclohexa-2,5-dien-1-ylidene)amino]-3-methyl-2,3,4,5-tetrahydro-1H,7H-pyrazolo[1,2-a][1,2,5]triazepin-7-one

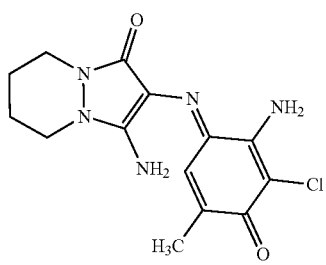

3-amino-2-[(2-amino-3-chloro-5-methyl-4-oxocyclohexa-2,5-dien-1-ylidene)amino]-5,6,7,8-tetrahydro-1H-pyrazolo[1,2-a]pyridazin-1-one -continued

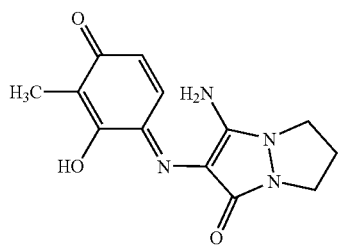

3-amino-2-{[(1E)-2-hydroxy-3-methyl-4-oxocyclohexa-2,5-dien-1-ylidene]amino}-6,7-dihydro-1H,5H-pyrazolo[1,2-a]pyrazol-1-one

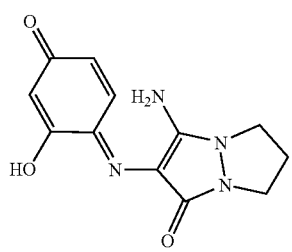

3-amino-2-{[(1E)-2-hydroxy-4-oxocyclohexa-2,5-dien-1-ylidene]amino}-6,7-dihydro-1H,5H-pyrazolo[1,2-a]pyrazol-1-one

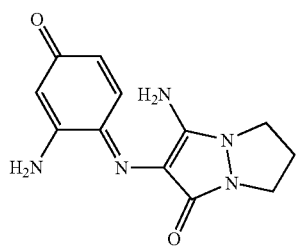

3-amino-2-{[(1E)-2-amino-4-oxocyclohexa-2,5-dien-1-ylidene]amino}-6,7-dihydro-1H,5H-pyrazolo[1,2-a]pyrazol-1-one

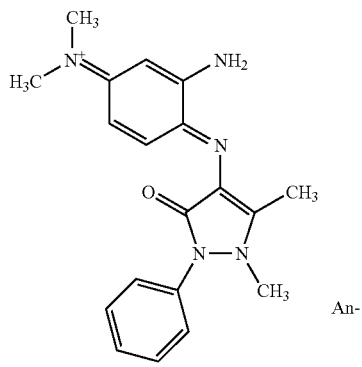

N-{(4E)-3-amino-4-[(1,5-dimethyl-3-oxo-2-phenyl-2,3-dihydro-1H-pyrazol-4-yl)imino]cyclohexa-2,5-dien-1-ylidene}-N-methylmethanaminium, An-

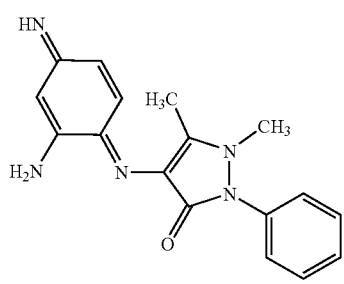

4-{[(1E)-2-amino-4-iminocyclohexa-2,5-dien-1-ylidene]amino}-1,5-dimethyl-2-phenyl-1,2-dihydro-3H-pyrazol-3-one -continued

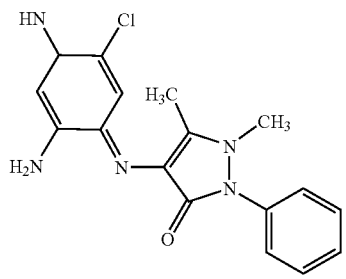

4-{[(1Z)-2-amino-5-chloro-4-iminocyclohexa-2,5-dien-1-ylidene]amino}-1,5-dimethyl-2-phenyl-1,2-dihydro-3H-pyrazol-3-one

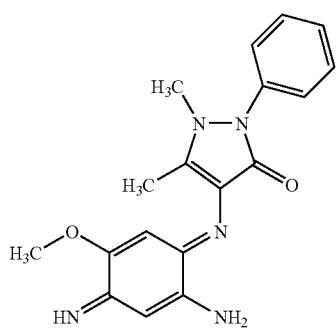

4-{[(1E)-2-amino-4-imino-5-methoxycyclohexa-2,5-dien-1-ylidene]amino}-1,5-dimethyl-2-phenyl-1,2-dihydro-3H-pyrazol-3-one

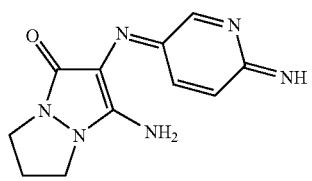

3-amino-2-{[(3E)-6-iminopyridin-3(6H)-ylidene]amino}-6,7-dihydro-1H,5H-pyrazolo[1,2-a]pyrazol-1-one

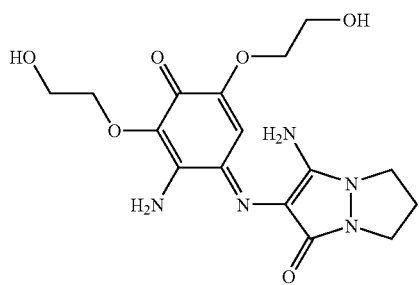

3-amino-2-{[(1E)-2-amino-3,5-bis(2-hydroxyethoxy)-4-oxocyclohexa-2,5-dien-1-ylidene]amino}-6,7-dihydro-1H,5H-pyrazolo[1,2-a]pyrazol-1-one

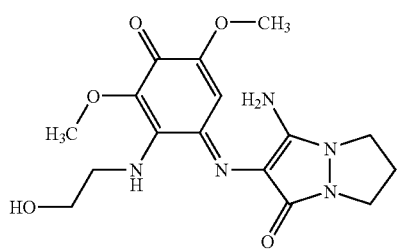

3-amino-2-({(1E)-2-[(2-hydroxyethyl)amino]-3,5-dimethoxy-4-oxocyclohexa-2,5-dien-1-ylidene}amino)-6,7-dihydro-1H,5H-pyrazolo[1,2-a]pyrazol-1-one

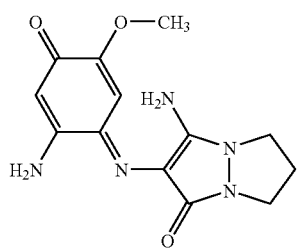

3-amino-2-{[(1E)-2-amino-5-methoxy-4-oxocyclohexa-2,5-dien-1-ylidene]amino}-6,7-dihydro-1H,5H-pyrazolo[1,2-a]pyrazol-1-one

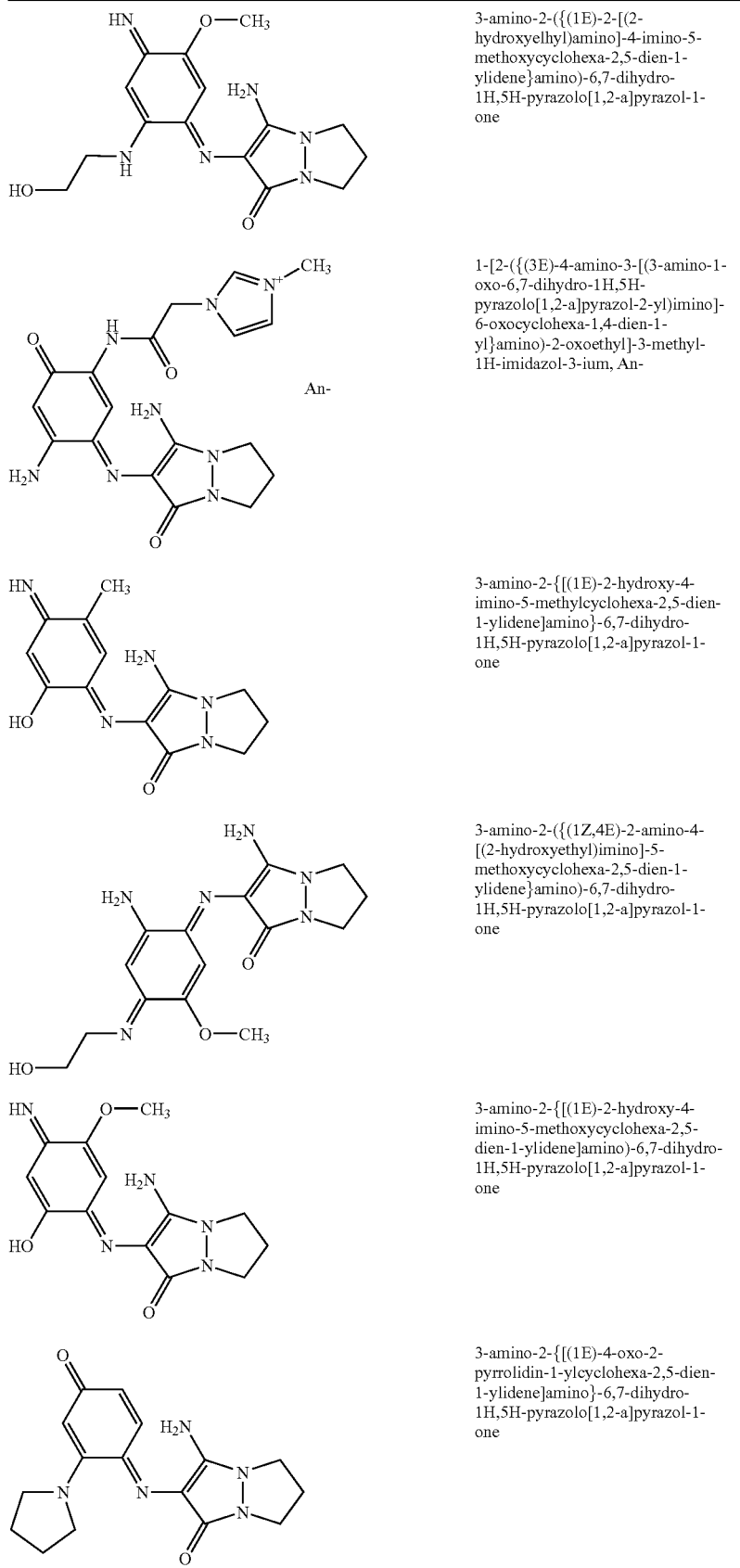

3-amino-2-({(1E)-2-[(2-hydroxyelhyl)amino]-4-imino-5-methoxycyclohexa-2,5-dien-1-ylidene}amino)-6,7-dihydro-1H,5H-pyrazolo[1,2-a]pyrazol-1-one 1-[2-({(3E)-4-amino-3-[(3-amino-1-oxo-6,7-dihydro-1H,5H-pyrazolo[1,2-a]pyrazol-2-yl)imino]-6-oxocyclohexa-1,4-dien-1-yl}amino)-2-oxoethyl]-3-methyl-1H-imidazol-3-ium, An- 3-amino-2-{[(1E)-2-hydroxy-4-imino-5-methylcyclohexa-2,5-dien-1-ylidene]amino}-6,7-dihydro-1H,5H-pyrazolo[1,2-a]pyrazol-1-one 3-amino-2-({(1Z,4E)-2-amino-4-[(2-hydroxyethyl)imino]-5-methoxycyclohexa-2,5-dien-1-ylidene}amino)-6,7-dihydro-1H,5H-pyrazolo[1,2-a]pyrazol-1-one 3-amino-2-{[(1E)-2-hydroxy-4-imino-5-methoxycyclohexa-2,5-dien-1-ylidene]amino}-6,7-dihydro-1H,5H-pyrazolo[1,2-a]pyrazol-1-one 3-amino-2-{[(1E)-4-oxo-2-pyrrolidin-1-ylcyclohexa-2,5-dien-1-ylidene]amino}-6,7-dihydro-1H,5H-pyrazolo[1,2-a]pyrazol-1-one -continued

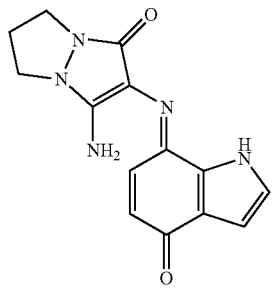

(7Z)-7-[(3-amino-1-oxo-6,7-
dihydro-1H,5H-pyrazolo[1,2-
a]pyrazol-2-yl)imino]-1,7-dihydro-
4H-indol-4-one

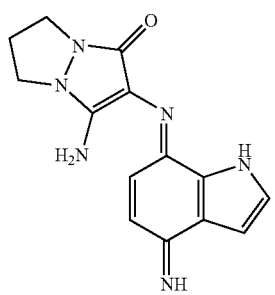

3-amino-2-{[(7E)-4-imino-1,4-
dihydro-7H-indol-7-
ylidene]amino)-6,7-dihydro-1H,5H-
pyrazolo[1,2-a]pyrazol-1-one

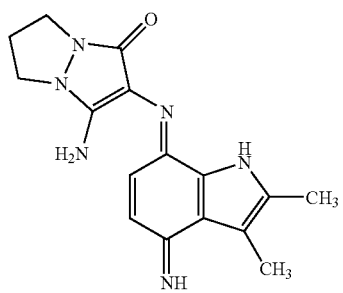

3-amino-2-{[(7E)-4-imino-2,3-
dimethyl-1,4-dihydro-7H-indol-7-
ylidene]amino}-6,7-dihydro-1H,5H-
pyrazolo[1,2-a]pyrazol-1-one

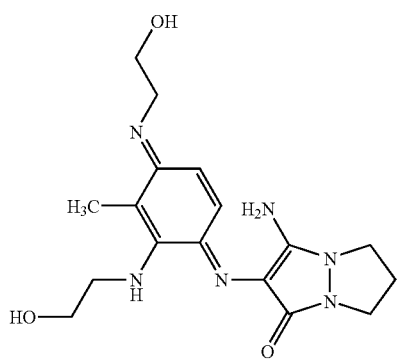

3-amino-2-({(1E,4E)-2-[(2-
hydroxyethyl)amino]-4-[(2-
hydroxyethyl)imino]-3-
methylcyclohexa-2,5-dien-1-
ylidene}amino)-6,7-dihydro-
1H,5H-pyrazolo[1,2-a]pyrazol-1-
one

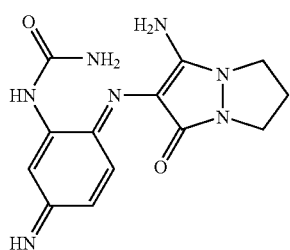

N-{(6Z)-6-[(3-amino-1-oxo-6,7-
dihydro-1H,5H-pyrazolo[1,2-
a]pyrazol-2-yl)imino]-3-
iminocyclohexa-1,4-dien-1-yl}urea -continued

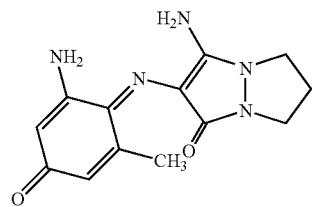

3-amino-2-{[(1Z)-2-amino-6-methyl-4-oxocyclohexa-2,5-dien-1-ylidene]amino}-6,7-dihydro-1H,5H-pyrazolo[1,2-a]pyrazol-1-one

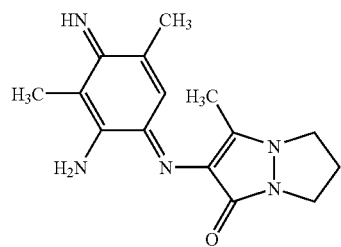

2-{[(1E)-2-amino-4-imino-3,5-dimethylcyclohexa-2,5-dien-1-ylidene]amino}-3-methyl-6,7-dihydro-1H,5H-pyrazolo[1,2-a]pyrazol-1-one

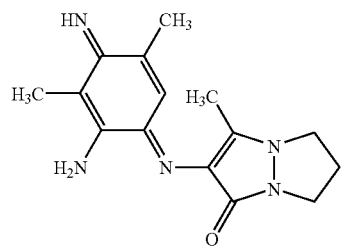

2-{[(1E)-2-amino-4-imino-3,5-dimethyloyolohexa-2,5-dien-1-ylidene]amino}-3-methyl-6,7-dihydro-1H,5H-pyrazolo[1,2-a]pyrazol-1-one

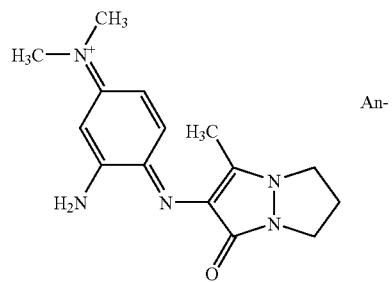

An-

N-{(4E)-3-amino-4-[(3-methyl-1-oxo-6,7-dihydro-1H,5H-pyrazolo[1,2-a]pyrazol-2-yl)imino]cyclohexa-2,5-dien-1-ylidene}-N-methylmethanaminium, An-

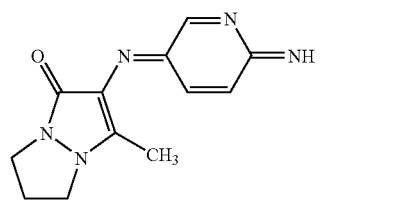

2-{[(3E)-6-iminopyridin-3(6H)-ylidene]amino}-3-methyl-6,7-dihydro-1H,5H-pyrazolo[1,2-a]pyrazol-1-one

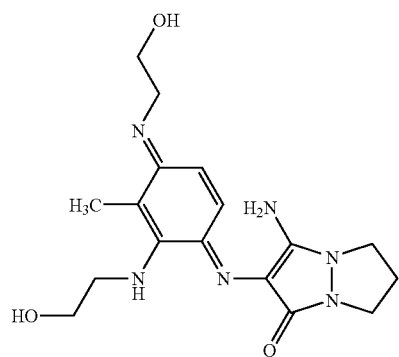

3-amino-2-({(1E,4E)-2-[(2-hydroxyethyl)amino]-4-[(2-hydroxyethyl)imino]-3-methylcyclohexa-2,5-dien-1-ylidene}amino)-6,7-dihydro-1H,5H-pyrazolo[1,2-a]pyrazol-1-one -continued

| | |
|---|---|
| 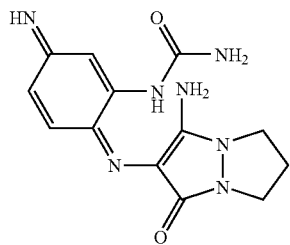 | N-{(6Z)-6-[(3-amino-1-oxo-6,7-dihydro-1H,5H-pyrazolo[1,2-a]pyrazol-2-yl)imino]-3-iminocyclohexa-1,4-dien-1-yl}urea |
| 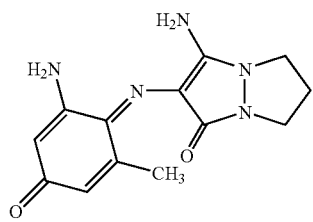 | 3-amino-2-{[(1Z)-2-amino-6-methyl-4-oxocyclohexa-2,5-dien-1-ylidene]amino}-6,7-dihydro-1H,5H-pyrazolo[1,2-a]pyrazol-1-one |
| 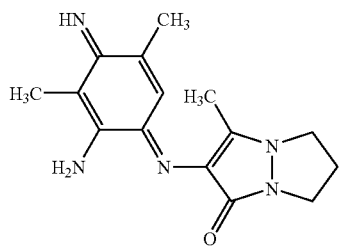 | 2-{[(1E)-2-amino-4-imino-3,5-dimethylcyclohexa-2,5-dien-1-ylidene]amino}-3-methyl-6,7-dihydro-1H,5H-pyrazolo[1,2-a]pyrazol-1-one |
| 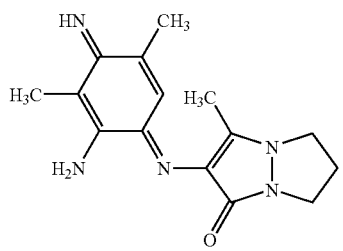 | 2-{[(1E)-2-amino-4-imino-3,5-dimethylcyclohexa-2,5-dien-1-ylidene]amino}-3-methyl-6,7-dihydro-1H,5H-pyrazolo[1,2-a]pyrazol-1-one |
| 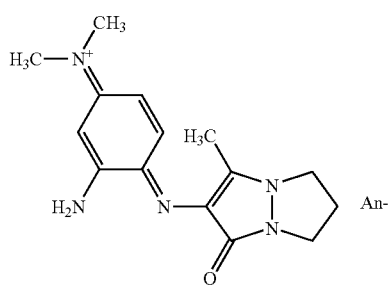 | N-{(4E)-3-amino-4-[(3-methyl-1-oxo-6,7-dihydro-1H,5H-pyrazolo[1,2-a]pyrazol-2-yl)imino]cyclohexa-2,5-dien-1-ylidene}-N-methylmethanaminium, An- |
| 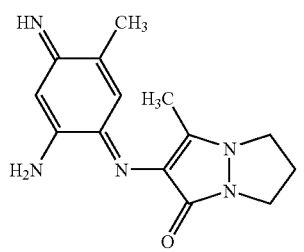 | 2-{[(1E)-2-amino-4-imino-5-methylcyclohexa-2,5-dien-1-ylidene]amino}-3-methyl-6,7-dihydro-1H,5H-pyrazolo[1,2-a]pyrazol-1-one |

-continued

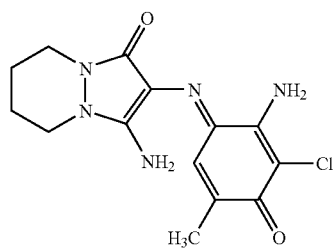
3-amino-2-{[(1E)-2-amino-3-chloro-5-methyl-4-oxocyclohexa-2,5-dien-1-ylidene]amino}-5,6,7,8-tetrahydro-1H-pyrazolo[1,2-a]pyridazin-1-one

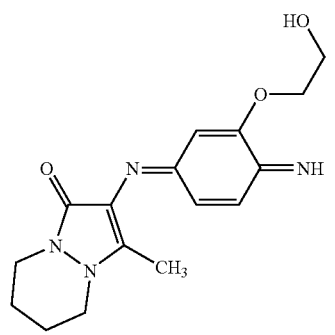
2-{[(1E)-3-(2-hydroxyethoxy)-4-iminocyclohexa-2,5-dien-1-ylidene]amino}-3-methyl-5,6,7,8-tetrahydro-1H-pyrazolo[1,2-a]pyridazin-1-one

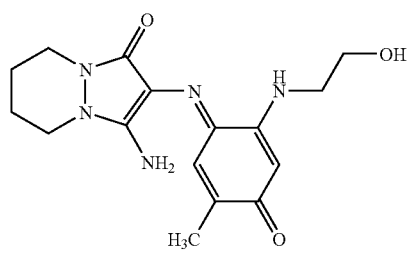
3-amino-2-({(1E)-2-[(2-hydroxyethyl)amino]-5-methyl-4-oxocyclohexa-2,5-dien-1-ylidene}amino)-5,6,7,8-tetrahydro-1H-pyrazolo[1,2-a]pyridazin-1-one

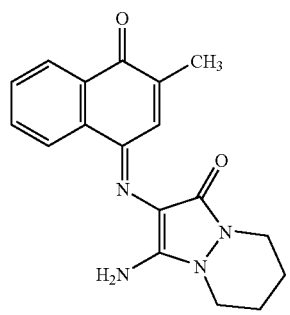
3-amino-2-{[(1E)-3-methyl-4-oxonaphthalen-1(4H)-ylidene]amino}-5,6,7,8-tetrahydro-1H-pyrazolo[1,2-a]pyridazin-1-one

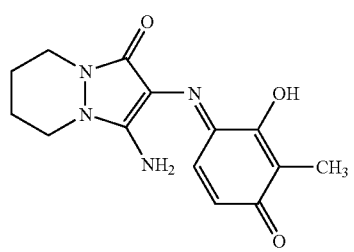
3-amino-2-{[(1E)-2-hydroxy-3-methyl-4-oxocyclohexa-2,5-dien-1-ylidene]amino}-5,6,7,8-tetrahydro-1H-pyrazolo[1,2-a]pyridazin-1-one -continued

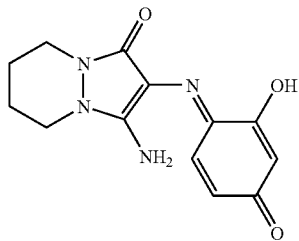
3-amino-2-{[(1E)-2-hydroxy-4-oxocyclohexa-2,5-dien-1-ylidene]amino}-5,6,7,8-tetrahydro-1H-pyrazolo[1,2-a]pyridazin-1-one

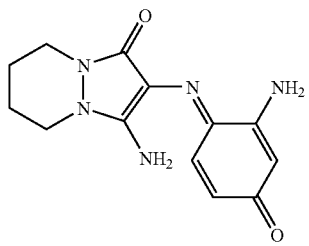
3-amino-2-{[(1E)-2-amino-4-oxocyclohexa-2,5-dien-1-ylidene]amino}-5,6,7,8-tetrahydro-1H-pyrazolo[1,2-a]pyridazin-1-one

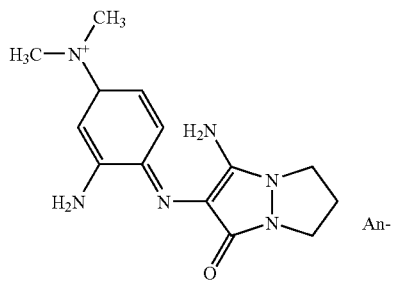
N-{(4E)-3-amino-4-[(3-amino-1-oxo-6,7-dihydro-1H,5H-pyrazolo[1,2-a]pyrazol-2-yl)imino]cyclohexa-2,5-dien-1-ylidene}-N-methylmethanaminium, An-

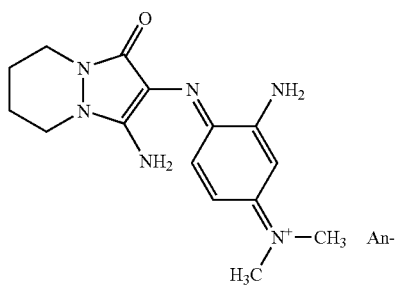
N-{(4E)-3-amino-4-[(3-amino-1-oxo-5,6,7,8-tetrahydro-1H-pyrazolo[1,2-a]pyridazin-2-yl)imino]cyclohexa-2,5-dien-1-ylidene}-N-methylmethanaminium, An-

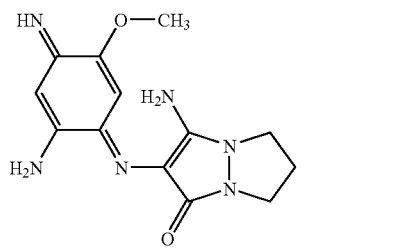
3-amino-2-{[(1E)-2-amino-4-imino-5-methoxycyclohexa-2,5-dien-1-ylidene]amino}-6,7-dihydro-1H,5H-pyrazolo[1,2-a]pyrazol-1-one

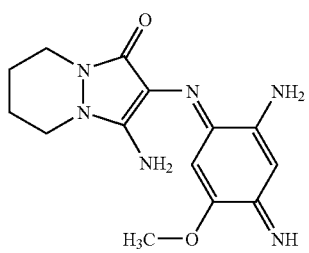
3-amino-2-{[(1E)-2-amino-4-imino-5-methoxycyclohexa-2,5-dien-1-ylidene]amino}-5,6,7,8-tetrahydro-1H-pyrazolo[1,2-a]pyridazin-1-one

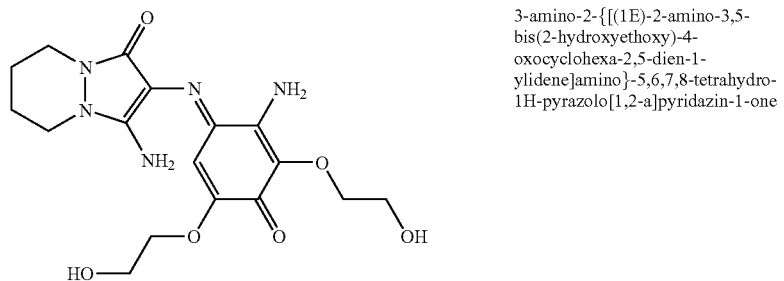
3-amino-2-{[(1E)-2-amino-3,5-bis(2-hydroxyethoxy)-4-oxocyclohexa-2,5-dien-1-ylidene]amino}-5,6,7,8-tetrahydro-1H-pyrazolo[1,2-a]pyridazin-1-one

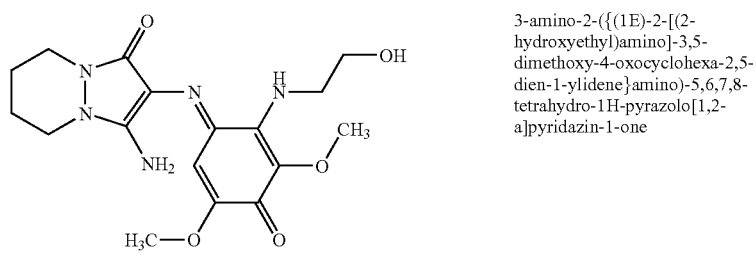
3-amino-2-({(1E)-2-[(2-hydroxyethyl)amino]-3,5-dimethoxy-4-oxocyclohexa-2,5-dien-1-ylidene}amino)-5,6,7,8-tetrahydro-1H-pyrazolo[1,2-a]pyridazin-1-one

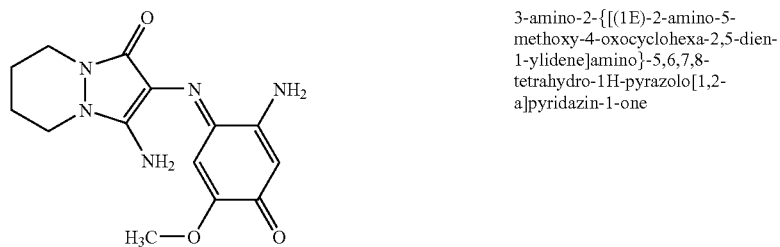
3-amino-2-{[(1E)-2-amino-5-methoxy-4-oxocyclohexa-2,5-dien-1-ylidene]amino}-5,6,7,8-tetrahydro-1H-pyrazolo[1,2-a]pyridazin-1-one

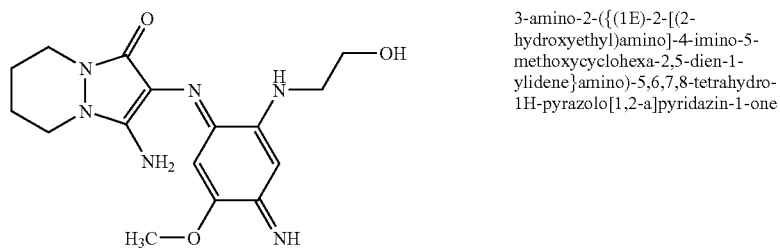
3-amino-2-({(1E)-2-[(2-hydroxyethyl)amino]-4-imino-5-methoxycyclohexa-2,5-dien-1-ylidene}amino)-5,6,7,8-tetrahydro-1H-pyrazolo[1,2-a]pyridazin-1-one

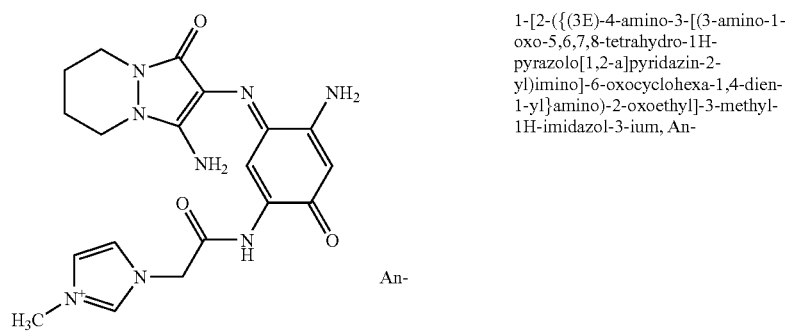
1-[2-({(3E)-4-amino-3-[(3-amino-1-oxo-5,6,7,8-tetrahydro-1H-pyrazolo[1,2-a]pyridazin-2-yl)imino]-6-oxocyclohexa-1,4-dien-1-yl}amino)-2-oxoethyl]-3-methyl-1H-imidazol-3-ium, An- -continued

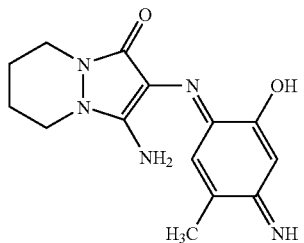

3-amino-2-{[(1E)-2-hydroxy-4-imino-5-methylcyclohexa-2,5-dien-1-ylidene]amino}-5,6,7,8-tetrahydro-1H-pyrazolo[1,2-a]pyridazin-1-one

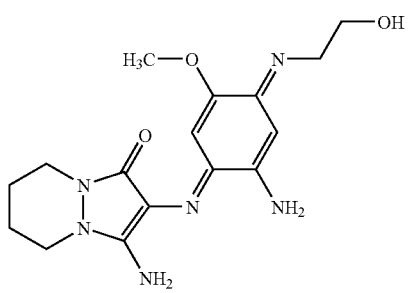

3-amino-2-({(1Z,4E)-2-amino-4-[(2-hydroxyethyl)imino]-5-methoxycyclohexa-2,5-dien-1-ylidene}amino)-5,6,7,8-tetrahydro-1H-pyrazolo[1,2-a]pyridazin-1-one

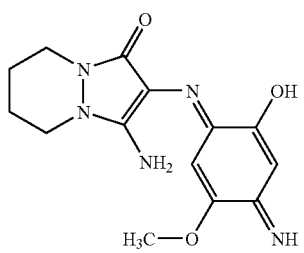

3-amino-2-{[(1E)-2-hydroxy-4-imino-5-methoxycyclohexa-2,5-dien-1-ylidene]amino}-5,6,7,8-tetrahydro-1H-pyrazolo[1,2-a]pyridazin-1-one

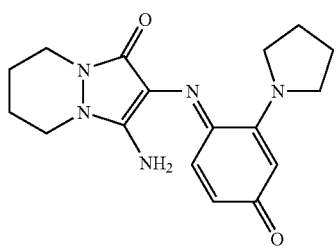

3-amino-2-{[(1E)-4-oxo-2-pyrrolidin-1-ylcyclohexa-2,5-dien-1-ylidene]amino}-5,6,7,8-tetrahydro-1H-pyrazolo[1,2-a]pyridazin-1-one

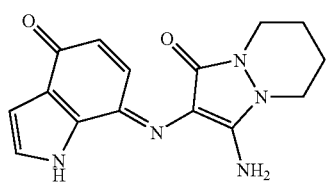

3-amino-2-{[(7Z)-4-oxo-1,4-dihydro-7H-indol-7-ylidene]amino}-5,6,7,8-tetrahydro-1H-pyrazolo[1,2-a]pyridazin-1-one

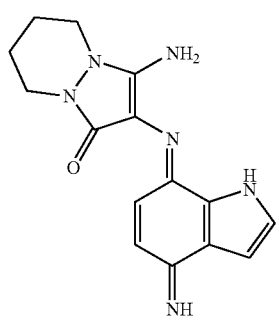

3-amino-2-{[(7E)-4-imino-1,4-dihydro-7H-indol-7-ylidene]amino}-5,6,7,8-tetrahydro-1H-pyrazolo[1,2-a]pyridazin-1-one

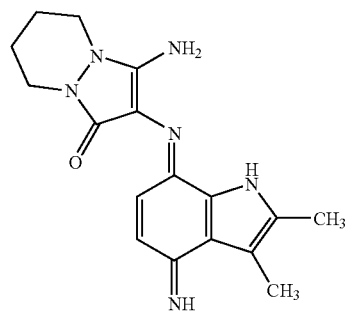

3-amino-2-{[(7E)-4-imino-2,3-dimethyl-1,4-dihydro-7H-indol-7-ylidene]amino}-5,6,7,8-tetrahydro-1H-pyrazolo[1,2-a]pyridazin-1-one

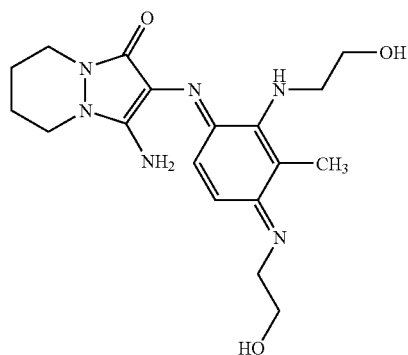

3-amino-2-({(1E,4E)-2-[(2-hydroxyethyl)amino]-4-[(2-hydroxyethyl)imino]-3-methylcyclohexa-2,5-dien-1-ylidene}amino)-5,6,7,8-tetrahydro-1H-pyrazolo[1,2-a]pyridazin-1-one

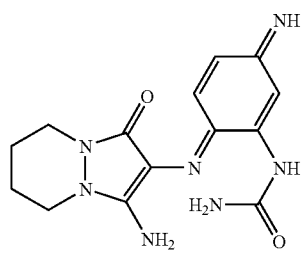

N-{(6Z)-6-[(3-amino-1-oxo-5,6,7,8-tetrahydro-1H-pyrazolo[1,2-a]pyridazin-2-yl)imino]-3-iminocyclohexa-1,4-dien-1-yl}urea

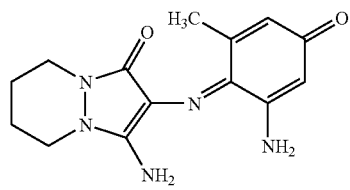

3-amino-2-{[(1Z)-2-amino-6-methyl-4-oxocyclohexa-2,5-dien-1-ylidene]amino}-5,6,7,8-tetrahydro-1H-pyrazolo[1,2-a]pyridazin-1-one

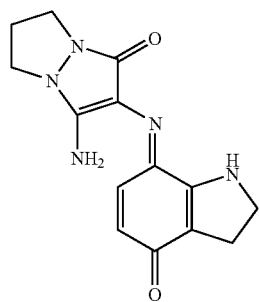

(7Z)-7-[(3-amino-1-oxo-6,7-dihydro-1H,5H-pyrazolo[1,2-a]pyrazol-2-yl)imino]-1,2,3,7-tetrahydro-4H-indol-4-one -continued

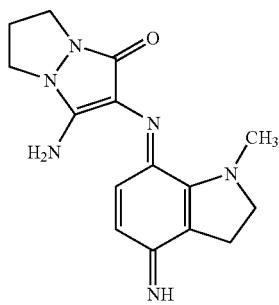
3-amino-2-{[(7E)-4-imino-1-methyl-1,2,3,4-tetrahydro-7H-indol-7-ylidene]amino}-6,7-dihydro-1H,5H-pyrazolo[1,2-a]pyrazol-1-one

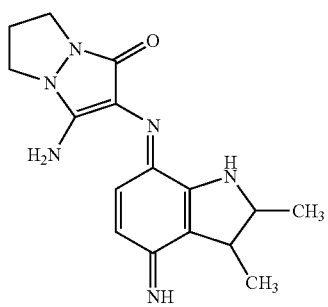
3-amino-2-{[(7E)-4-imino-2,3-dimethyl-1,2,3,4-tetrahydro-7H-indol-7-ylidene]amino}-6,7-dihydro-1H,5H-pyrazolo[1,2-a]pyrazol-1-one

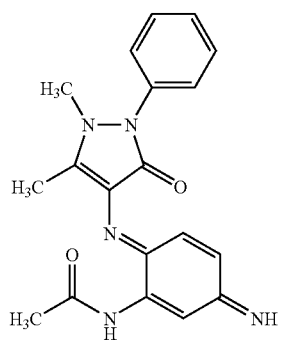
N-{(6E)-6-[(1,5-dimethyl-3-oxo-2-phenyl-2,3-dihydro-1H-pyrazol-4-yl)imino]-3-iminocyclohexa-1,4-dien-1-yl}acetamide

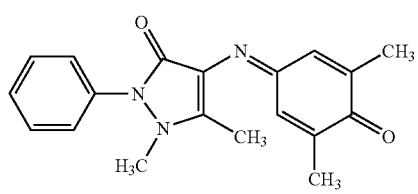
4-[(3,5-dimethyl-4-oxocyclohexa-2,5-dien-1-ylidene)amino]-1,5-dimethyl-2-phenyl-1,2-dihydro-3H-pyrazol-3-one

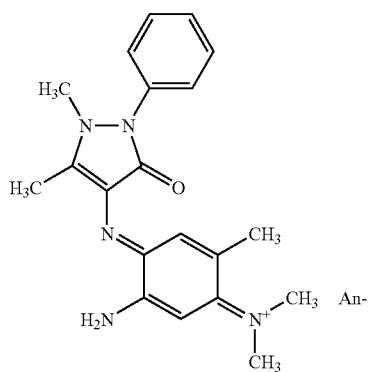
N-{(4E)-5-amino-4-[(1,5-dimethyl-3-oxo-2-phenyl-2,3-dihydro-1H-pyrazol-4-yl)imino]-2-methyloycloheza-2,5-dien-1-ylidene}-N-methylmethanaminium, An- -continued

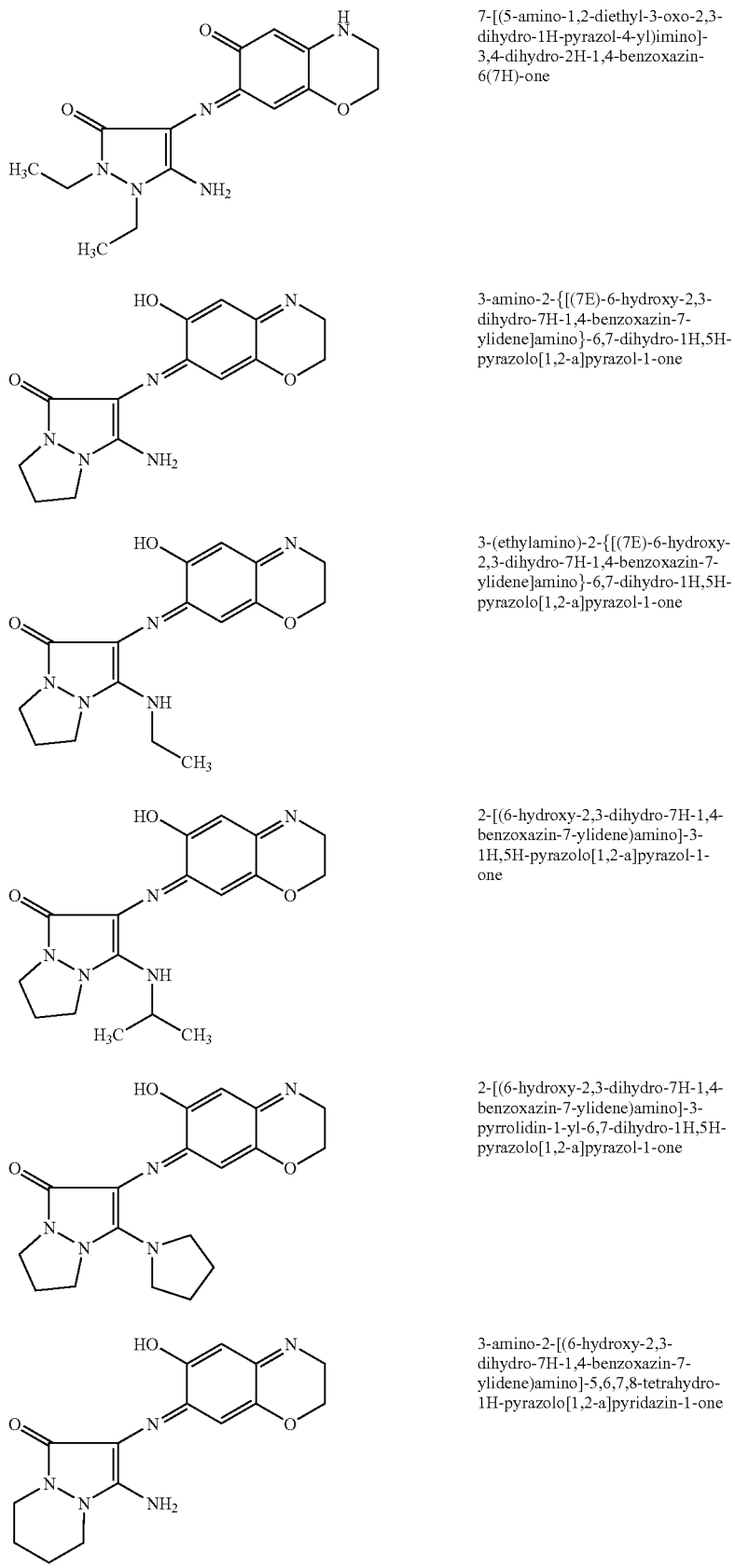

7-[(5-amino-1,2-diethyl-3-oxo-2,3-dihydro-1H-pyrazol-4-yl)imino]-3,4-dihydro-2H-1,4-benzoxazin-6(7H)-one 3-amino-2-{[(7E)-6-hydroxy-2,3-dihydro-7H-1,4-benzoxazin-7-ylidene]amino}-6,7-dihydro-1H,5H-pyrazolo[1,2-a]pyrazol-1-one 3-(ethylamino)-2-{[(7E)-6-hydroxy-2,3-dihydro-7H-1,4-benzoxazin-7-ylidene]amino}-6,7-dihydro-1H,5H-pyrazolo[1,2-a]pyrazol-1-one 2-[(6-hydroxy-2,3-dihydro-7H-1,4-benzoxazin-7-ylidene)amino]-3-1H,5H-pyrazolo[1,2-a]pyrazol-1-one 2-[(6-hydroxy-2,3-dihydro-7H-1,4-benzoxazin-7-ylidene)amino]-3-pyrrolidin-1-yl-6,7-dihydro-1H,5H-pyrazolo[1,2-a]pyrazol-1-one 3-amino-2-[(6-hydroxy-2,3-dihydro-7H-1,4-benzoxazin-7-ylidene)amino]-5,6,7,8-tetrahydro-1H-pyrazolo[1,2-a]pyridazin-1-one -continued

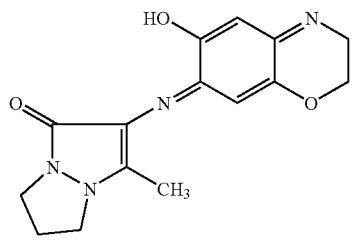

2-[(6-hydroxy-2,3-dihydro-7H-1,4-benzoxazin-7-ylidene)amino]-3-methyl-6,7-dihydro-1H,5H-pyrazolo[1,2-a]pyrazol-1-one

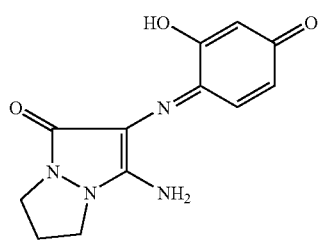

3-amino-2-[(2-hydroxy-4-oxocyclohexa-2,5-dien-1-ylidene)amino]-6,7-dihydro-1H,5H-pyrazolo[1,2-a]pyrazol-1-one

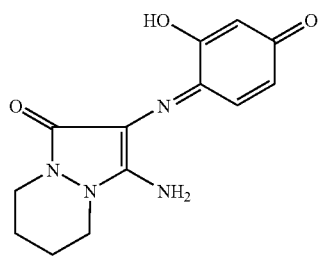

3-amino-2-[(2-hydroxy-4-oxocyclohexa-2,5-dien-1-ylidene)amino]-5,6,7,8-tetrahydro-1H-pyrazolo[1,2-a]pyridazin-1-one

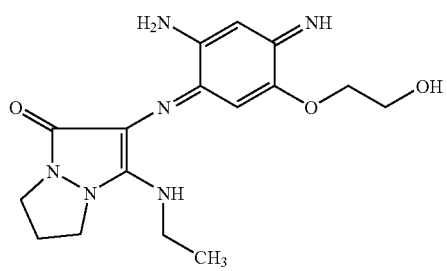

2-{[(1E)-2-amino-5-(2-hydroxyethoxy)-4-iminocyclohexa-2,5-dien-1-ylidene]amino}-3-(ethylamino)-6,7-dihydro-1H,5H-pyrazolo[1,2-a]pyrazol-1-one

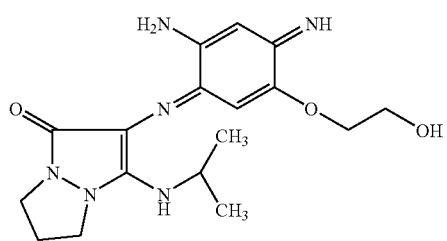

2-{[2-amino-5-(2-hydroxyethoxy)-4-iminocyclohexa-2,5-dien-1-ylidene]amino}-3-(isopropylamino)-6,7-dihydro-1H,5H-pyrazolo[1,2-a]pyrazol-1-one

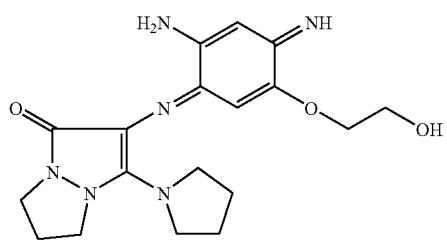

2-{[(1E)-2-amino-5-(2-hydroxyethoxy)-4-iminocyclohexa-2,5-dien-1-ylidene]amino}-3-pyrrolidin-1-yl-6,7-dihydro-1H,5H-pyrazolo[1,2-a]pyrazol-1-one

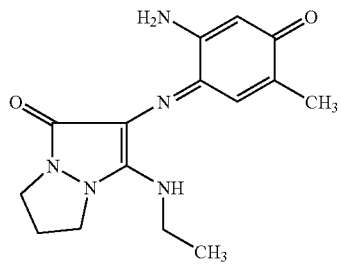

2-[(2-amino-5-methyl-4-oxocyclohexa-2,5-dien-1-ylidene)amino]-3-(ethylamino)-6,7-dihydro-1H,5H-pyrazolo[1,2-a]pyrazol-1-one

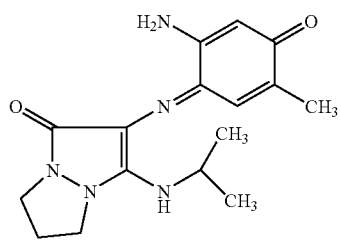

2-[(2-amino-5-methyl-4-oxocyclohexa-2,5-dien-1-ylidene)amino]-3-(isopropylamino)-6,7-dihydro-1H,5H-pyrazolo[1,2-a]pyrazol-1-one

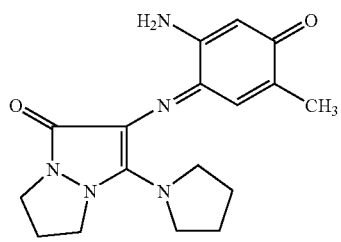

2-[(2-amino-5-methyl-4-oxocyclohexa-2,5-dien-1-ylidene)amino]-3-pyrrolidin-1-yl-6,7-dihydro-1H,5H-pyrazolo[1,2-a]pyrazol-1-one

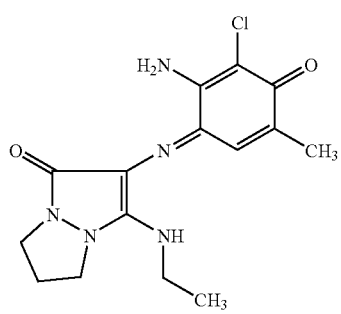

2-[(2-amino-3-chloro-5-methyl-4-oxocyclohexa-2,5-dien-1-ylidene)amino]-3-(ethylamino)-6,7-dihydro-1H,5H-pyrazolo[1,2-a]pyrazol-1-one

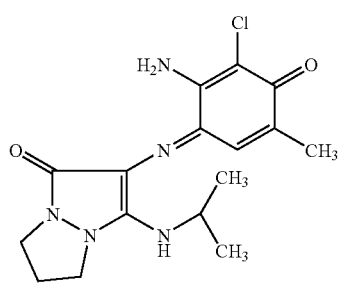

2-[(2-amino-3-chloro-5-methyl-4-oxocyclohexa-2,5-dien-1-ylidene)amino]-3-(isopropylamino)-6,7-dihydro-1H,5H-pyrazolo[1,2-a]pyrazol-1-one -continued

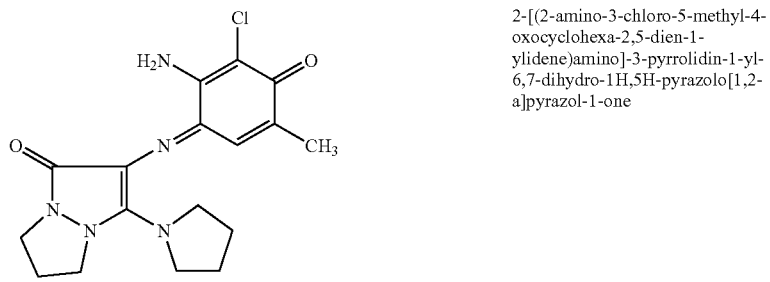

2-[(2-amino-3-chloro-5-methyl-4-oxocyclohexa-2,5-dien-1-ylidene)amino]-3-pyrrolidin-1-yl-6,7-dihydro-1H,5H-pyrazolo[1,2-a]pyrazol-1-one

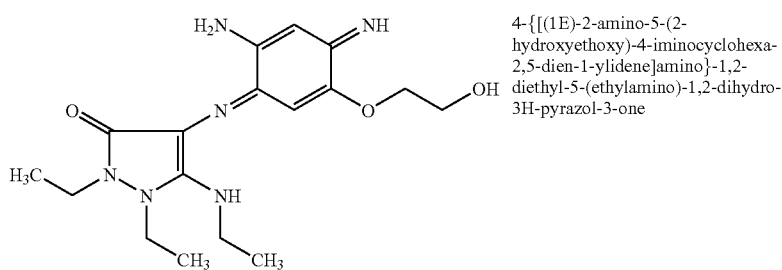

4-{[(1E)-2-amino-5-(2-hydroxyethoxy)-4-iminocyclohexa-2,5-dien-1-ylidene]amino}-1,2-diethyl-5-(ethylamino)-1,2-dihydro-3H-pyrazol-3-one

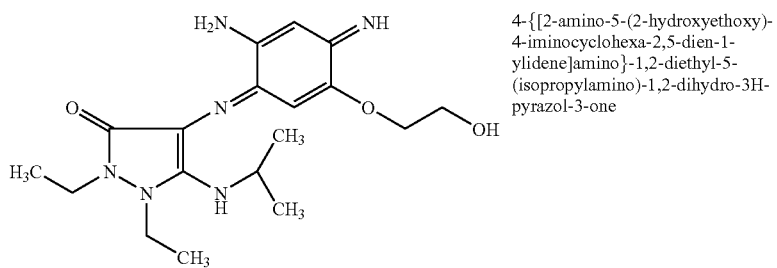

4-{[2-amino-5-(2-hydroxyethoxy)-4-iminocyclohexa-2,5-dien-1-ylidene]amino}-1,2-diethyl-5-(isopropylamino)-1,2-dihydro-3H-pyrazol-3-one

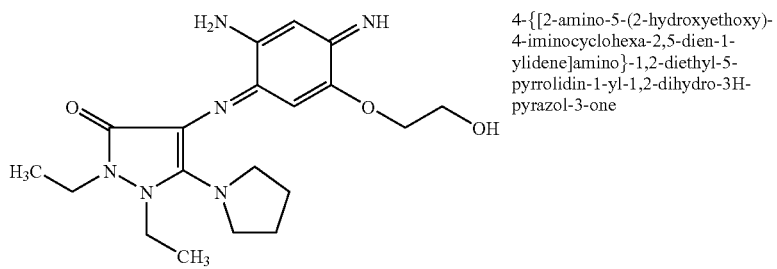

4-{[2-amino-5-(2-hydroxyethoxy)-4-iminocyclohexa-2,5-dien-1-ylidene]amino}-1,2-diethyl-5-pyrrolidin-1-yl-1,2-dihydro-3H-pyrazol-3-one

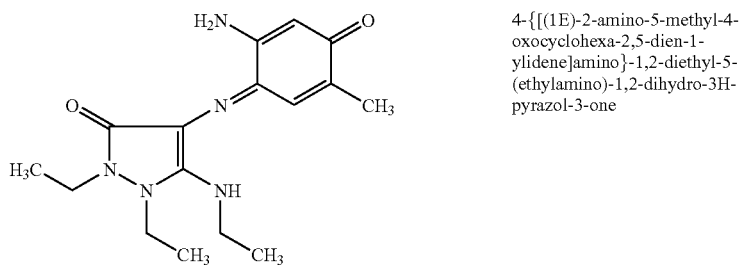

4-{[(1E)-2-amino-5-methyl-4-oxocyclohexa-2,5-dien-1-ylidene]amino}-1,2-diethyl-5-(ethylamino)-1,2-dihydro-3H-pyrazol-3-one -continued

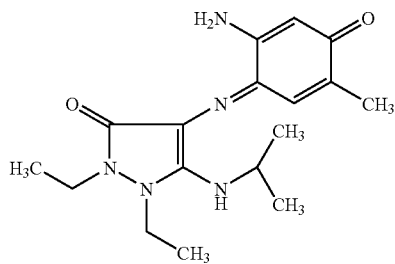

4-{[(1E)-2-amino-5-methyl-4-oxocyclohexa-2,5-dien-1-ylidene]amino}-1,2-diethyl-5-(isopropylamino)-1,2-dihydro-3H-pyrazol-3-one

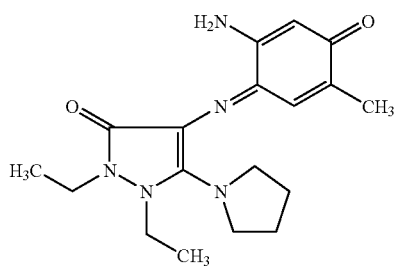

4-[(2-amino-5-methyl-4-oxocyolohexa-2,5-dien-1-ylidene)amino]-1,2-diethyl-5-pyrrolidin-1-yl-1,2-dihydro-3H-pyrazol-3-one

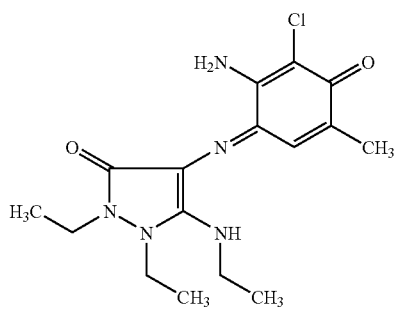

4-{[(1E)-2-amino-3-ohloro-5-methyl-4-oxocyclohexa-2,5-dien-1-ylidene]amino}-1,2-diethyl-5-(ethylamino)-1,2-dihydro-3H-pyrazol-3-one

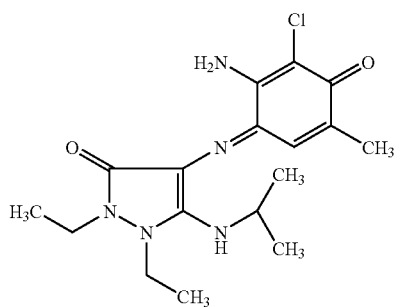

4-{[(1E)-2-amino-3-chloro-5-methyl-4-oxocyclohexa-2,5-dien-1-ylidene]amino}-1,2-diethyl-5-(isopropylamino)-1,2-dihydro-3H-pyrazol-3-one

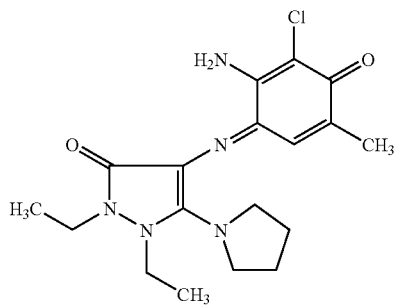

4-[(2-amino-3-chloro-5-methyl-4-oxocyclohexa-2,5-dien-1-ylidene)amino]-1,2-diethyl-5-pyrrolidin-1-yl-1,2-dihydro-3H-pyrazol-3-one -continued

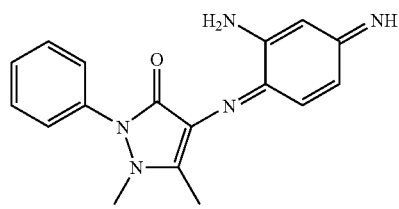
4-{[(1E)-2-amino-4-iminocyclohexa-2,5-dien-1-ylidene]amino}-1,5-dimethyl-2-phenyl-1,2-dihydro-3H-pyrazol-3-one

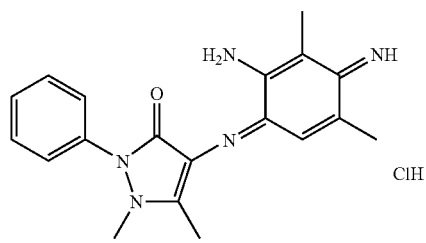
4-{[(1E)-2-amino-4-imino-3,5-dimethylcyclohexa-2,5-dien-1-ylidene]amino}-1,5-dimethyl-2-phenyl-1,2-dihydro-3H-pyrazol-3-one hydrochloride

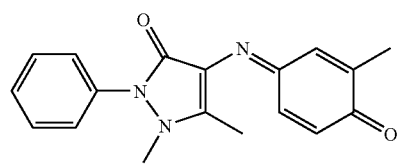
1,5-dimethyl-4-{[(1Z)-3-methyl-4-oxocyclohexa-2,5-dien-1-ylidene]amino}-2-phenyl-1,2-dihydro-3H-pyrazol-3-one

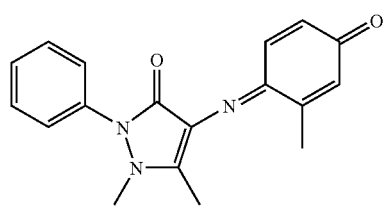
1,5-dimethyl-4-{[(1Z)-2-methyl-4-oxocyclohexa-2,5-dien-1-ylidene]amino}-2-phenyl-1,2-dihydro-3H-pyrazol-3-one

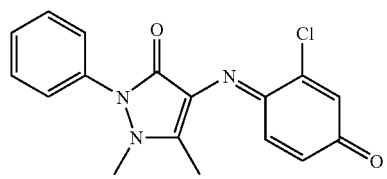
4-{[(1E)-2-chloro-4-oxocyclohexa-2,5-dien-1-ylidene]amino}-1,5-dimethyl-2-phenyl-1,2-dihydro-3H-pyrazol-3-one

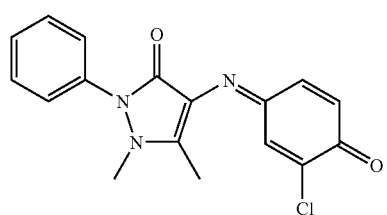
4-{[(1E)-2-chloro-4-oxocyclohexa-2,5-dien-1-ylidene]amino}-1,5-dimethyl-2-phenyl-1,2-dihydro-3H-pyrazol-3-one

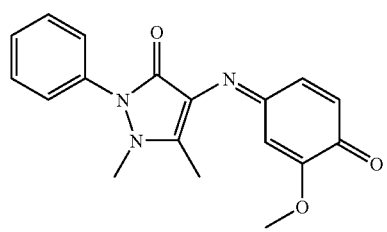
4-{[(1Z)-3-methoxy-4-oxocyclohexa-2,5-dien-1-ylidene]amino}-1,5-dimethyl-2-phenyl-1,2-dihydro-3H-pyrazol-3-one

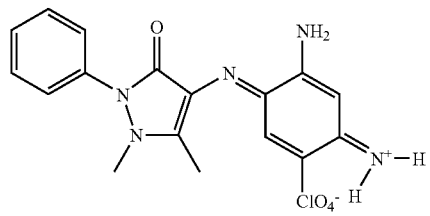

(4E)-5-amino-4-[(1,5-dimethyl-3-oxo-2-phenyl-2,3-dihydro-1H-pyrazol-4-yl)imino]-2-methylcyclohexa-2,5-dien-1-iminium perchlorate

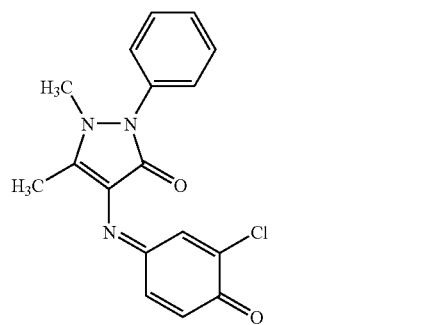

4-{[(1Z)-3-chloro-4-oxocyclohexa-2,5-dien-1-ylidene]amino}-1,5-dimethyl-2-phenyl-1,2-dihydro-3H-pyrazol-3-one and also their isomers, tautomers, solvates and acid addition salts thereof.

In at least one embodiment, the azomethine dyes with a pyrazolinone unit of formula (II) are chosen from the compounds listed below, wherein An- is as defined before:

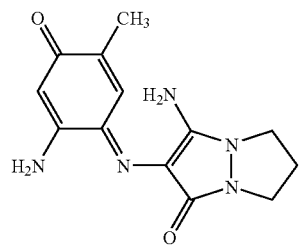

3-amino-2-{[(1E)-2-amino-5-methyl-4-oxocyclohexa-2,5-dien-1-ylidene]amino}-6,7-dihydro-1H,5H-pyrazolo[1,2-a]pyrazol-1-one

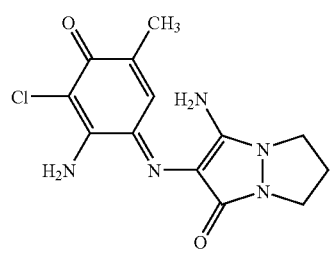

3-amino-2-{[(1E)-2-amino-3-chloro-5-methyl-4-oxocyclohexa-2,5-dien-1-ylidene]amino}-6,7-dihydro-1H,5H-pyrazolo[1,2-a]pyrazol-1-one

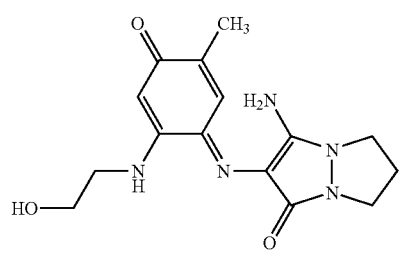

3-amino-2-({(1E)-2-[(2-hydroxyethyl)amino]-5-methyl-4-oxocyclohexa-2,5-dien-1-ylidene}amino)-6,7-dihydro-1H,5H-pyrazolo[1,2-a]pyrazol-1-one

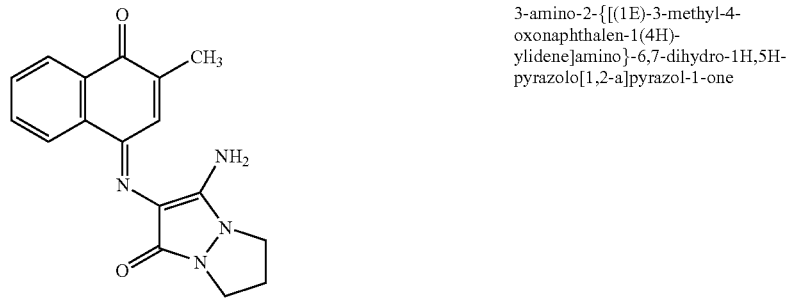

3-amino-2-{[(1E)-3-methyl-4-oxonaphthalen-1(4H)-ylidene]amino}-6,7-dihydro-1H,5H-pyrazolo[1,2-a]pyrazol-1-one

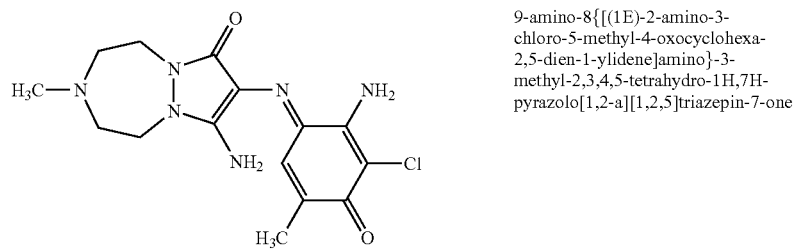

9-amino-8{[(1E)-2-amino-3-chloro-5-methyl-4-oxocyclohexa-2,5-dien-1-ylidene]amino}-3-methyl-2,3,4,5-tetrahydro-1H,7H-pyrazolo[1,2-a][1,2,5]triazepin-7-one

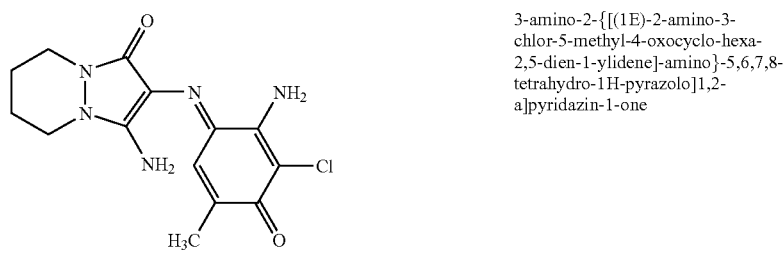

3-amino-2-{[(1E)-2-amino-3-chlor-5-methyl-4-oxocyclo-hexa-2,5-dien-1-ylidene]-amino}-5,6,7,8-tetrahydro-1H-pyrazolo]1,2-a]pyridazin-1-one

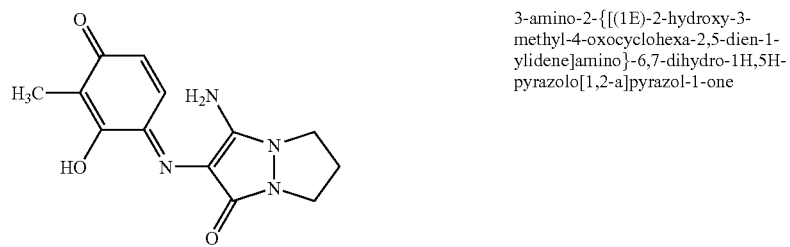

3-amino-2-{[(1E)-2-hydroxy-3-methyl-4-oxocyclohexa-2,5-dien-1-ylidene]amino}-6,7-dihydro-1H,5H-pyrazolo[1,2-a]pyrazol-1-one

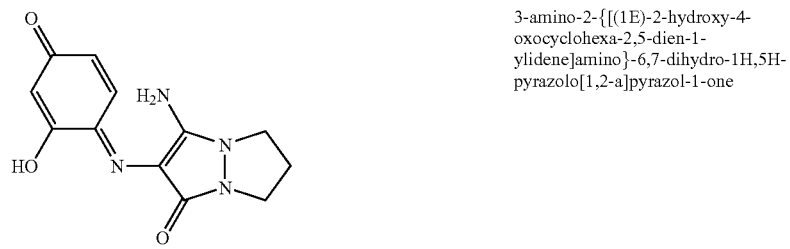

3-amino-2-{[(1E)-2-hydroxy-4-oxocyclohexa-2,5-dien-1-ylidene]amino}-6,7-dihydro-1H,5H-pyrazolo[1,2-a]pyrazol-1-one

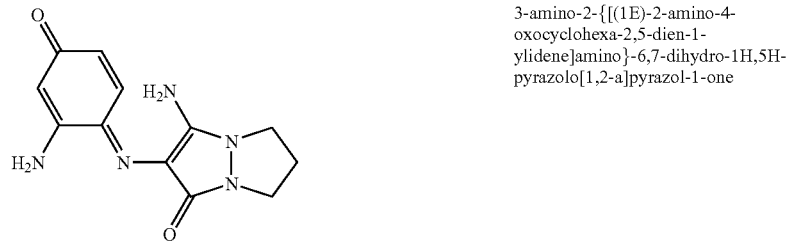

3-amino-2-{[(1E)-2-amino-4-oxocyclohexa-2,5-dien-1-ylidene]amino}-6,7-dihydro-1H,5H-pyrazolo[1,2-a]pyrazol-1-one -continued

| | |
|---|---|
|  | N-{(4E)-3-amino-4-[(1,5-dimethyl-3-oxo-2-phenyl-2,3-dihydro-1H-pyrazol-4-yl)imino]cyclohexa-2,5-dien-1-ylidene}-N-methylmethanaminium, perchlorate |
| 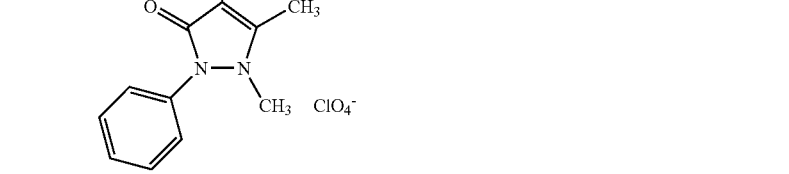 | 3-amino-2-{[(3E)-6-iminopyridin-3(6H)-ylidene]amino}-6,7-dihydro-1H,5H-pyrazolo[1,2-a]pyrazol-1-one |
| 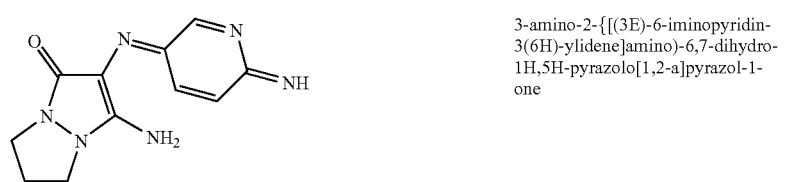 | 3-amino-2-{[(1E)-2-amino-3,5-bis(2-hydroxyethoxy)-4-oxocyclohexa-2,5-dien-1-ylidene]amino}-6,7-dihydro-1H,5H-pyrazolo[1,2-a]pyrazol-1-one |
| 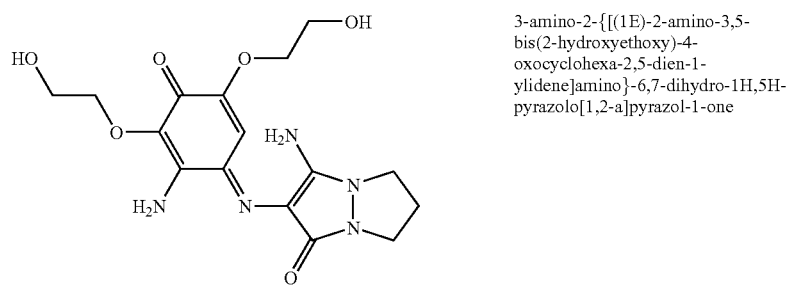 | 3-amino-2-({(1E)-2-[(2-hydroxyethyl)amino]-3,5-dimethoxy-4-oxocyclohexa-2,5-dien-1-ylidene}amino)-6,7-dihydro-1H,5H-pyrazolo[1,2-a]pyrazol-1-one |
| 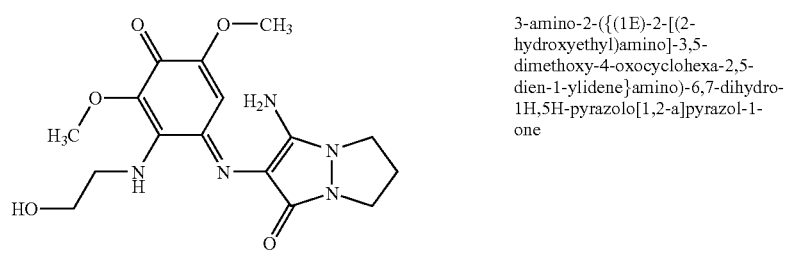 | 3-amino-2-{[(1E)-2-amino-5-methoxy-4-oxocyclohexa-2,5-dien-1-ylidene]amino}-6,7-dihydro-1H,5H-pyrazolo[1,2-a]pyrazol-1-one |
| 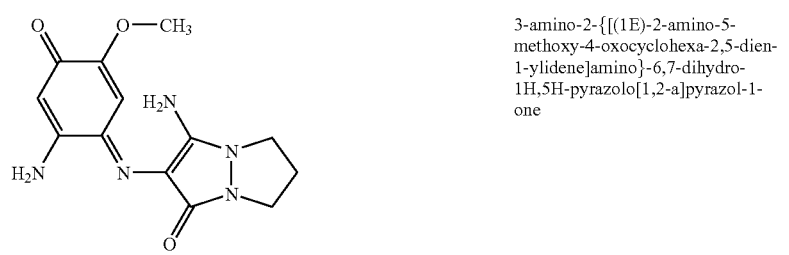 | |
| 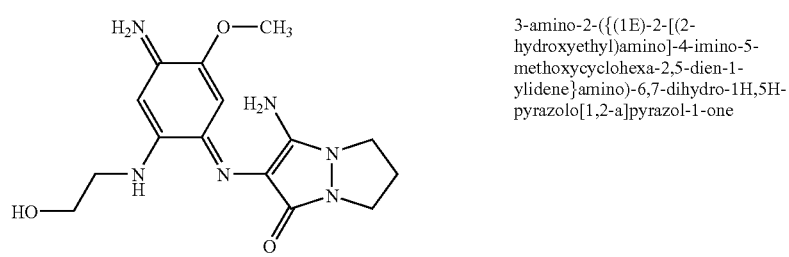 | 3-amino-2-({(1E)-2-[(2-hydroxyethyl)amino]-4-imino-5-methoxycyclohexa-2,5-dien-1-ylidene}amino)-6,7-dihydro-1H,5H-pyrazolo[1,2-a]pyrazol-1-one |

-continued

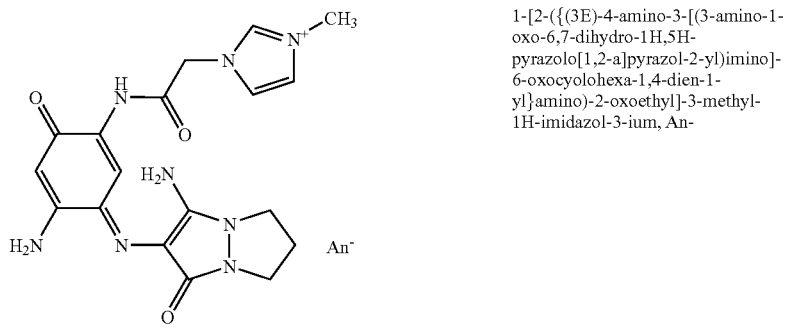

1-[2-({(3E)-4-amino-3-[(3-amino-1-oxo-6,7-dihydro-1H,5H-pyrazolo[1,2-a]pyrazol-2-yl)imino]-6-oxocyolohexa-1,4-dien-1-yl}amino)-2-oxoethyl]-3-methyl-1H-imidazol-3-ium, An-

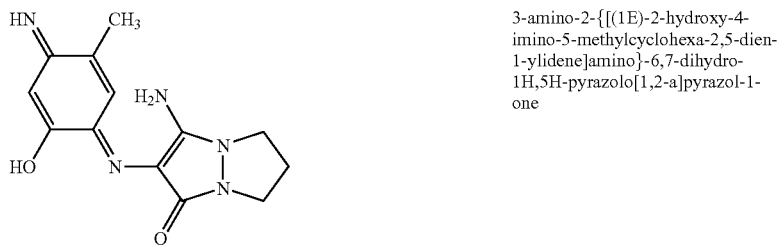

3-amino-2-{[(1E)-2-hydroxy-4-imino-5-methylcyclohexa-2,5-dien-1-ylidene]amino}-6,7-dihydro-1H,5H-pyrazolo[1,2-a]pyrazol-1-one

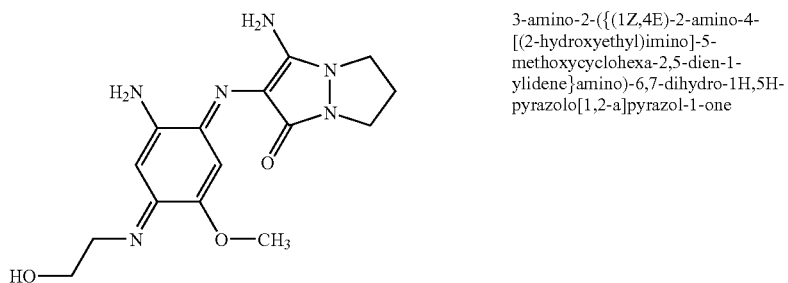

3-amino-2-({(1Z,4E)-2-amino-4-[(2-hydroxyethyl)imino]-5-methoxycyclohexa-2,5-dien-1-ylidene}amino)-6,7-dihydro-1H,5H-pyrazolo[1,2-a]pyrazol-1-one

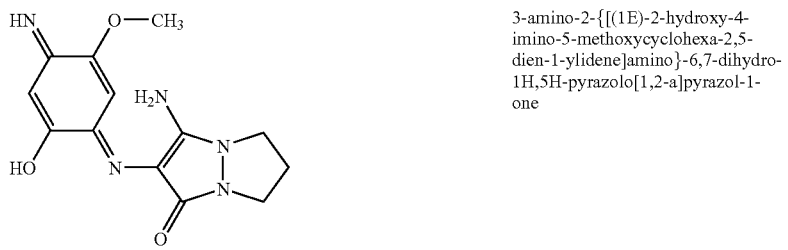

3-amino-2-{[(1E)-2-hydroxy-4-imino-5-methoxycyclohexa-2,5-dien-1-ylidene]amino}-6,7-dihydro-1H,5H-pyrazolo[1,2-a]pyrazol-1-one

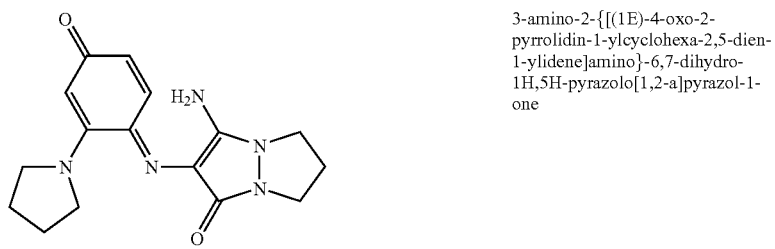

3-amino-2-{[(1E)-4-oxo-2-pyrrolidin-1-ylcyclohexa-2,5-dien-1-ylidene]amino}-6,7-dihydro-1H,5H-pyrazolo[1,2-a]pyrazol-1-one -continued

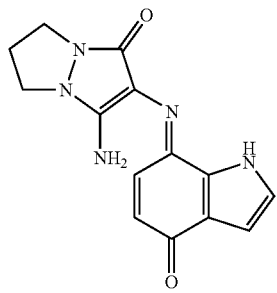

(7Z)-7-[(3-amino-1-oxo-6,7-dihydro-1H,5H-pyrazolo[1,2-a]pyrazol-2-yl) imino]-1,7-dihydro-4H-indol-4-one

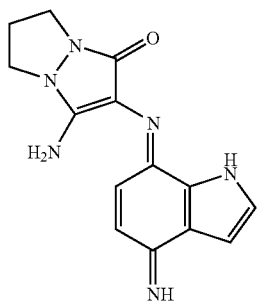

3-amino-2-{[(7E)-4-imino-1,4-dihydro-7H-indol-7-ylidene]amino}-6,7-dihydro-1H,5H-pyrazolo[1,2-a]pyrazol-1-one

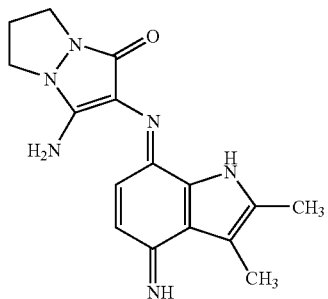

3-amino-2-{[(7E)-4-imino-2,3-dimethyl-1,4-dihydro-7H-indol-7-ylidene]amino}-6,7-dihydro-1H,5H-pyrazolo[1,2-a]pyrazol-1-one

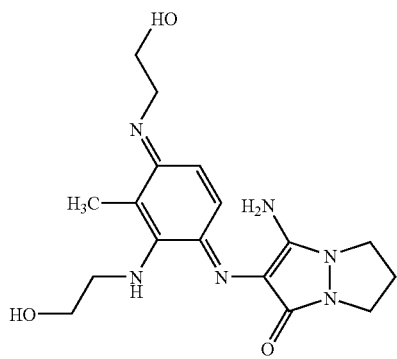

3-amino-2-({(1E,4E)-2-[(2-hydroxyethyl)amino]-4-[(2-hydroxyethyl)imino]-3-methylcyclohexa-2,5-dien-1-ylidene}amino)-6,7-dihydro-1H,5H-pyrazolo[1,2-a]pyrazol-1-one

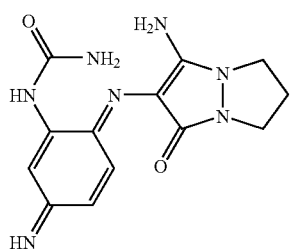

N-{(6Z)-6-[(3-amino-1-oxo-6,7-dihydro-1H,5H-pyrazolo[1,2-a]pyrazol-2-yl)imino]-3-iminocyclohexa-1,4-dien-1-yl}urea -continued

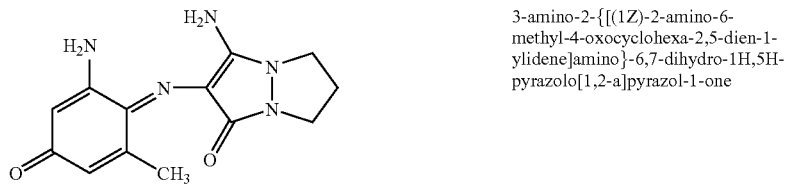 3-amino-2-{[(1Z)-2-amino-6-methyl-4-oxocyclohexa-2,5-dien-1-ylidene]amino}-6,7-dihydro-1H,5H-pyrazolo[1,2-a]pyrazol-1-one

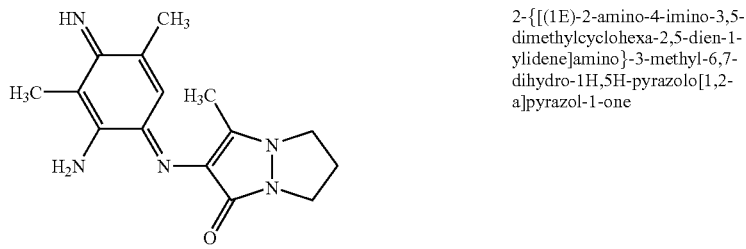 2-{[(1E)-2-amino-4-imino-3,5-dimethylcyclohexa-2,5-dien-1-ylidene]amino}-3-methyl-6,7-dihydro-1H,5H-pyrazolo[1,2-a]pyrazol-1-one

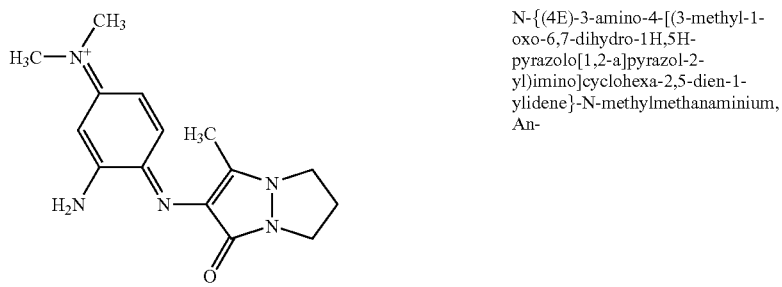 N-{(4E)-3-amino-4-[(3-methyl-1-oxo-6,7-dihydro-1H,5H-pyrazolo[1,2-a]pyrazol-2-yl)imino]cyclohexa-2,5-dien-1-ylidene}-N-methylmethanaminium, An-

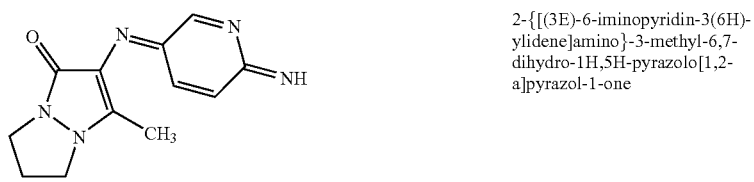 2-{[(3E)-6-iminopyridin-3(6H)-ylidene]amino}-3-methyl-6,7-dihydro-1H,5H-pyrazolo[1,2-a]pyrazol-1-one

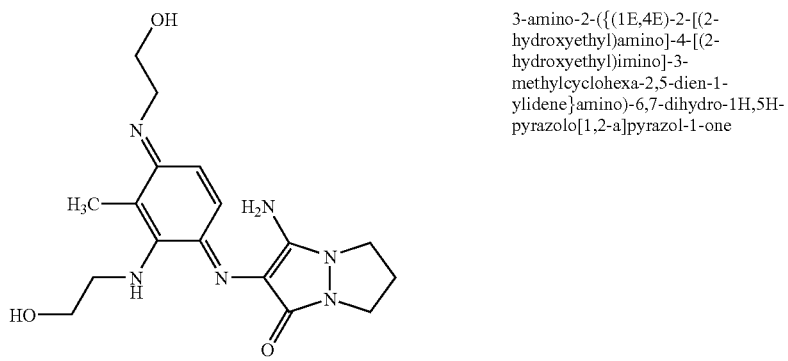 3-amino-2-({(1E,4E)-2-[(2-hydroxyethyl)amino]-4-[(2-hydroxyethyl)imino]-3-methylcyclohexa-2,5-dien-1-ylidene}amino)-6,7-dihydro-1H,5H-pyrazolo[1,2-a]pyrazol-1-one

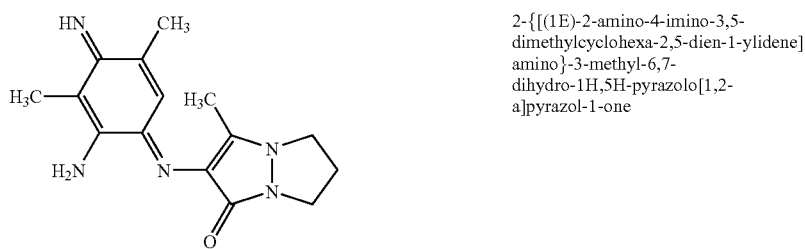 2-{[(1E)-2-amino-4-imino-3,5-dimethylcyclohexa-2,5-dien-1-ylidene]amino}-3-methyl-6,7-dihydro-1H,5H-pyrazolo[1,2-a]pyrazol-1-one -continued

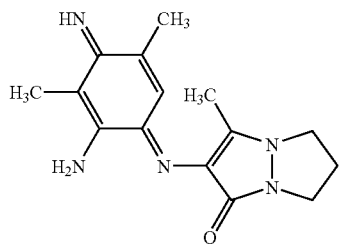

2-{[(1E)-2-amino-4-imino-3,5-dimethylcyclohexa-2,5-dien-1-ylidene]amino}-3-methyl-6,7-dihydro-1H,5H-pyrazolo[1,2-a]pyrazol-1-one

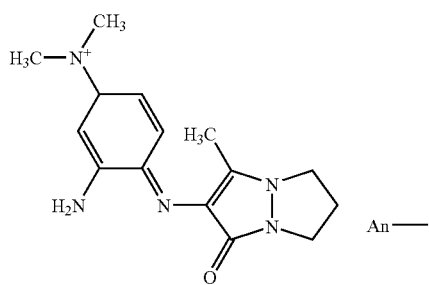

N-{(4E)-3-amino-4-[(3-methyl-1-oxo-6,7-dihydro-1H,5H-pyrazolo[1,2-a]pyrazol-2-yl)imino]cyclohexa-2,5-dien-1-ylidene}-N-methylmethanaminium, An-

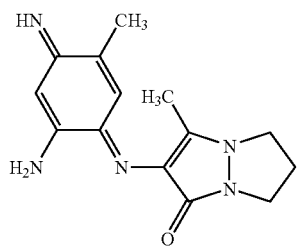

2-{[(1E)-2-amino-4-imino-5-methylcyclohexa-2,5-dien-1-ylidene]amino}-3-methyl-6,7-dihydro-1H,5H-pyrazolo[1,2-a]pyrazol-1-one

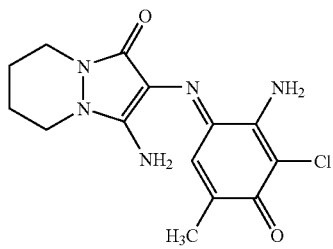

3-amino-2-{[(1E)-2-amino-3-chloro-5-methyl-4-oxocyclohexa-2,5-dien-1-ylidene]amino}-5,6,7,8-tetrahydro-1H-pyrazolo[1,2-a]pyridazin-1-one

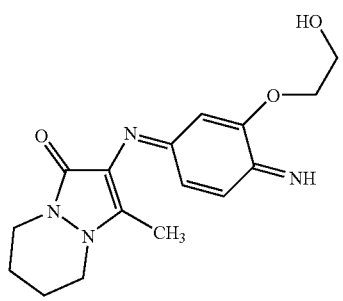

2-{[(1E)-3-(2-hydroxyethoxy)-4-iminocyclohexa-2,5-dien-1-ylidene]amino}-3-methyl-5,6,7,8-tetrahydro-1H-pyrazolo[1,2-a]pyridazin-1-one

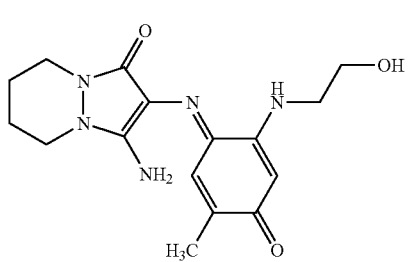

3-amino-2-({(1E)-2-[(2-hydroxyethyl)amino]-5-methyl-4-oxocyclohexa-2,5-dien-1-ylidene}amino)-5,6,7,8-tetrahydro-1H-pyrazolo[1,2-a]pyridazin-1-one -continued

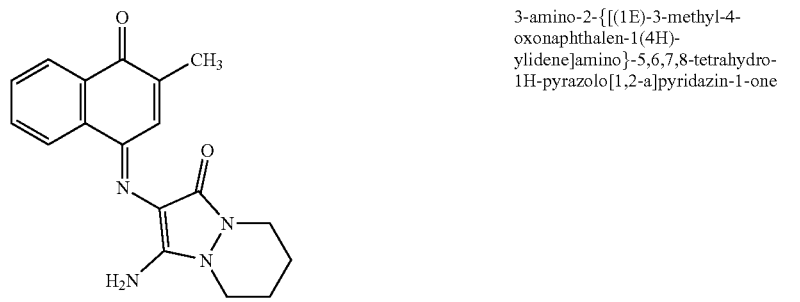 3-amino-2-{[(1E)-3-methyl-4-oxonaphthalen-1(4H)-ylidene]amino}-5,6,7,8-tetrahydro-1H-pyrazolo[1,2-a]pyridazin-1-one

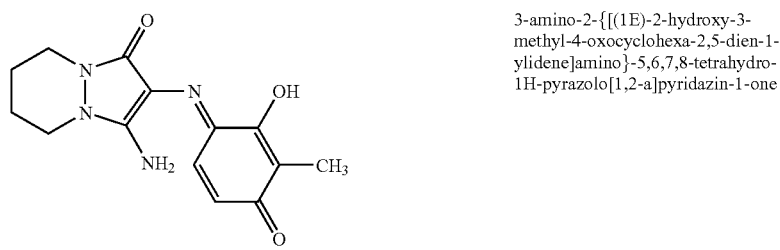 3-amino-2-{[(1E)-2-hydroxy-3-methyl-4-oxocyclohexa-2,5-dien-1-ylidene]amino}-5,6,7,8-tetrahydro-1H-pyrazolo[1,2-a]pyridazin-1-one

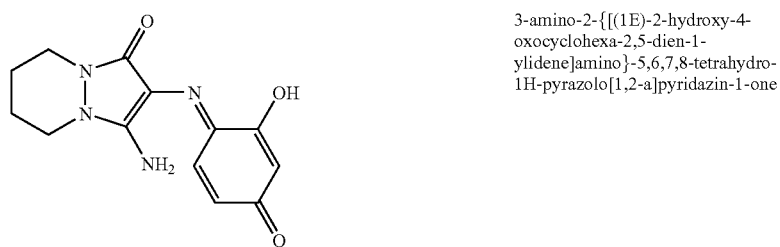 3-amino-2-{[(1E)-2-hydroxy-4-oxocyclohexa-2,5-dien-1-ylidene]amino}-5,6,7,8-tetrahydro-1H-pyrazolo[1,2-a]pyridazin-1-one

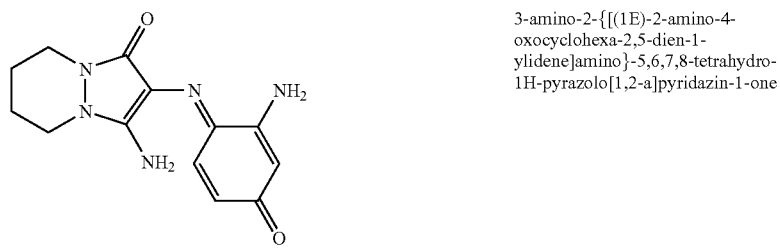 3-amino-2-{[(1E)-2-amino-4-oxocyclohexa-2,5-dien-1-ylidene]amino}-5,6,7,8-tetrahydro-1H-pyrazolo[1,2-a]pyridazin-1-one

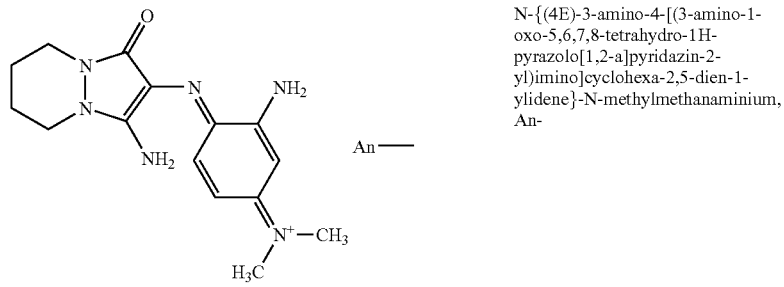 N-{(4E)-3-amino-4-[(3-amino-1-oxo-5,6,7,8-tetrahydro-1H-pyrazolo[1,2-a]pyridazin-2-yl)imino]cyclohexa-2,5-dien-1-ylidene}-N-methylmethanaminium, An-

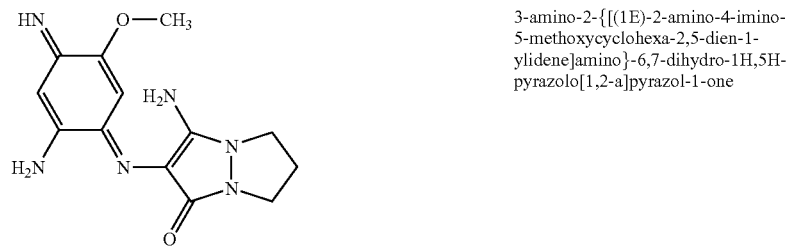 3-amino-2-{[(1E)-2-amino-4-imino-5-methoxycyclohexa-2,5-dien-1-ylidene]amino}-6,7-dihydro-1H,5H-pyrazolo[1,2-a]pyrazol-1-one -continued

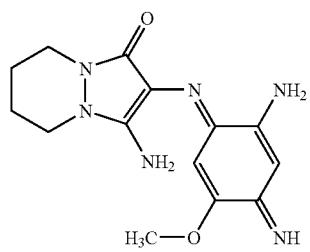
3-amino-2-{[(1E)-2-amino-4-imino-5-methoxycyclohexa-2,5-dien-1-ylidene]amino}-5,6,7,8-tetrahydro-1H-pyrazolo[1,2-a]pyridazin-1-one

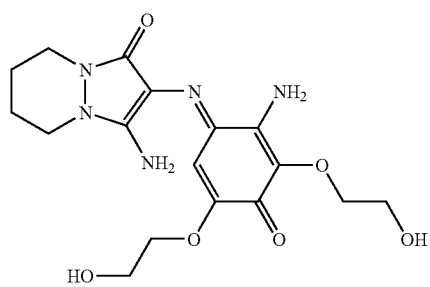
3-amino-2-{[(1E)-2-amino-3,5-bis(2-hydroxyethoxy)-4-oxocyclohexa-2,5-dien-1-ylidene]amino}-5,6,7,8-tetrahydro-1H-pyrazolo[1,2-a]pyridazin-1-one

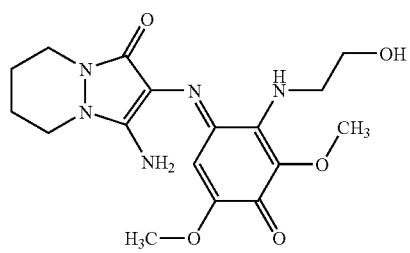
3-amino-2-({(1E)-2-[(2-hydroxyethyl)amino]-3,5-dimethoxy-4-oxocyclohexa-2,5-dien-1-ylidene}amino)-5,6,7,8-tetrahydro-1H-pyrazolo[1,2-a]pyridazin-1-one

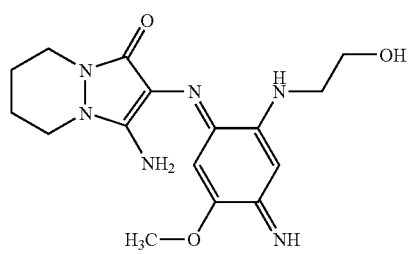
3-amino-2-({(1E)-2-[(2-hydroxyethyl)amino]-4-imino-5-methoxycyclohexa-2,5-dien-1-ylidene}amino)-5,6,7,8-tetrahydro-1H-pyrazolo[1,2-a]pyridazin-1-one

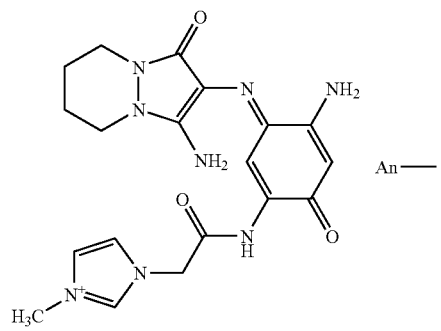
1-[2-({(3E)-4-amino-3-[(3-amino-1-oxo-5,6,7,8-tetrahydro-1H-pyrazolo[1,2-a]pyridazin-2-yl)imino]-6-oxocyclohexa-1,4-dien-1-yl}amino)-2-oxoethyl]-3-methyl-1H-imidazol-3-ium, An- -continued

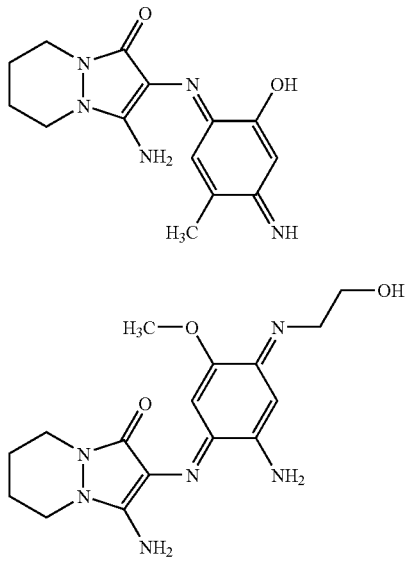
3-amino-2-{[(1E)-2-hydroxy-4-imino-5-methylcyclohexa-2,5-dien-1-ylidene]amino}-5,6,7,8-tetrahydro-1H-pyrazolo[1,2-a]pyridazin-1-one

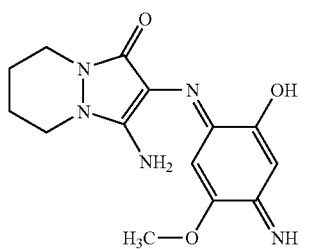
3-amino-2-({(1Z,4E)-2-amino-4-[(2-hydroxyethyl)imino]-5-methoxycyclohexa-2,5-dien-1-ylidene}amino)-5,6,7,8-tetrahydro-1H-pyrazolo[1,2-a]pyridazin-1-one

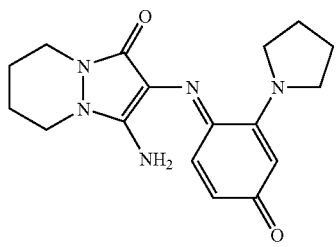
3-amino-2-{[(1E)-2-hydroxy-4-imino-5-methoxycyclohexa-2,5-dien-1-ylidene]amino}-5,6,7,8-tetrahydro-1H-pyrazolo[1,2-a]pyridazin-1-one

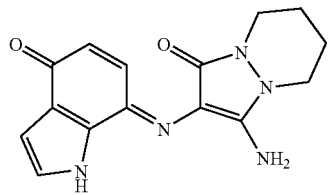
3-amino-2-{[(1E)-4-oxo-2-pyrrolidin-1-ylcyclohexa-2,5-dien-1-ylidene]amino}-5,6,7,8-tetrahydro-1H-pyrazolo[1,2-a]pyridazin-1-one

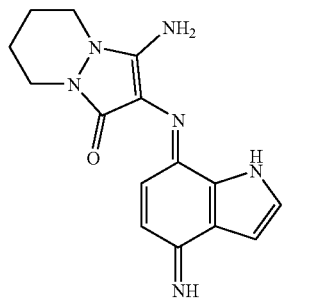
3-amino-2-{[(7Z)-4-oxo-1,4-dihydro-7H-indol-7-ylidene]amino}-5,6,7,8-tetrahydro-1H-pyrazolol[1,2-a]pyridazin-1-one 3-amino-2-{[(7E)-4-imino-1,4-dihydro-7H-indol-7-ylidene]amino}-5,6,7,8-tetrahydro-1H-pyrazolo[1,2-a]pyridazin-1-one -continued

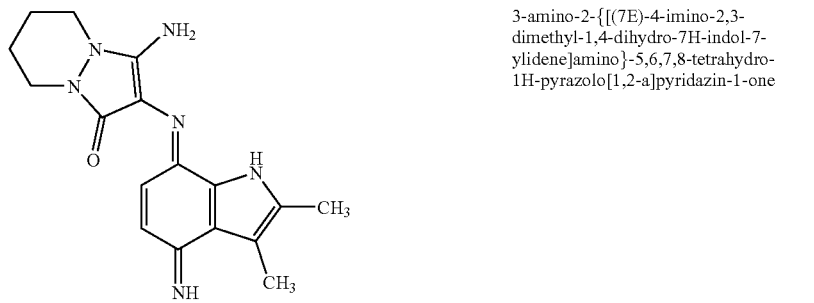

3-amino-2-{[(7E)-4-imino-2,3-dimethyl-1,4-dihydro-7H-indol-7-ylidene]amino}-5,6,7,8-tetrahydro-1H-pyrazolo[1,2-a]pyridazin-1-one

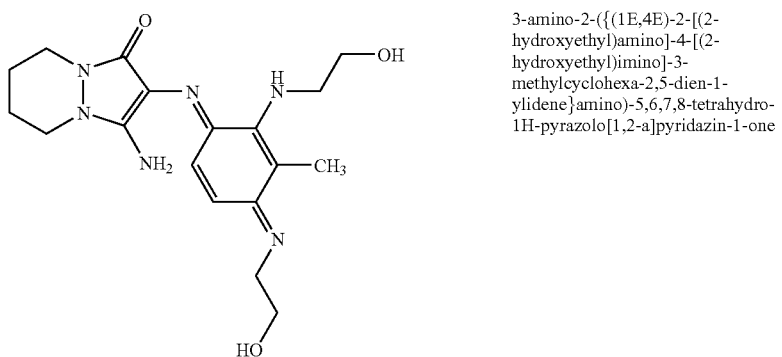

3-amino-2-({(1E,4E)-2-[(2-hydroxyethyl)amino]-4-[(2-hydroxyethyl)imino]-3-methylcyclohexa-2,5-dien-1-ylidene}amino)-5,6,7,8-tetrahydro-1H-pyrazolo[1,2-a]pyridazin-1-one

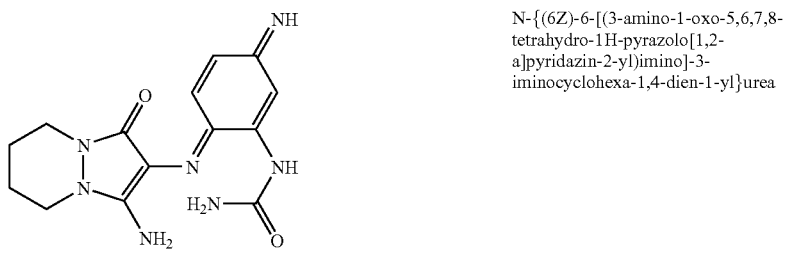

N-{(6Z)-6-[(3-amino-1-oxo-5,6,7,8-tetrahydro-1H-pyrazolo[1,2-a]pyridazin-2-yl)imino]-3-iminocyclohexa-1,4-dien-1-yl}urea

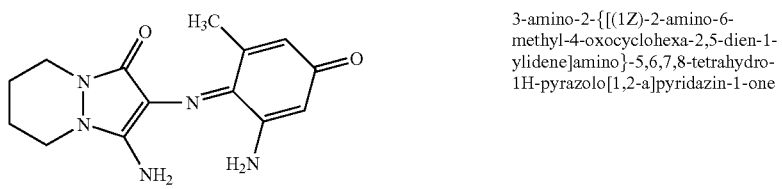

3-amino-2-{[(1Z)-2-amino-6-methyl-4-oxocyclohexa-2,5-dien-1-ylidene]amino}-5,6,7,8-tetrahydro-1H-pyrazolo[1,2-a]pyridazin-1-one

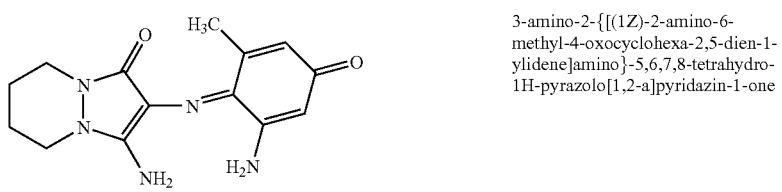

3-amino-2-{[(1Z)-2-amino-6-methyl-4-oxocyclohexa-2,5-dien-1-ylidene]amino}-5,6,7,8-tetrahydro-1H-pyrazolo[1,2-a]pyridazin-1-one

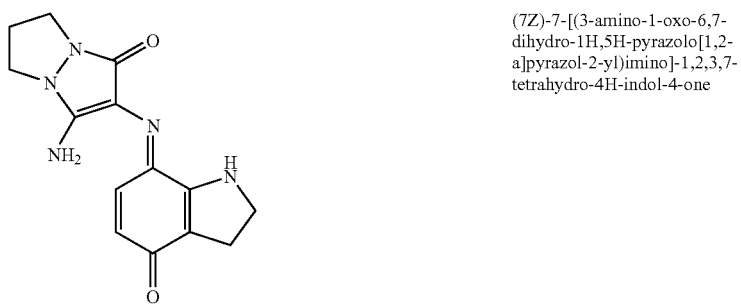

(7Z)-7-[(3-amino-1-oxo-6,7-dihydro-1H,5H-pyrazolo[1,2-a]pyrazol-2-yl)imino]-1,2,3,7-tetrahydro-4H-indol-4-one

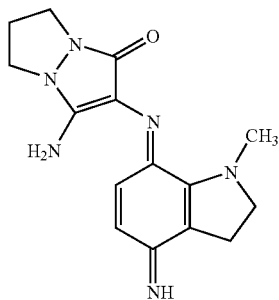

3-amino-2-{[(7E)-4-imino-1-methyl-1,2,3,4-tetrahydro-7H-indol-7-ylidene]amino}-6,7-dihydro-1H,5H-pyrazolo[1,2-a]pyrazol-1-one

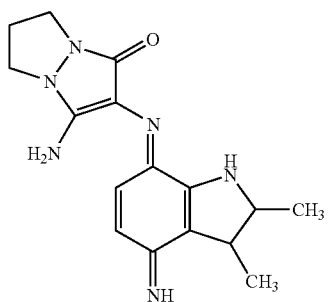

3-amino-2-{[(7E)-4-imino-2,3-dimethyl-1,2,3,4-tetrahydro-7H-indol-7-ylidene]amino}-6,7-dihydro-1H,5H-pyrazolo[1,2-a]pyrazol-1-one

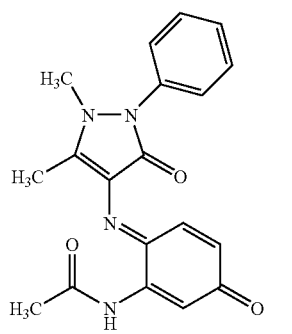

N-{(6E)-6-[(1,5-dimethyl-3-oxo-2-phenyl-2,3-dihydro-1H-pyrazol-4-yl)imino]-3-oxocyclohexa-1,4-dien-1-yl}acetamide

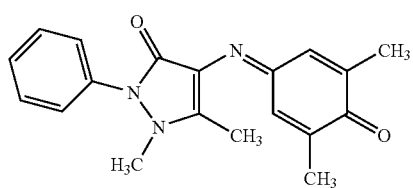

4-[(3,5-dimethyl-4-oxocyclohexa-2,5-dien-1-ylidene)amino]-1,5-dimethyl-2-phenyl-1,2-dihydro-3H-pyrazol-3-one

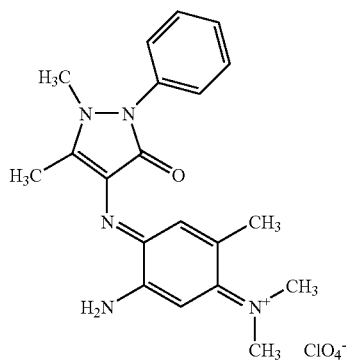

N-{(4E)-5-amino-4-[(1,5-dimethyl-3-oxo-2-phenyl-2,3-dihydro-1H-pyrazol-4-yl)imino]-2-methylcyclohexa-2,5-dien-1-ylidene}-N-methylmethanaminium, perchlorate

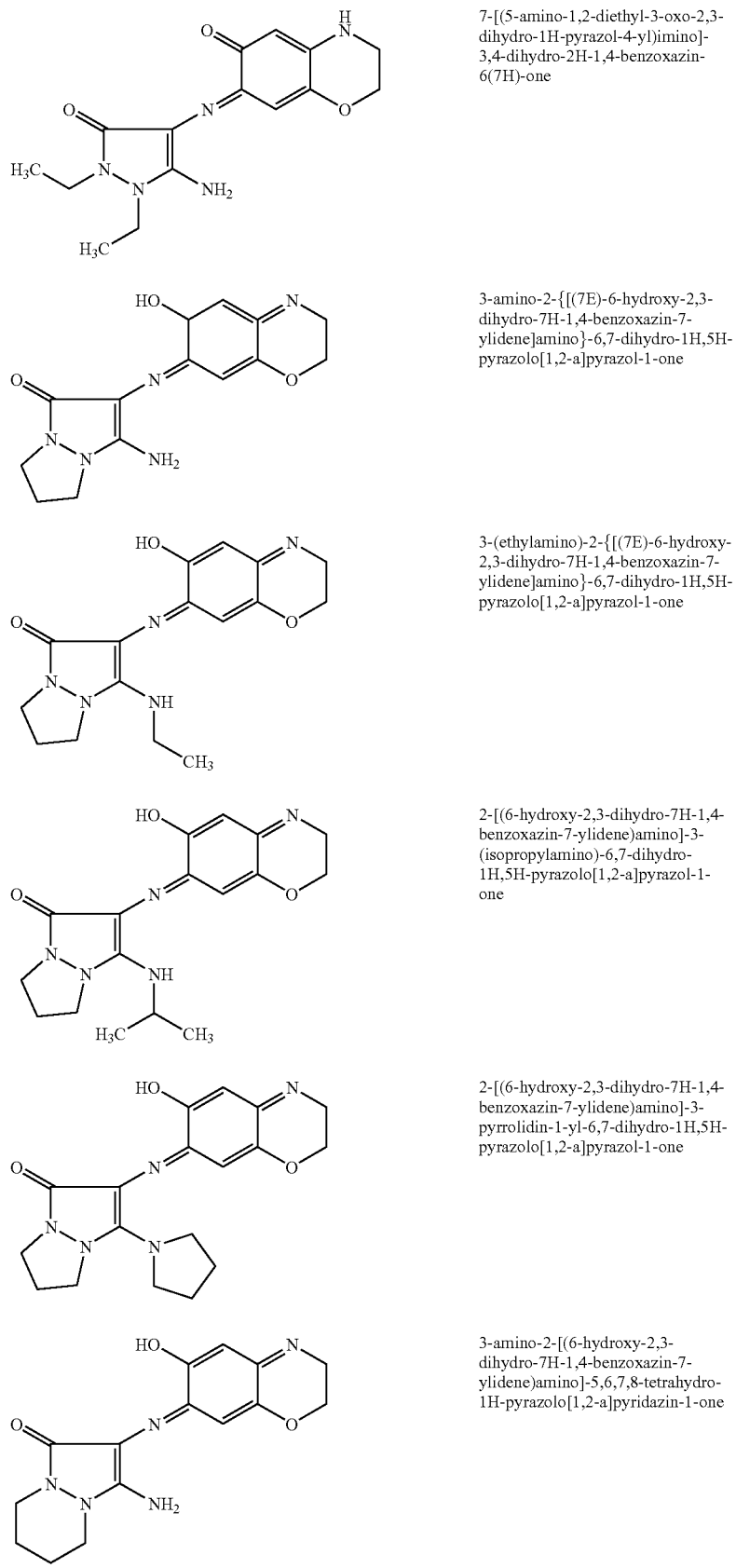

7-[(5-amino-1,2-diethyl-3-oxo-2,3-dihydro-1H-pyrazol-4-yl)imino]-3,4-dihydro-2H-1,4-benzoxazin-6(7H)-one 3-amino-2-{[(7E)-6-hydroxy-2,3-dihydro-7H-1,4-benzoxazin-7-ylidene]amino}-6,7-dihydro-1H,5H-pyrazolo[1,2-a]pyrazol-1-one 3-(ethylamino)-2-{[(7E)-6-hydroxy-2,3-dihydro-7H-1,4-benzoxazin-7-ylidene]amino}-6,7-dihydro-1H,5H-pyrazolo[1,2-a]pyrazol-1-one 2-[(6-hydroxy-2,3-dihydro-7H-1,4-benzoxazin-7-ylidene)amino]-3-(isopropylamino)-6,7-dihydro-1H,5H-pyrazolo[1,2-a]pyrazol-1-one 2-[(6-hydroxy-2,3-dihydro-7H-1,4-benzoxazin-7-ylidene)amino]-3-pyrrolidin-1-yl-6,7-dihydro-1H,5H-pyrazolo[1,2-a]pyrazol-1-one 3-amino-2-[(6-hydroxy-2,3-dihydro-7H-1,4-benzoxazin-7-ylidene)amino]-5,6,7,8-tetrahydro-1H-pyrazolo[1,2-a]pyridazin-1-one -continued

| | |
|---|---|
| 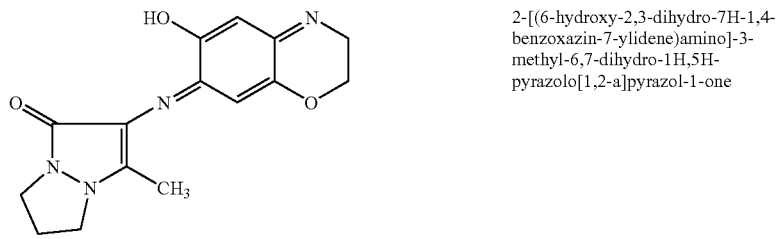 | 2-[(6-hydroxy-2,3-dihydro-7H-1,4-benzoxazin-7-ylidene)amino]-3-methyl-6,7-dihydro-1H,5H-pyrazolo[1,2-a]pyrazol-1-one |
| 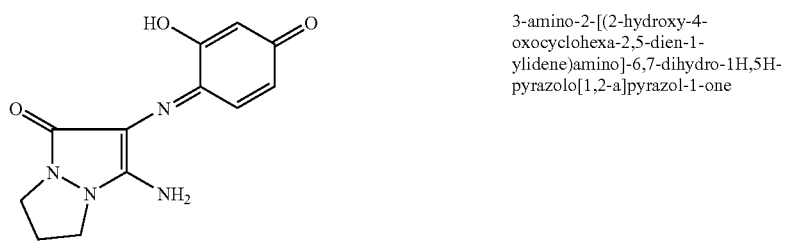 | 3-amino-2-[(2-hydroxy-4-oxocyclohexa-2,5-dien-1-ylidene)amino]-6,7-dihydro-1H,5H-pyrazolo[1,2-a]pyrazol-1-one |
| 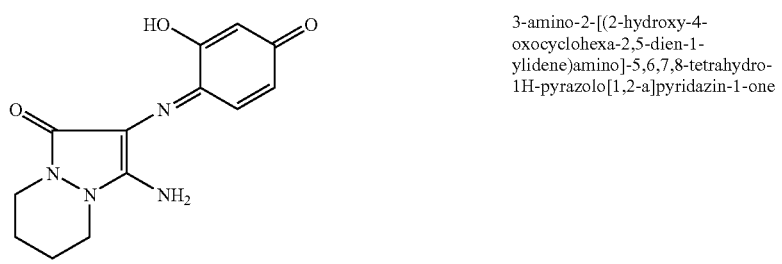 | 3-amino-2-[(2-hydroxy-4-oxocyclohexa-2,5-dien-1-ylidene)amino]-5,6,7,8-tetrahydro-1H-pyrazolo[1,2-a]pyridazin-1-one |
| 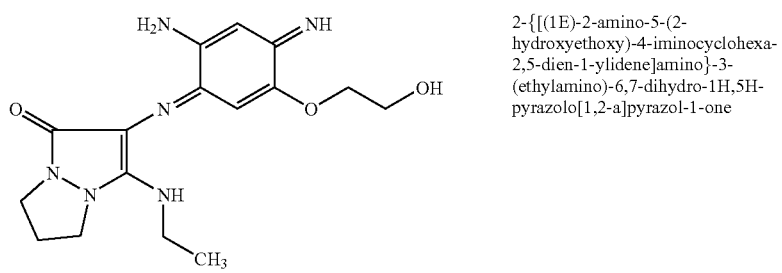 | 2-{[(1E)-2-amino-5-(2-hydroxyethoxy)-4-iminocyclohexa-2,5-dien-1-ylidene]amino}-3-(ethylamino)-6,7-dihydro-1H,5H-pyrazolo[1,2-a]pyrazol-1-one |
| 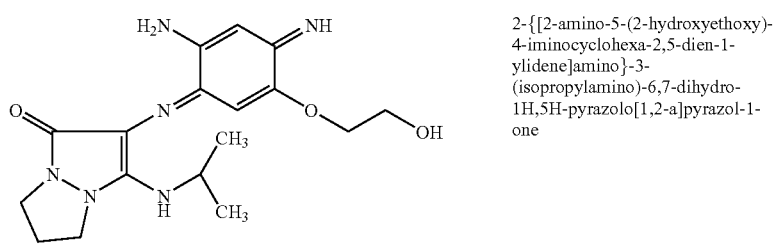 | 2-{[2-amino-5-(2-hydroxyethoxy)-4-iminocyclohexa-2,5-dien-1-ylidene]amino}-3-(isopropylamino)-6,7-dihydro-1H,5H-pyrazolo[1,2-a]pyrazol-1-one |
| 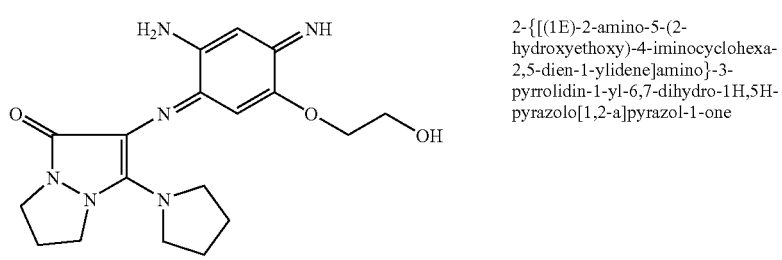 | 2-{[(1E)-2-amino-5-(2-hydroxyethoxy)-4-iminocyclohexa-2,5-dien-1-ylidene]amino}-3-pyrrolidin-1-yl-6,7-dihydro-1H,5H-pyrazolo[1,2-a]pyrazol-1-one |

-continued

| | |
|---|---|
| 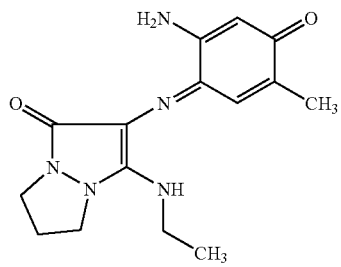 | 2-[(2-amino-5-methyl-4-oxocyclohexa-2,5-dien-1-ylidene)amino]-3-(ethylamino)-6,7-dihydro-1H,5H-pyrazolo[1,2-a]pyrazol-1-one |
| 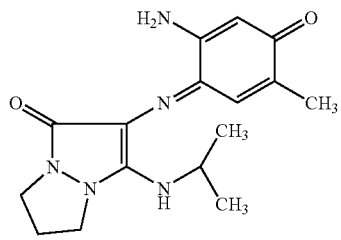 | 2-[(2-amino-5-methyl-4-oxocyclohexa-2,5-dien-1-ylidene)amino]-3-(isopropylamino)-6,7-dihydro-1H,5H-pyrazolo[1,2-a]pyrazol-1-one |
| 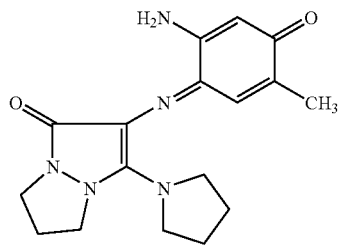 | 2-[(2-amino-5-methyl-4-oxocyclohexa-2,5-dien-1-ylidene)amino]-3-pyrrolidin-1-yl-6,7-dihydro-1H,5H-pyrazolo[1,2-a]pyrazol-1-one |
| 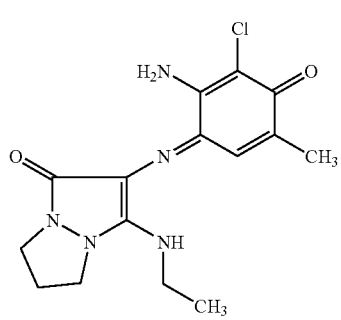 | 2-[(2-amino-3-chloro-5-methyl-4-oxocyclohexa-2,5-dien-1-ylidene)amino]-3-(ethylamino)-6,7-dihydro-1H,5H-pyrazolo[1,2-a]pyrazol-1-one |
| 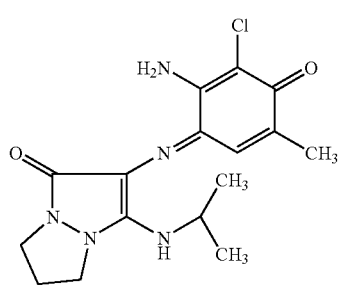 | 2-[(2-amino-3-chloro-5-methyl-4-oxocyclohexa-2,5-dien-1-ylidene)amino]-3-(isopropylamino)-6,7-dihydro-1H,5H-pyrazolo[1,2-a]pyrazol-1-one |

| | |
|---|---|
| 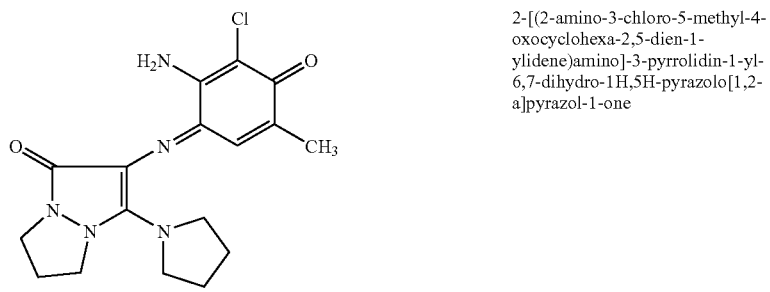 | 2-[(2-amino-3-chloro-5-methyl-4-oxocyclohexa-2,5-dien-1-ylidene)amino]-3-pyrrolidin-1-yl-6,7-dihydro-1H,5H-pyrazolo[1,2-a]pyrazol-1-one |
| 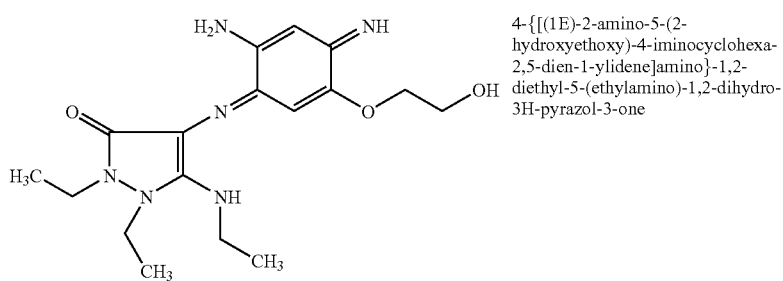 | 4-{[(1E)-2-amino-5-(2-hydroxyethoxy)-4-iminocyclohexa-2,5-dien-1-ylidene]amino}-1,2-diethyl-5-(ethylamino)-1,2-dihydro-3H-pyrazol-3-one |
| 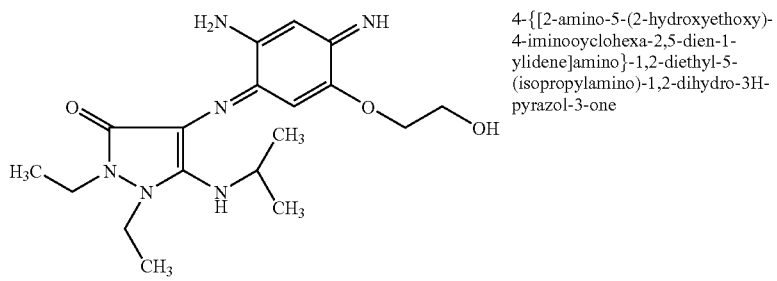 | 4-{[2-amino-5-(2-hydroxyethoxy)-4-iminocyclohexa-2,5-dien-1-ylidene]amino}-1,2-diethyl-5-(isopropylamino)-1,2-dihydro-3H-pyrazol-3-one |
| 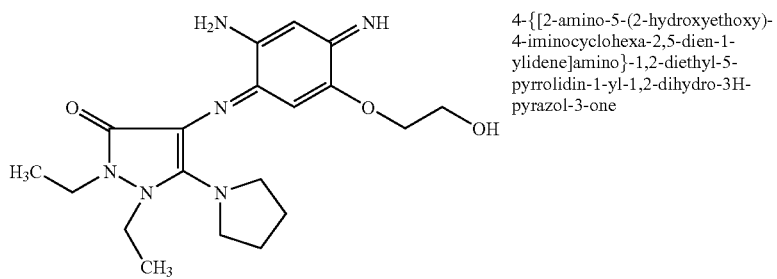 | 4-{[2-amino-5-(2-hydroxyethoxy)-4-iminocyclohexa-2,5-dien-1-ylidene]amino}-1,2-diethyl-5-pyrrolidin-1-yl-1,2-dihydro-3H-pyrazol-3-one |
| 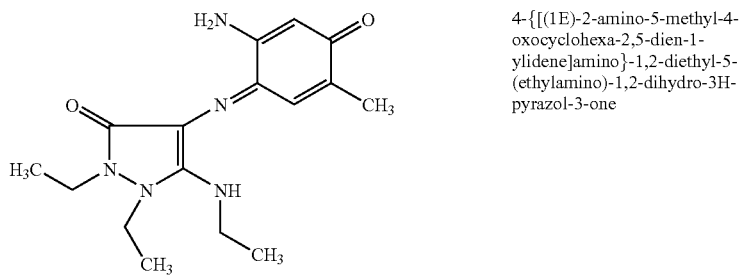 | 4-{[(1E)-2-amino-5-methyl-4-oxocyclohexa-2,5-dien-1-ylidene]amino}-1,2-diethyl-5-(ethylamino)-1,2-dihydro-3H-pyrazol-3-one |

-continued

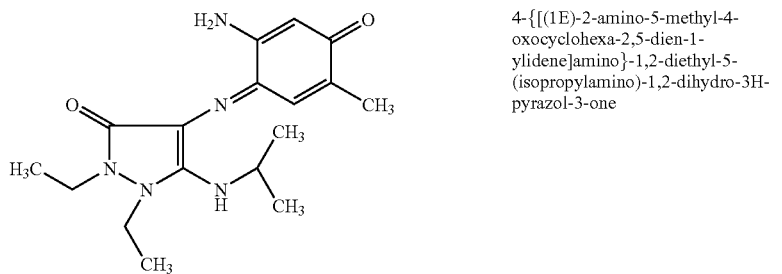

4-{[(1E)-2-amino-5-methyl-4-oxocyclohexa-2,5-dien-1-ylidene]amino}-1,2-diethyl-5-(isopropylamino)-1,2-dihydro-3H-pyrazol-3-one

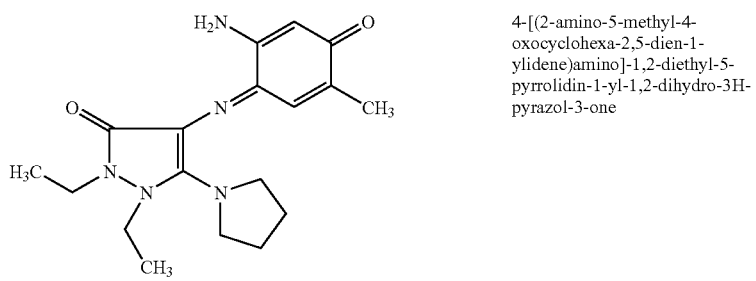

4-[(2-amino-5-methyl-4-oxocyclohexa-2,5-dien-1-ylidene)amino]-1,2-diethyl-5-pyrrolidin-1-yl-1,2-dihydro-3H-pyrazol-3-one

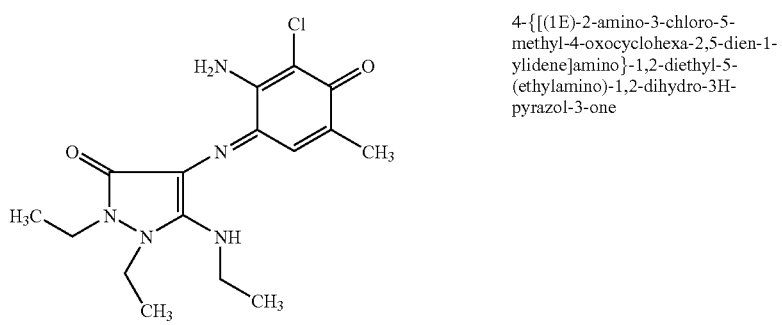

4-{[(1E)-2-amino-3-chloro-5-methyl-4-oxocyclohexa-2,5-dien-1-ylidene]amino}-1,2-diethyl-5-(ethylamino)-1,2-dihydro-3H-pyrazol-3-one

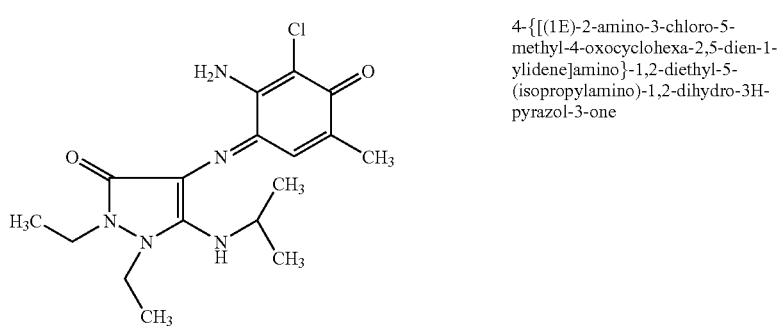

4-{[(1E)-2-amino-3-chloro-5-methyl-4-oxocyclohexa-2,5-dien-1-ylidene]amino}-1,2-diethyl-5-(isopropylamino)-1,2-dihydro-3H-pyrazol-3-one

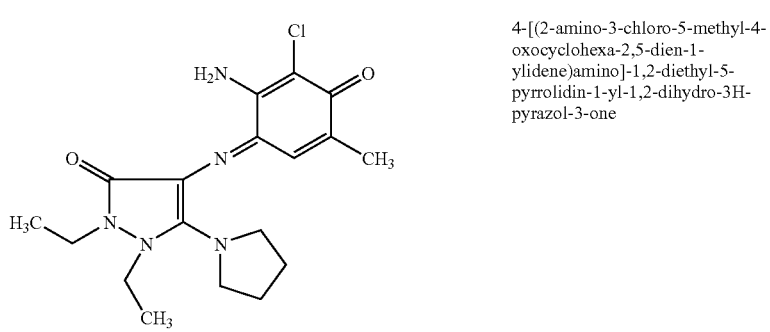

4-[(2-amino-3-chloro-5-methyl-4-oxocyclohexa-2,5-dien-1-ylidene)amino]-1,2-diethyl-5-pyrrolidin-1-yl-1,2-dihydro-3H-pyrazol-3-one -continued

| | |
|---|---|
| 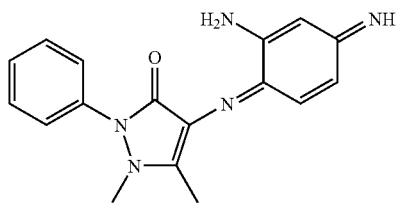 | 4-{[(1E)-2-amino-4-iminocyclohexa-2,5-dien-1-ylidene]amino}-1,5-dimethyl-2-phenyl-1,2-dihydro-3H-pyrazol-3-one |
| 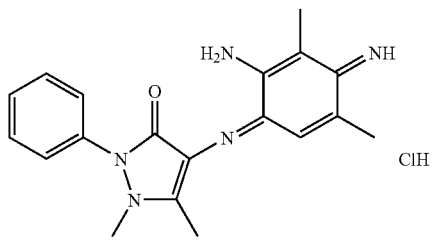 | 4-{[(1E)-2-amino-4-imino-3,5-dimethylcyclohexa-2,5-dien-1-ylidene]amino}-1,5-dimethyl-2-phenyl-1,2-dihydro-3H-pyrazol-3-one hydrochloride |
| 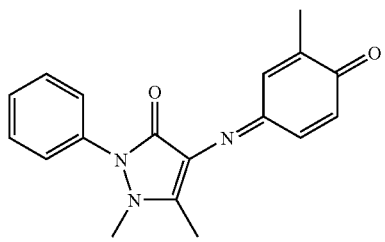 | 1,5-dimethyl-4-{[(1Z)-3-methyl-4-oxocyclohexa-2,5-dien-1-ylidene]amino}-2-phenyl-1,2-dihydro-3H-pyrazol-3-one |
| 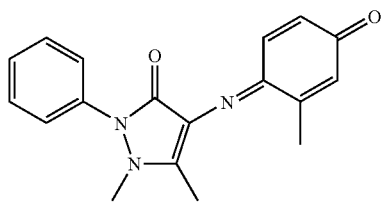 | 1,5-dimethyl-4-{[(1Z)-2-methyl-4-oxocyclohexa-2,5-dien-1-ylidene]amino}-2-phenyl-1,2-dihydro-3H-pyrazol-3-one |
| 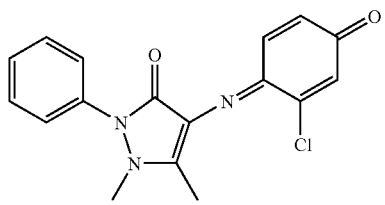 | 4-{[(1E)-2-chloro-4-oxocyclohexa-2,5-dien-1-ylidene]amino}-1,5-dimethyl-2-phenyl-1,2-dihydro-3H-pyrazol-3-one |
| 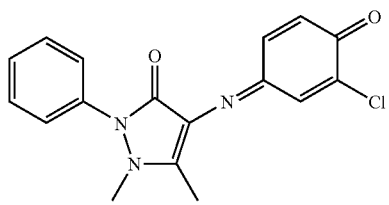 | 4-{[(1E)-2-chloro-4-oxocyclohexa-2,5-dien-1-ylidene]amino}-1,5-dimethyl-2-phenyl-1,2-dihydro-3H-pyrazol-3-one |
| 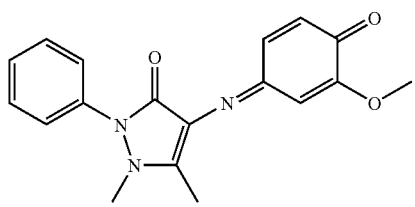 | 4-{[(1Z)-3-methoxy-4-oxocyclohexa-2,5-dien-1-ylidene]amino}-1,5-dimethyl-2-phenyl-1,2-dihydro-3H-pyrazol-3-one |

-continued

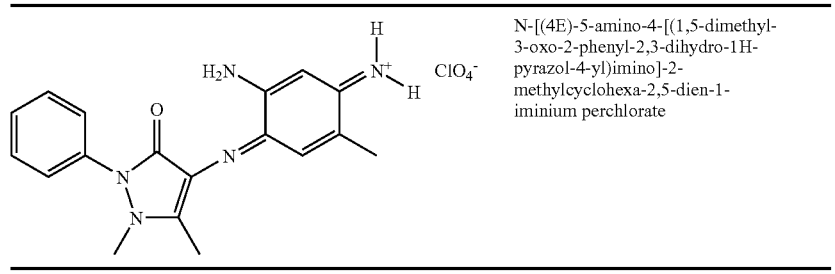

N-[(4E)-5-amino-4-[(1,5-dimethyl-3-oxo-2-phenyl-2,3-dihydro-1H-pyrazol-4-yl)imino]-2-methylcyclohexa-2,5-dien-1-iminium perchlorate and their isomers, tautomers, solvates and addition salts thereof.

The leuco compounds of formula (I) and the azomethine dyes with a pyrazolinone unit of formula (II), as disclosed herein, may be prepared, for example, by the method of synthesis as described in:

Journal of Organic Chemistry, 50(17), 3091-4; 1985;
Journal fuer Praktische Chemie (Leipzig), 322(4), 674-8; 1980; and
Chemische Berichte, 113(2). 457-70; 1980.

The compounds of formula (I) and/or (II) may be obtained by one of the procedures below:

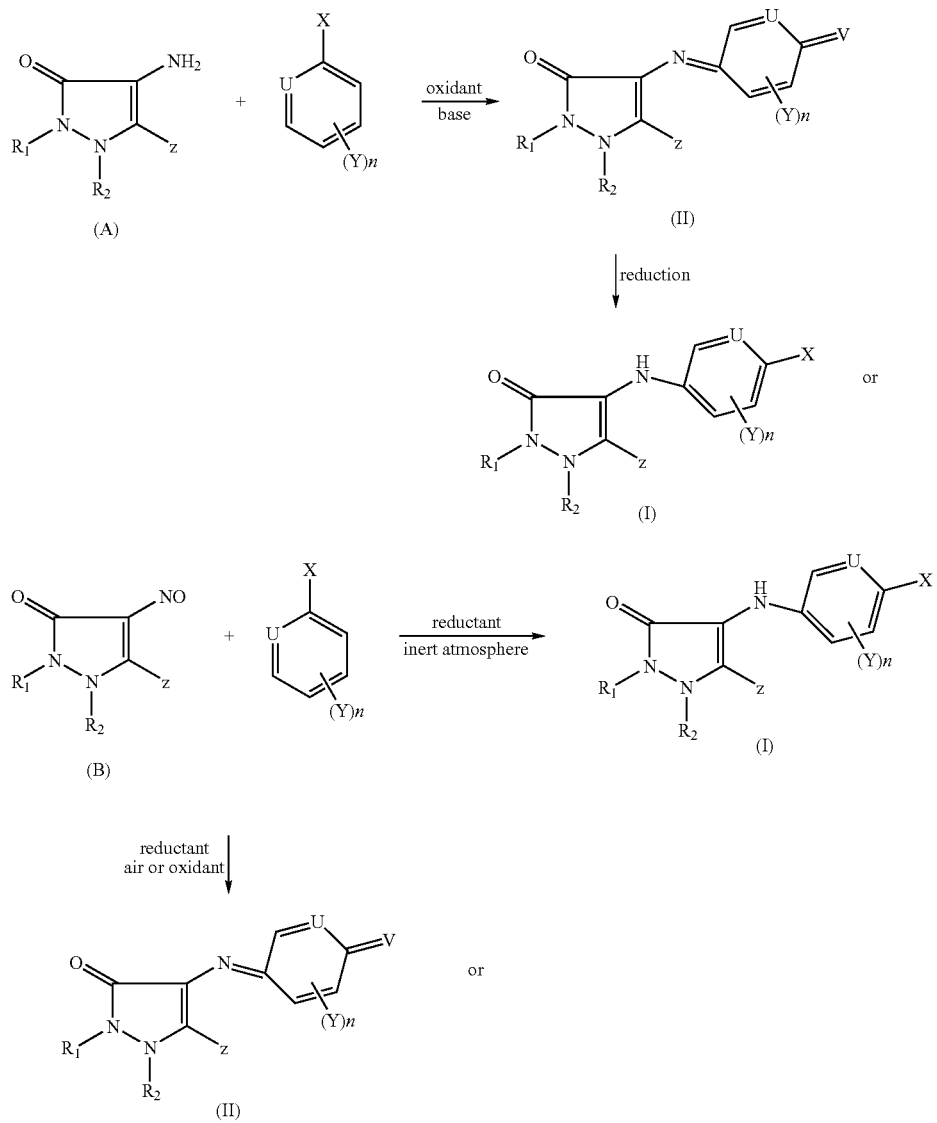

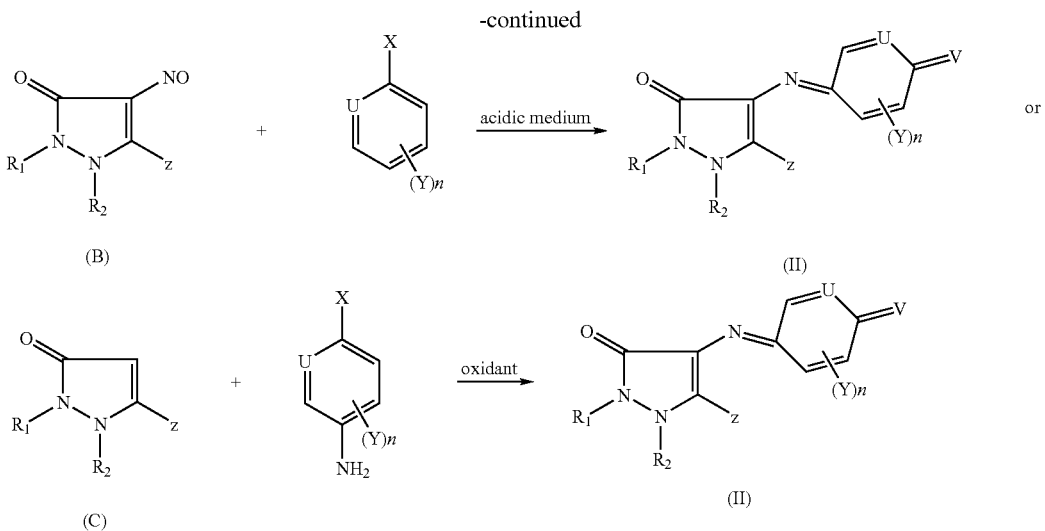

The reactions are generally conducted in water or an ethanol/water mixture or even in ethanol at a temperature ranging from 0° C. to 80° C.

When a reductant is employed, it is generally used in excess and may be chosen, by way of non-limiting example, from Zn, $SnCl_2$, and sodium dithionite ($Na_2S_2O_4$).

When the reaction requires the presence of at least one oxidant, the oxidant is used generally in excess and may be chosen, by way of non-limiting example, from air, hydrogen peroxide, ferric chloride, potassium or sodium ferricyanide ($FeCN_6K_3$ or $FeCN_6Na_3$), sodium perchlorate ($NaClO_4$), sodium or potassium persulfate ($Na_2S_2O_8$ or $K_2S_2O_8$) and manganese dioxide $MnO_2$.

When the reaction is performed in an acidic medium, the medium is generally an organic acid or mineral acid such as, by way of non-limitign example, hydrochloric acid, hydrobromic acid, acetic acid, formic acid, and trifluoroacetic acid.

When the reaction is performed in a basic medium, the base is generally a mineral base such as, by way of non-limiting example, aqueous ammonia, sodium hydroxide solution, and potassium hydroxide solution.

The compounds of formula (A), (B) and (C) are described, for example, in European Patent Application No. EP 1 764 082.

The at least one compound chosen from leuco compounds of formula (I) and azomethine dyes with a pyrazolinone unit of formula (II) is present in an amount ranging from 0.01% to 15% by weight, for example from 0.05% to 10% by weight, relative to the total weight of the composition.

The dyeing composition in accordance with the present disclosure may also comprise at least one oxidation base. The at least one oxidation base may be chosen from oxidation bases conventionally used in oxidation dyeing, for example, para-phenylenediamines, bisphenylalkylenediamines, para-aminophenols, ortho-aminophenols and heterocyclic bases.

Non-limiting mention may be made of para-phenylenediamines, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxy-ethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and acid addition salts thereof.

In at least one embodiment, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and acid addition salts thereof may be used.

Non-limiting mention may be made of bisphenylalkylenediamines, for example, N,N'-bis(β-hydroxyethyl)-N,N'-bis (4'-aminophenyl)-1,3-diaminopropanol, N,N'-bis(β-hydroxyethyl)-N,N'-bis(4'-aminophenyl)ethylene-diamine, N,N'-bis(4-amino-phenyl)tetramethylenediamine, N,N'-bis (β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and acid addition salts thereof.

Non-limiting mention may be made of para-aminophenols, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and acid addition salts thereof.

Non-limiting mention may be made of ortho-aminophenols, for example, 2-aminophenol, 2-amino-5-methylphenol, 2-amino-6-methylphenol and 5-acetamido-2-aminophenol, and addition salts thereof.

Non-limiting mention may be made of heterocyclic bases, for example, pyridine derivatives, pyrimidine derivatives and pyrazole derivatives, and pyrazolo[1,2a]pyrazol-1-one derivatives.

Examples of pyridine derivatives include, but are not limited to, the compounds described in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diamino-pyridine, and acid addition salts thereof.

Examples of pyrimidine derivatives include, but are not limited to, the compounds described in German Patent No. DE 2 359 399; Japanese Patent Nos. JP 88-169 571; and JP 05-163 124; European Patent No. 0 770 375 and International Patent Application Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine; and pyrazolopyrimidine derivatives such as those mentioned in French Patent Application No. FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]-pyrimidine, and acid addition salts thereof, and tautomeric forms thereof, when a tautomeric equilibrium exists.

Examples of pyrazole derivatives include, but are not limited to, the compounds described in German Patent Nos. DE 3 843 892, DE 195 43 988 and DE 4 133 957 and International Patent Application Publication Nos. WO 94/08969 and WO 94/08970 and French Patent Application No. FR-A-2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-di-amino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and acid addition salts thereof.

Examples of pyrazolo[1,2a]pyrazol-1-one derivatives include, but are not limited to, 2,3-diamino-6,7-dihydro and 1H-5H-pyrazolo[1,2a]pyrazol-1-one.

The dyeing composition according to the present disclosure, may also contain at least one coupler conventionally used for dyeing keratin fibers. Non-limiting examples of the at least one coupler, include meta-phenylenediamines, meta-aminophenols, meta-diphenols, naphthalenic couplers and heterocyclic couplers.

Examples of the at least one coupler include, but are not limited to, 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxy-ethylamino)toluene and acid addition salts thereof.

In the dyeing composition according to the present disclosure, the at least one oxidation base may be present in an amount ranging from 0.001% to 10% by weight, for example, from 0.005% to 6% by weight, relative to the total weight of the composition. The at least one coupler may be present in an amount ranging from 0.001% and 10% by weight, for example, from 0.005% to 6% by weight, relative to the total weight of the composition.

As disclosed herein, non-limiting examples of the acid addition salts that may be used for the oxidation bases and couplers include, for instance, hydrochlorides, hydrobromides, sulfates, citrates, succinates, tartrates, lactates, tosylates, benzenesulfonates, phosphates and acetates.

According to the present disclosure, the dyeing composition may optionally comprise at least one additional direct dye chosen from cationic and nonionic dyes, that are conventionally used for dyeing keratin fibers.

Non-limiting examples of the at least one additional direct dye that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanine dyes, dyes derived from triarylmethane, and natural dyes, and mixtures thereof.

Examples of red or orange nitrobenzene dyes include, but are not limited to, 1-hydroxy-3-nitro-4-N-(γ-hydroxypropyl)aminobenzene, N-(β-hydro-xyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, and 1-amino-2-nitro-4-hydroxy-5-methylbenzene.

The at least one additional direct dye may also be chosen from yellow and green-yellow nitrobenzene direct dyes. Non-limiting examples include 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-di(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulphonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)-methyl]amino-5-nitrobenzene, 1-(β-hydroxyethyl)amino-2-nitrobenzene, and 4-(β-hydroxyethyl)amino-3-nitrobenzamide.

Mention may also be made, by way of non-limiting example, of blue and violet nitrobenzene direct dyes, such as, 1-(β-hydroxyethyl)amino-4-N,N-bis(β-hydroxyethyl) amino-2-nitrobenzene, 1-(γ-hydroxypropyl)amino-4-N,N-bis-(β-hydroxyethyl)amino-2-nitrobenzene, 1-(β-hydroxyethyl)amino-4-(N-methyl-N-β-hydroxy-ethyl)amino-2-nitro-benzene, 1-(β-hydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl) amino-2-nitro-benzene, and 2-nitro-para-phenylenediamines of formula (V):

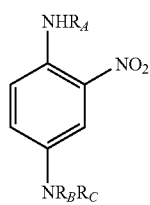

(V)

wherein:

$R_B$ is chosen from $C_1$-$C_4$ alkyl radicals, β-hydroxyethyl radicals, β-hydroxypropyl radicals, and γ-hydroxypropyl radicals; and $R_A$ and $R_C$, which are identical or different, are radicals chosen from β-hydroxyethyl, β-hydroxypropyl, γ-hydroxypropyl and β,γ-dihydroxypropyl radicals; wherein at least one of the radicals $R_B$, $R_C$ or $R_A$ is a γ-hydroxypropyl radical, and $R_B$ and $R_C$ are not simultaneously a β-hydroxyethyl radical when $R_B$ is a γ-hydroxypropyl radical, such as those described in French Patent No. FR 2 692 572.

Non-limiting examples of azo direct dyes according to the present disclosure include the cationic azo dyes described in International Patent Application Publication Nos. WO 95/15144, WO 95/01772, WO 02/078660, WO 02/100834, WO 02/100369; European Patent No. EP 714954; and French Patent Nos. FR 2 822 696, FR 2 825 702, FR 2 825 625, FR 2 822 698, FR 2 822 693, FR 2 822 694, FR 2 829 926, FR 2 807 650, and FR 2 844 269.

Among these compounds, non-limiting mention may be made of the following dyes: 1,3-dimethyl-2-[[4-(dimethylamino)phenyl]azo]-1H-imida-zolium chloride, 1,3-dimethyl-2-[(4-aminophenyl)azo]-1H-imidazolium chloride, and 1-methyl-4-[(methylphenyl-hydrazono)methyl]pyridinium methylsulfate.

Other nonlimiting examples of suitable azo direct dyes include the dyes described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, and Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Suitable quinone direct dyes according to the present disclosure include, but are not limited to, Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, and 1,4-bis(β,γ-dihydroxypropylamino)anthraquinone.

Non-limiting examples of azine dyes that may be mentioned include Basic Blue 17 and Basic Red 2.

Non-limiting examples of triarylmethane dyes that may be used according to the present disclosure include Basic Green 1, Acid Blue 9, Basic Violet 3, Basic Violet 14, Basic Blue 7, Acid Violet 49, Basic Blue 26, and Acid Blue 7.

Non-limiting examples of indoamine dyes include 2-β-hydroxyethylamino-5-[bis(β-4'-hydroxyethyl)amino] anilino-1,4-benzoquinone; 2-β-hydroxyethylamino-5-(2'-methoxy-4'-amino)anilino-1,4-benzoquinone; 3-N-(2'-chloro-4'-hydroxy)phenyl-acetylamino-6-methoxy-1,4-benzoquinoneimine; 3-N-(3'-chloro-4'-methylamino) phenylureido-6-methyl-1,4-benzoquino-neimine; and 3-[4'-N-(ethylcarbamylmethyl)amino]phenylureido-6-methyl-1, 4-benzoquinoneimine.

Dyes of tetraazapentamethine type that may be used, by way of non-limiting example, include 2-((E)-{(E)-[(1,3-dimethyl-1,3-dihydro-2H-imidazol-2-ylidene)hydra-zono] methyl}diazenyl)-1,3-dimethyl-1H-imidazol-3-ium chloride; 2-{(E)-[(1Z)-N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{ (1E)-1-[(2E)-(4-methoxy-1-methylpyridin-2(1H)-ylidene) hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)-pyridinium chloride; 1-(2-hydroxyethyl)-2-[(E)-((1E)-1-{(2E)-[1-(2-hydroxyethyl)pyridin-2(1H)-ylidene]-hydrazono}ethyl)diazenyl]pyridinium chloride; 1-methyl-2-((E)-{(E)-[(2Z)-(1-methylpyridin-2(1H)-ylidene)-hydrazono]methyl}diazenyl) pyridinium chloride; and 1-(2-hydroxyethyl)-2-[(E)-((E)-{ (2E)-[1-(2-hydroxyethyl)pyridin-2(1H)-ylidene] hydrazono}methyl)diazenyl]-pyridinium acetate.

Suitable natural direct dyes that may be used according to the present disclosure, include, but are not limited to, lawsone, juglone, alizarin, purpurin, carminic acid, kermesic acid, purpurogallin, protocatechaldehyde, indigo, isatin, curcumin, spinulosin and apigenidin. Extracts and decoctions comprising these natural dyes may also be used, for example, henna-based poultices and extracts.

When they are present in the composition, the amount of the at least one additional direct dye may range from 0.001% to 20% by weight, such as from 0.01% to 10% by weight, relative to the total weight of the composition.

According to one aspect of the present disclosure, the medium appropriate for dyeing, also known as dyeing vehicle, generally comprises water or a mixture of water and of at least one organic solvent to dissolve the compounds that would not be sufficiently water-soluble.

Non-limiting examples of the at least one organic solvent include linear and branched monoalcohols and diols comprising 2 to 10 carbon atoms, and in at least one embodiment, saturated monoalcohols and diols may be used. Useful organic solvents include, but are not limited to ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols and glycol ethers, for example ethylene glycol monomethyl, monoethyl and monobutyl ether, propylene glycol and its ethers, for instance propylene glycol monomethyl ether, butylene glycol and dipropylene glycol; and also diethylene glycol alkyl ethers, for example, the $C_1$-$C_4$ ethers, such as diethylene glycol monoethyl ether and monobutyl ether, and mixtures thereof.

When present in the composition, the at least one organic solvent may be present in an amount ranging from 1% to 40% by weight, for instance, from 5% to 30% by weight, relative to the total weight of the composition.

The dyeing composition in accordance with the present disclosure may also comprise at least one adjuvant conventionally used in compositions for dyeing the hair, such as anionic, cationic, nonionic, amphoteric, zwitterionic surfactants and their mixtures, anionic, cationic, nonionic, amphoteric, zwitterionic polymers and their mixtures, mineral and organic thickeners, for example, anionic, cationic, nonionic and amphoteric polymeric associative thickeners, antioxidants, penetrants, sequestrants, fragrances, buffers, dispersants, conditioning agents, for instance volatile and non-volatile, modified and unmodified silicones, film-forming agents, ceramides, preservatives and opacifiers.

The at least one adjuvant may be present in an amount ranging from 0.01% to 20% by weight, relative to the weight of the composition.

It is to be understood that a person skilled in the art will take care to choose this or these optional additional compounds such that the beneficial properties intrinsically associated with the dyeing composition in accordance with the present disclosure are not, or not substantially, detrimentally affected by the envisaged addition.

The pH of the dyeing composition according to the present disclosure, may range from approximately 3 to 12, for example from 5 to 11. The pH may be adjusted to the desired value with acidifying or alkalifying agents commonly used in the dyeing of keratin fibers, or alternatively with standard buffer systems. Modifying the pH within these ranges will promote the formation of compounds (I) or (II).

Examples of useful acidifying agents include, but are not limited to, mineral acids such as hydrochloric acid, nitric acid, sulfuric acid and organic acids, for example, compounds comprising at least one carboxylic acid function, such as acetic acid, tartaric acid, citric acid, lactic acid, a sulfonic acid function, a phosphonic acid function or a phosphoric acid function.

Non-limiting mention may be made of suitable alkalifying agents, for example aqueous ammonia, alkali carbonates, alkanolamines such as monoethanolamine, diethanolamine and triethanolamine and derivatives thereof, sodium hydroxide, potassium hydroxide and the compounds of formula (III):

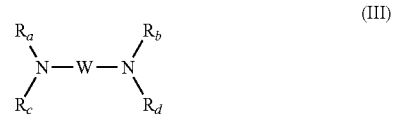

wherein W is chosen from propylene residues optionally substituted by hydroxyl groups and $C_1$-$C_4$ alkyl radicals; and $R_a$, $R_b$, $R_c$ and $R_d$, are independently chosen from a hydrogen atom, $C_1$-$C_4$ alkyl radicals, and $C_1$-$C_4$ hydroxyalkyl radicals.

The compounds of formula (II) may be obtained from compounds of formula (I) by reaction with ambient oxygen or by action of at least one oxidant, which can be any oxidant conventionally used in the art, non-limiting examples of which include hydrogen peroxide, urea peroxide, alkali metal bromates, persalts such as perborates and persulfates, and also enzymes, non-limiting examples of which include peroxidases, 2-electron oxidoreductases such as uricases, and 4-electron oxygenases such as laccases.

The at least one oxidant will also be necessary in order to obtain simultaneous lightening of the keratin fibers (lightening coloration) and/or when the composition comprises at least one oxidation base or at least one coupler.

The dyeing composition, as disclosed herein, may be in various forms, such as, but not limited to liquids, creams and gels, or in any other form appropriate for dyeing keratin fibers, such as human hair.

The coloration obtained depends on the compounds which are applied to the keratin fibers. The coloration is more intense when the entirety of these compounds are in the form of azomethine dyes with a pyrazolinone unit, i.e., are of formula (II). By promoting the formation of compounds of formula (I) from compounds of formula (II), it is possible to reduce the intensity of the coloration to the point of making it disappear.

The present invention likewise provides the compounds selected from the leuco compounds of formula (I), the azomethine dyes with a pyrazolinone unit of formula (II) as defined above, and also their mesomeric forms, their acid addition salts and their solvates, with the proviso that, when Z represents an alkyl radical, $R_1$ does not represent an optionally substituted phenyl radical and $R_2$ does not represent an alkyl radical; with the exception of the following compound:

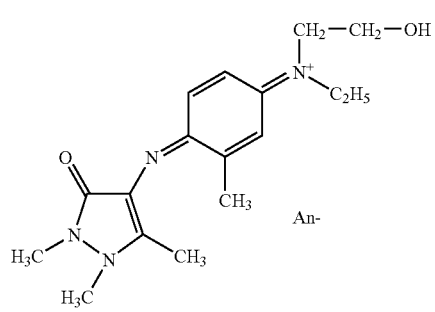

and also its mesomeric forms, its acid addition salts and its solvates. Accordingly, the present disclosure relates to the use, for coloring keratin fibers, of at least one compound chosen from leuco compounds of formula (I), azomethine dyes with a pyrazolinone unit of formula (II), and their mesomeric forms, acid addition salts and solvates thereof; with the exception of the compounds:

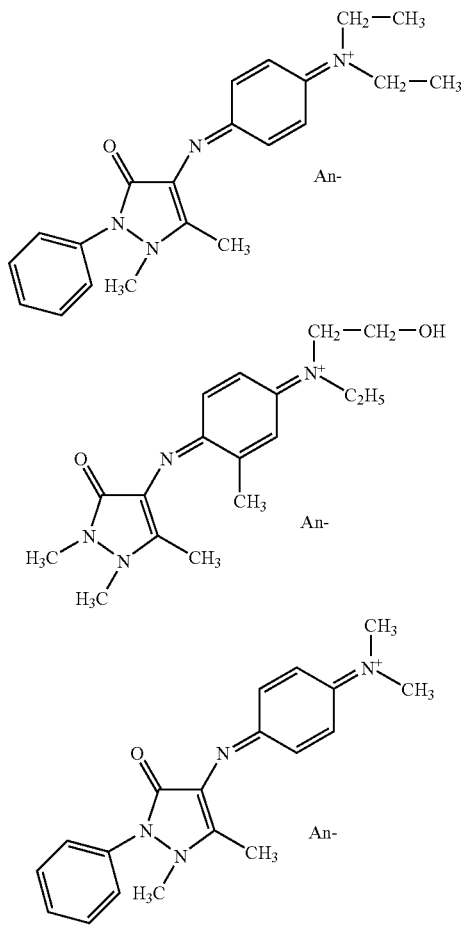

and their mesomeric forms, their acid addition salts and their solvates thereof.

The method for coloring keratin fibers, according to the present disclosure, comprises applying at least one dyeing composition, as disclosed herein, to keratin fibers comprising at least one compound chosen from leuco compounds of formula (I), azomethine dyes with a pyrazolinone unit of formula (II), and their mesomeric forms, their acid addition salts and their solvates thereof; with the exception of the compounds

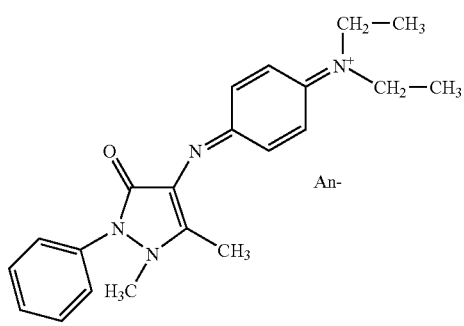

-continued

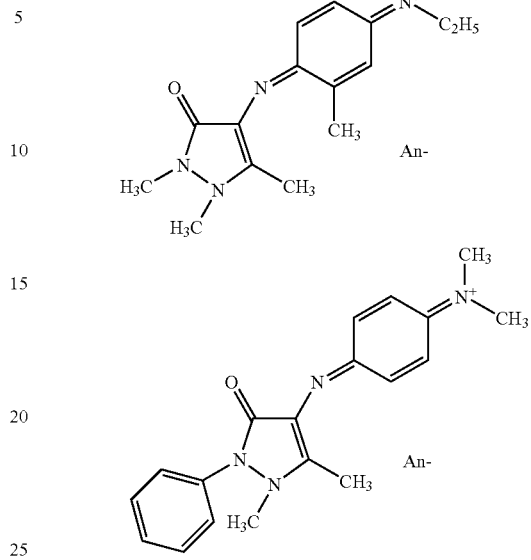

and their mesomeric forms, their acid addition salts and their solvates thereof.

According to at least one aspect of the present disclosure, the method comprises applying to the keratin fibers at least one dyeing composition comprising at least one compound of formula (II).

When at least one oxidant is employed, it may be present in the composition as disclosed herein. It may also be applied separately, in pre- or post-treatment.

Application of the composition according to the present disclosure, may or may not be followed by rinsing.

The leave-on time of the dyeing composition according to the present disclosure, may range from 3 to 60 minutes, for example, from 5 to 40 minutes, and further from 10 to 30 minutes.

The application temperature is generally at the ambient temperature, such as ranging from 25 to 55° C.

Also disclosed herein is a multi-compartment device or kit which makes it possible to carry out the method of coloring keratin fibers as described above.

The multi-compartment device, according to the present disclosure, comprises in at least one first compartment, at least one composition comprising at least one compound of formula (I) and in at least one second compartment, at least one oxidant, and optionally at least one compound of formula (II), and at least one alkaline agent.

This device can be equipped to allow the desired mixture to be deposited on the hair, such as the devices described, for example in French Application No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following example serves to illustrate the an embodiment of the present disclosure without, however, exhibiting a limiting nature.

EXAMPLES

Synthesis Examples

For examples 1 to 12 below, the following general procedure was employed:

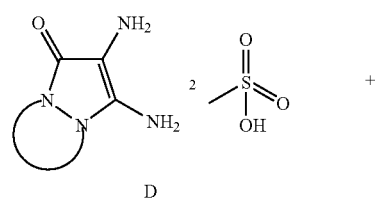

D

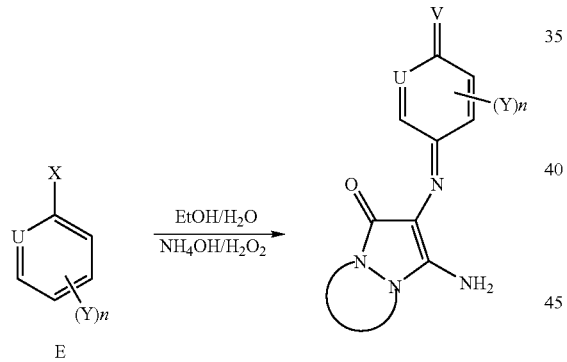

E

The pyrazolinone compound D was weighed out into a 25 ml beaker and was dissolved in water and ethanol at ambient temperature. Then compound E (for example a meta-aminophenol, or meta-phenylenediamine or hydroxynaphthalene compound) was added, followed by aqueous ammonia and, finally, hydrogen peroxide.

The reaction mixture, which initially was light yellow, became colored when the last two reactants were added. The very rapid formation of a precipitate was observed.

The reaction mixture was then stirred for a time ranging from 30 minutes to 12 hours. The product formed was isolated by filtration and then washed with water, with ethanol and with isopropyl ether before being dried at 20° C. under vacuum to constant weight.

Characterization was performed by NMR spectroscopic analysis and mass spectrometry.

Example 1

Synthesis of 3-amino-2-{[(1E)-2-amino-5-methyl-4-oxocyclohexa-2,5-dien-1-ylidene]amino}-6,7-dihydro-1H,5H-pyrazolo[1,2-a]pyrazol-1-one

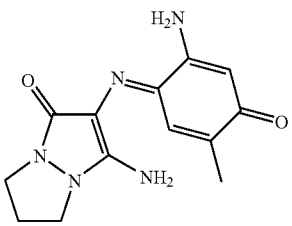

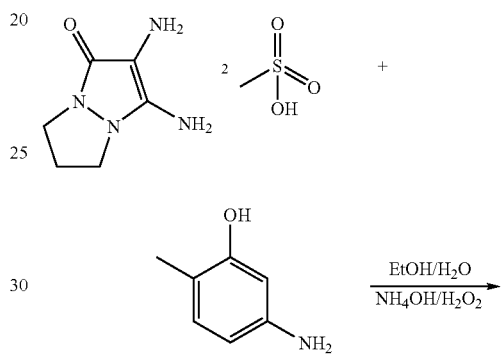

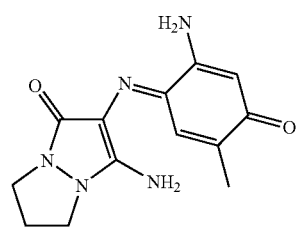

0.58 mmol of 2,3-diamino-6,7-dihydro-1H,5H-pyrazolo[1,2-a]pyrazol-1-one dimethane sulphonate was dissolved in a mixture of water and ethanol (7.5 ml/1.5 ml). This solution was admixed with 0.58 mmol of 5-amino-2-methyl phenol, then with 1.8 ml of concentrated aqueous ammonia, then with 9 ml of hydrogen peroxide.

The reaction mixture, which was initially light yellow, reddened when the last two reactants were added. The rapid formation of a red precipitate was observed.

The reaction took place at ambient temperature. After 1 night, the product formed was isolated by filtration, washed with water, washed with ethanol and then washed with isopropyl ether.

The reddish powder obtained was dried in a desiccator under vacuum for 12 hours, which resulted in 56 mg of expected product, or a yield of 36%.

Analysis was performed by mass spectrometry.

The quasi-molecular ions [M+H]+, [M+Na]+, [2M+H]+, [2M+Na]+, [M−H]− of the expected molecule $C_{13}H_{15}N_5O_2$ were principally detected.

Example 2

Synthesis of 3-amino-2-({(1E)-2-[(2-hydroxyethyl)amino]-5-methyl-4-oxocyclohexa-2,5-dien-1-ylidene}amino)-6,7-dihydro-1H,5H-pyrazolo[1,2-a]pyrazol-1-one

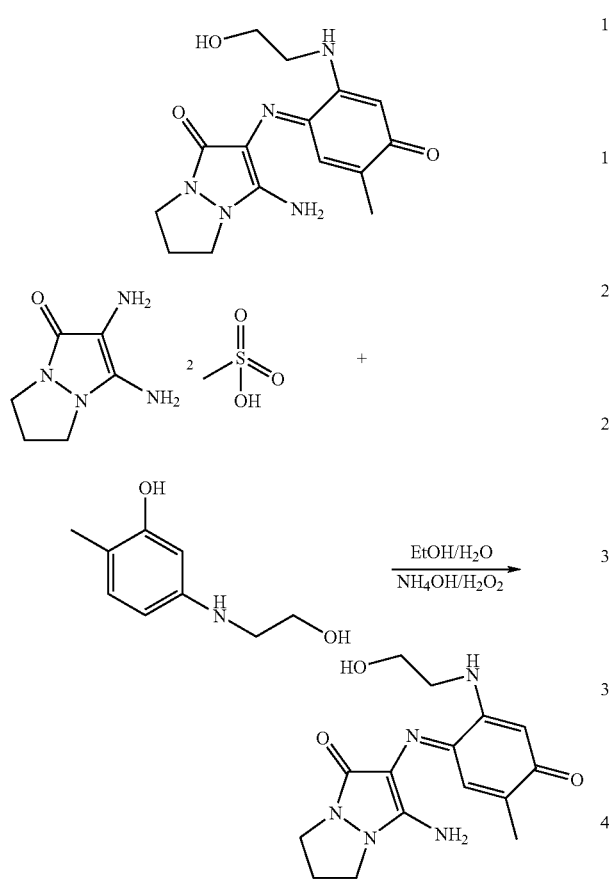

Example 3

Synthesis of 3-amino-2-{[(1E)-3-methyl-4-oxonaphthalen-1(4H)-ylidene]amino}-6,7-dihydro-1H,5H-pyrazolo[1,2-a]pyrazol-1-oe

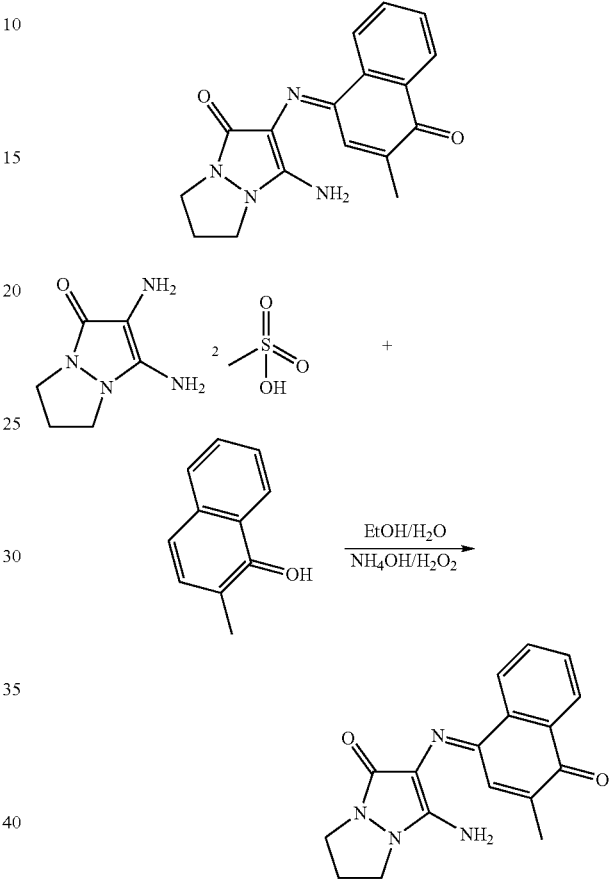

0.58 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.58 mmol of 2-(2,4-diaminophenoxy)ethanol, then with 1.8 ml of concentrated aqueous ammonia, then with 9 ml of hydrogen peroxide.

The reaction mixture, which was initially light yellow, reddened when the last two reactants were added. The rapid formation of a red precipitate was observed.

The reaction took place at ambient temperature. After 1 night, the product formed was isolated by filtration, washed with water, washed with ethanol and then washed with isopropyl ether.

The red powder obtained was dried in a desiccator under vacuum for 12 hours, which resulted in 133 mg of expected product, or a yield of 29%.

Analysis was performed by mass spectrometry.

The quasi-molecular ions [M+H]+, [M+Na]+, [2M+H]+, [2M+Na]+, of the expected molecule $C_{15}H_{19}N_5O_3$ were principally detected.

0.58 mmol of 2,3-diamino-6,7-dihydro-1H,5H-pyrazolo[1,2-a]pyrazol-1-one dimethane sulphonate was dissolved in a mixture of water and ethanol (7.5 ml/1.5 ml). This solution was admixed with 0.58 mmol of 2-methyl-1-naphthol, then with 1.8 ml of concentrated aqueous ammonia, then with 9 ml of hydrogen peroxide.

The reaction mixture, which was initially light yellow, reddened when the last two reactants were added. The rapid formation of a red precipitate was observed.

The reaction took place at ambient temperature. After 1 night, the product formed was isolated by filtration, washed with water, with ethanol and then washed with isopropyl ether.

The dark red powder obtained was dried in a desiccator under vacuum for 12 hours, which resulted in 38 mg of expected product.

Analysis was performed by mass spectrometry.

The quasi-molecular ions [M+H]+, [M+Na]+, [2M+H]+, [2M+Na]+, of the expected molecule $C_{17}H_{16}N_4O_2$ were principally detected.

Example 4

Synthesis of 3-amino-2-{[(1E)-2-amino-3-chloro-5-methyl-4-oxocyclohexa-2,5-dien-1-ylidene]amino}-6,7-dihydro-1H,5H-pyrazolo[1,2-a]pyrazol-1-one

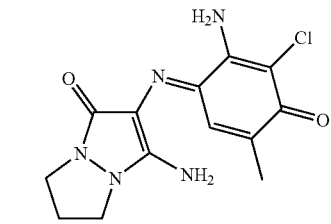

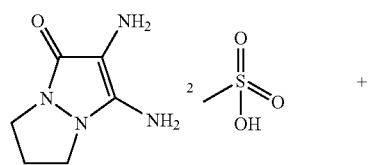

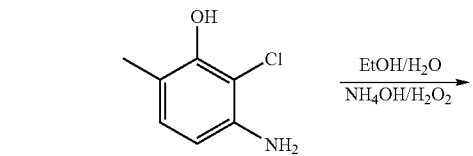

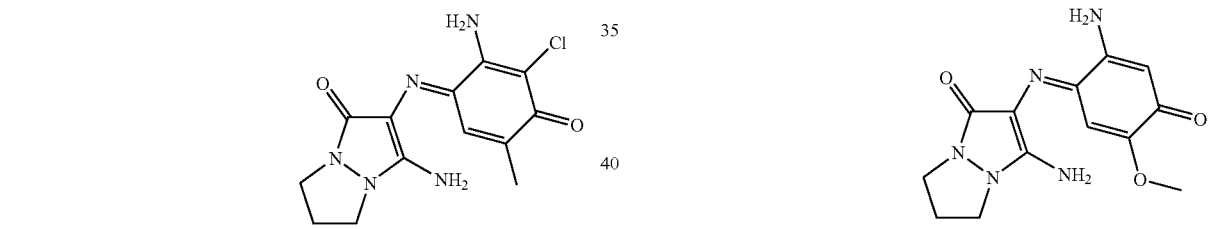

0.58 mmol of 2,3-diamino-6,7-dihydro-1H,5H-pyrazolo[1,2-a]pyrazol-1-one dimethane sulphonate was dissolved in a mixture of water and ethanol (7.5 ml/1.5 ml). This solution was admixed with 0.58 mmol of 3-amino-2-chloro-6-methylphenol, then with 1.8 ml of concentrated aqueous ammonia, then with 9 ml of hydrogen peroxide.

The reaction mixture, which was initially light yellow, reddened when the last two reactants were added. The rapid formation of a red precipitate was observed.

The reaction took place at ambient temperature. After 1 night, the product formed was isolated by filtration, washed with water, washed with ethanol and then washed with isopropyl ether.

The reddish powder obtained was dried in a desiccator under vacuum for 12 hours, which resulted in 56 mg of expected product, or a yield of 36%. Analysis was performed by mass spectrometry.

The quasi-molecular ions [M+H]+, [M+Na]+, [2M+H]+, [2M+Na]+, of the expected molecule $C_{13}H_{14}ClN_5O_2$ were principally detected.

Example 5

Synthesis of 3-amino-2-{[(1E)-2-amino-5-methoxy-4-oxocyclohexa-2,5-dien-1-ylidene]amino}-6,7-dihydro-1H,5H-pyrazolo[1,2-a]pyrazol-1-one 0.05 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.05 mmol of 5-amino-2-methoxyphenol, then with 1.8 ml of concentrated aqueous ammonia, then with 9 ml of hydrogen peroxide.

The reaction mixture, which was initially light yellow, reddened when the last two reactants were added. The rapid formation of a coppery red coloration was observed.

The reaction took place at ambient temperature. After 1 night, the product formed was isolated by filtration, washed with water, washed with ethanol and then washed with isopropyl ether.

The brown-red powder obtained was dried in a desiccator under vacuum for 12 hours, which resulted in 3.1 mg of expected product.

Analysis was performed by mass spectrometry.

The quasi-molecular ions [M+H]+, [M+Na]+, [2M+H]+, [2M+Na]+, of the expected molecule $C_{13}H_{15}N_5O_3$ were principally detected.

Example 6

Synthesis of 3-amino-2-({(1E)-2-[(2-hydroxyethyl)amino]-4-imino-5-methoxycyclohexa-2,5-dien-1-ylidene}amino)-6,7-dihydro-1H,5H-pyrazolo[1,2-a]pyrazol-1-one

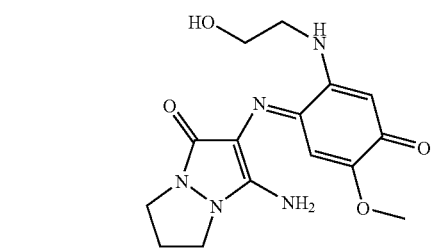

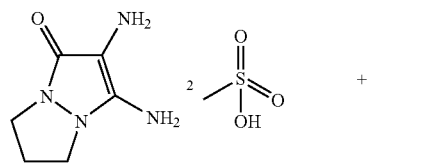

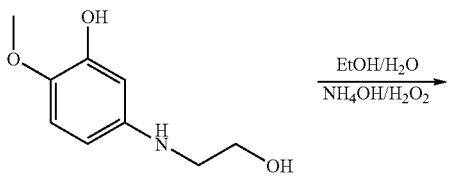

0.05 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.05 mmol of 5-[(2-hydroxyethyl)amino]-2-methoxyphenol, then with 1.8 ml of concentrated aqueous ammonia, then with 9 ml of hydrogen peroxide.

The reaction mixture, which was initially light yellow, reddened when the last two reactants were added. The rapid formation of a mahogany red coloration was observed.

The reaction took place at ambient temperature. After 1 night, this solution was analyzed by mass spectrometry, by detecting the quasi-molecular ions [M+H]+, [M+Na]+, [2M+H]+, [2M+Na]+, of the expected molecule $C_{15}H_{20}N_6O_3$ and confirmed the presence of the expected molecule $C_{15}H_{20}N_6O_3$.

Example 7

Synthesis of 3-amino-2-{[(1E)-2-hydroxy-4-imino-5-methylcyclohexa-2,5-dien-1-ylidene]amino}-6,7-dihydro-1H,5H-pyrazolo[1,2-a]pyrazol-1-one

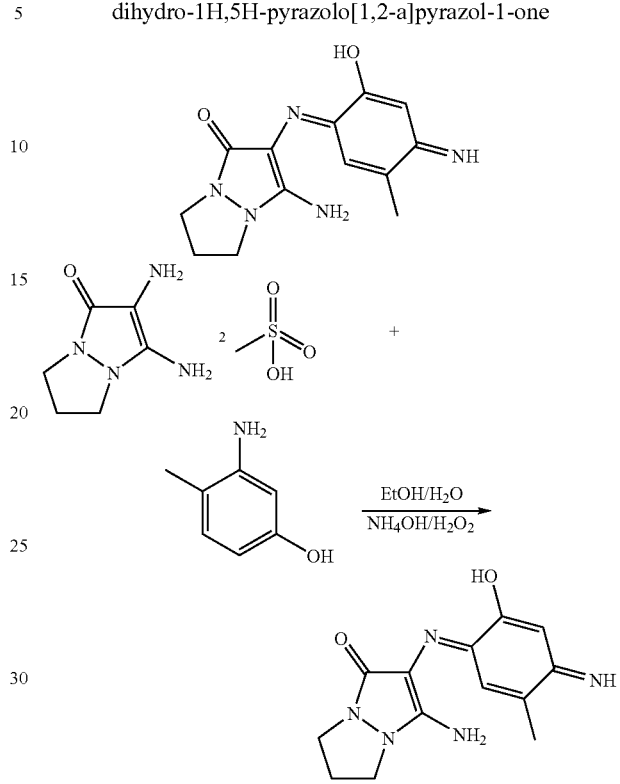

0.05 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.05 mmol of 3-amino-4-methylphenol, then with 1.8 ml of concentrated aqueous ammonia, then with 9 ml of hydrogen peroxide.

The reaction mixture, which was initially light yellow, reddened when the last two reactants were added. The rapid formation of a brown red coloration was observed.

The reaction took place at ambient temperature. After 1 night, this solution was analyzed by mass spectrometry, by detecting the quasi-molecular ions [M+H]+, [M+Na]+, [2M+H]+, [2M+Na]+, of the expected molecule $C_{13}H_{15}N_5O_2$, which confirmed the presence of the expected molecule $C_{13}H_{15}N_5O_2$.

Example 8

Synthesis of 3-amino-2-({(1Z,4E)-2-amino-4-[(2-hydroxyethyl)imino]-5-methoxycyclohexa-2,5-dien-1-ylidene}amino)-6,7-dihydro-1H,5H-pyrazolo[1,2-a]pyrazol-1-one

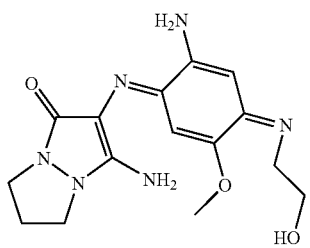

-continued

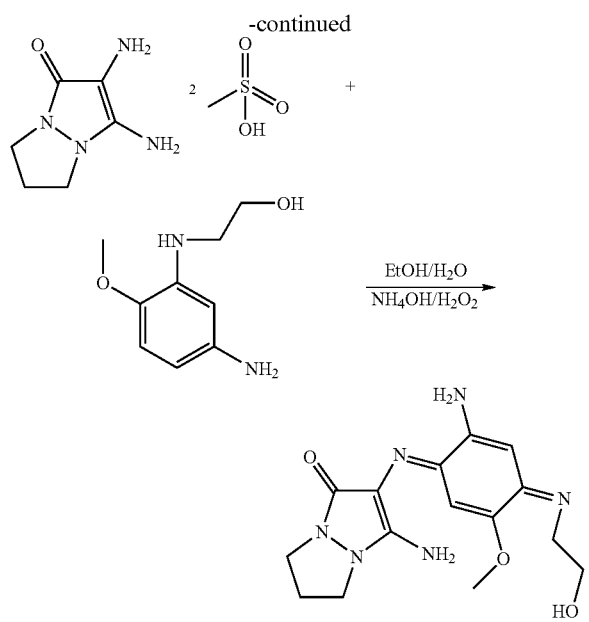

0.05 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.05 mmol of 2-[(5-amino-2-methoxyphenyl)amino]ethanol, then with 1.8 ml of concentrated aqueous ammonia, then with 9 ml of hydrogen peroxide.

The reaction mixture, which was initially light yellow, reddened when the last two reactants were added. The rapid formation of an intense brown red coloration was observed.

The reaction took place at ambient temperature. After 1 night, this solution was analyzed by mass spectrometry, by detecting the quasi-molecular ions [M+H]+, [M+Na]+, [2M+H]+, [2M+Na]+, of the expected molecule $C_{15}H_{20}N_6O_3$, which confirmed the presence of the expected molecule $C_{15}H_{20}N_6O_3$.

Example 9

Synthesis of 3-amino-2-{[(1E)-2-hydroxy-4-imino-5-methoxycyclohexa-2,5-dien-1-ylidene]amino}-6,7-dihydro-1H,5H-pyrazolo[1,2-a]pyrazol-1-one

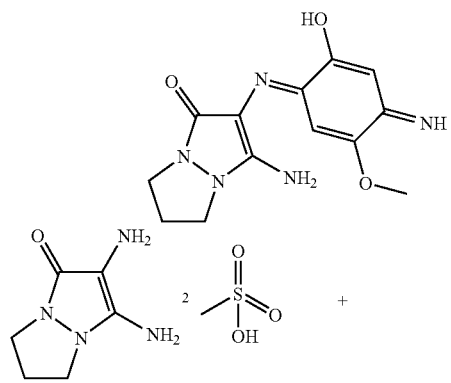

-continued

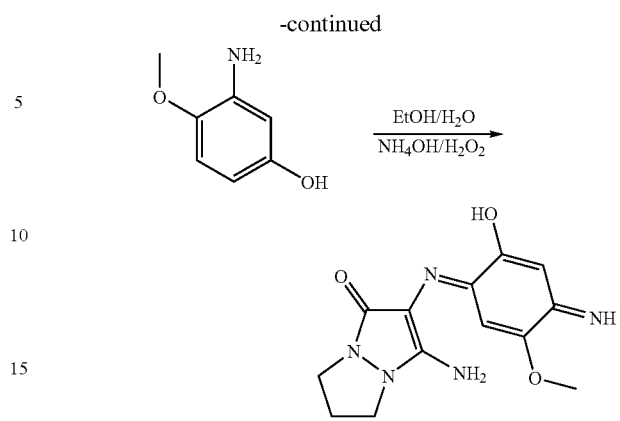

0.05 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.05 mmol of 3-amino-4-methoxyphenol, then with 1.8 ml of concentrated aqueous ammonia, then with 9 ml of hydrogen peroxide.

The reaction mixture, which was initially light yellow, reddened when the last two reactants were added. The rapid formation of a brown red coloration was observed.

The reaction took place at ambient temperature. After 1 night, this solution was analyzed by mass spectrometry, by detecting the quasi-molecular ions [M+H]+, [M+Na]+, [2M+H]+, [2M+Na]+, of the expected molecule $C_{13}H_{15}N_5O_3$, which confirmed the presence of the expected molecule $C_{13}H_{15}N_5O_3$.

Example 10

Synthesis of 3-amino-2-{[(1Z)-2-amino-6-methyl-4-oxocyclohexa-2,5-dien-1-ylidene]amino}-6,7-dihydro-1H,5H-pyrazolo[1,2-a]pyrazol-1-one

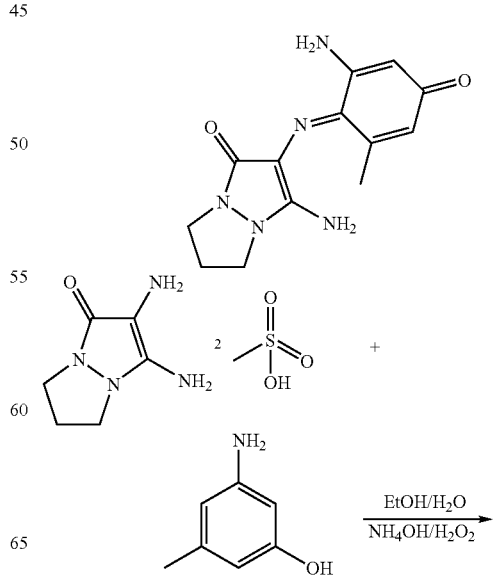

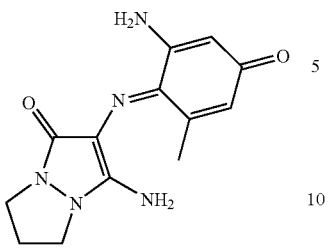

0.5 mmol of 2,3-diamino-6,7-dihydro-1H,5H-pyrazolo[1,2-a]pyrazol-1-one dimethane sulfonate was dissolved in a mixture of water and ethanol (7.5 ml/1.5 ml). This solution was admixed with 0.05 mmol of 3-amino-5-methylphenol, then with 1.8 ml of concentrated aqueous ammonia, then with 9 ml of hydrogen peroxide.

The reaction mixture, which was initially light yellow, reddened when the last two reactants were added. The rapid formation of a red coloration was observed.

The reaction took place at ambient temperature. After 1 night, this solution was analyzed by mass spectrometry, by detecting the quasi-molecular ions [M+H]+, [M+Na]+, [2M+H]+, [2M+Na]+, of the expected molecule $C_{13}H_{15}N_5O_2$, which confirmed the presence of the expected molecule $C_{13}H_{15}N_5O_2$.

Example 11

Synthesis of 3-amino-2-[(2-amino-3-chloro-5-methyl-4-oxocyclohexa-2,5-dien-1-ylidene)amino]-5,6,7,8-tetra-hydro-1H-pyrazolo[1,2-a]pyridazin-1-one

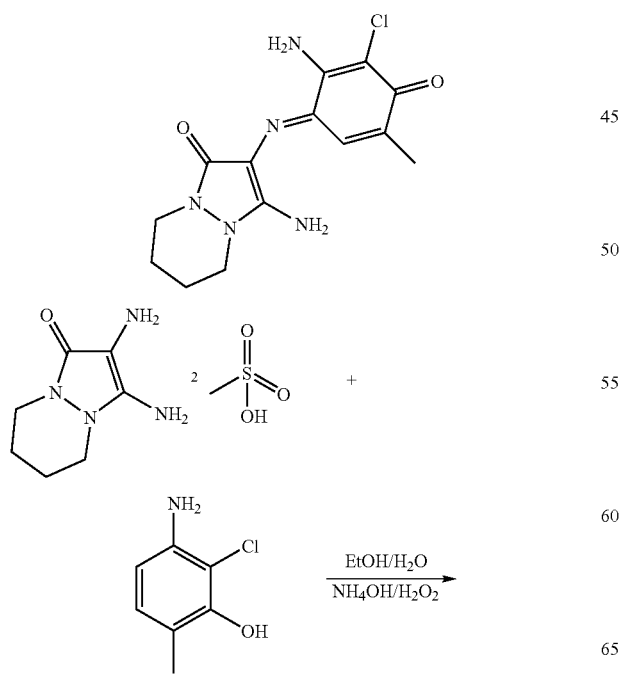

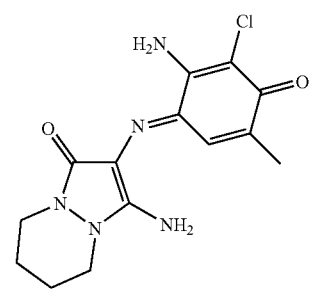

0.68 mmol of 2,3-diamino-5,6,7,8-tetrahydro-1H-pyrazolo[1,2-a]pyridazin-1-one methanesulfonate was dissolved in a mixture of water and ethanol (7.5 ml/1.5 ml). This solution was admixed with 0.68 mmol of 3-amino-2-chloro-6-methylphenol, then with 1.8 ml of concentrated aqueous ammonia, then with 9 ml of hydrogen peroxide.

The reaction mixture, which was initially light yellow, reddened when the last two reactants were added. The rapid formation of a dark red precipitate was observed.

The reaction took place at ambient temperature. After 1 night, the product formed was isolated by filtration and washed with water, washed with ethanol and then washed with isopropyl ether.

The dark red powder obtained was dried in a desiccator under vacuum for 12 hours, which resulted in 150 mg of expected product, or a yield of 59%.

Analysis was performed by mass spectrometry.

The quasi-molecular ions [M+H]+, [M+Na]+, [2M+H]+, [2M+Na]+, of the expected molecule $C_{14}H_{16}ClN_5O_2$ were principally detected.

Example 12

Synthesis of 9-amino-8-[(2-amino-3-chloro-5-methyl-4-oxocyclohexa-2,5-dien-1-ylidene)amino]-3-methyl-2,3,4,5-tetrahydro-1H,7H-pyrazolo[1,2-a][1,2,5]triazepin-7-one

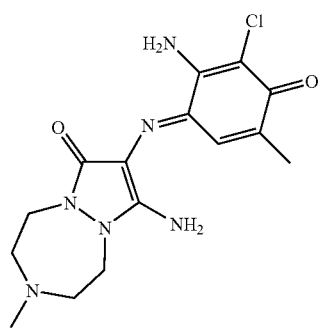

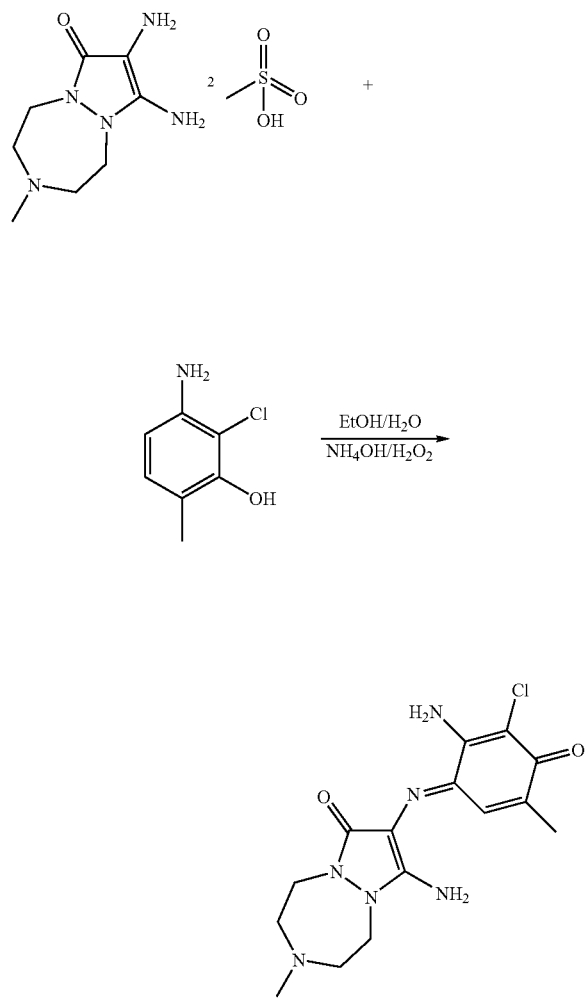

0.32 mmol of 8,9-diamino-3-methyl-2,3,4,5-tetrahydro-1H, 7H-pyrazolo[1,2-a][1,2,5]triazepin-7-one methanesulfonate was dissolved in a mixture of water and ethanol (7.5 ml/1.5 ml). This solution was admixed with 0.32 mmol of 3-amino-2-chloro-6-methylphenol, then with 1.8 ml of concentrated aqueous ammonia, then with 9 ml of hydrogen peroxide.

The reaction mixture, which was initially orange, reddened when the last two reactants were added. The rapid formation of a red precipitate was observed.

The reaction took place at ambient temperature. After 1 night, the product formed was isolated by filtration and washed with water, washed with ethanol and then washed with isopropyl ether.

The dark red powder obtained was dried in a desiccator under vacuum for 12 hours, which resulted in 57 mg of expected product, or a yield of 57%.

Analysis was performed by mass spectrometry.

The quasi-molecular ions [M+H]+, [M+Na]+, [2M+H]+, [2M+Na]+, of the expected molecule $C_{15}H_{19}ClN_6O_2$ were principally detected.

For examples 13 to 20 below, the following general procedure was employed:

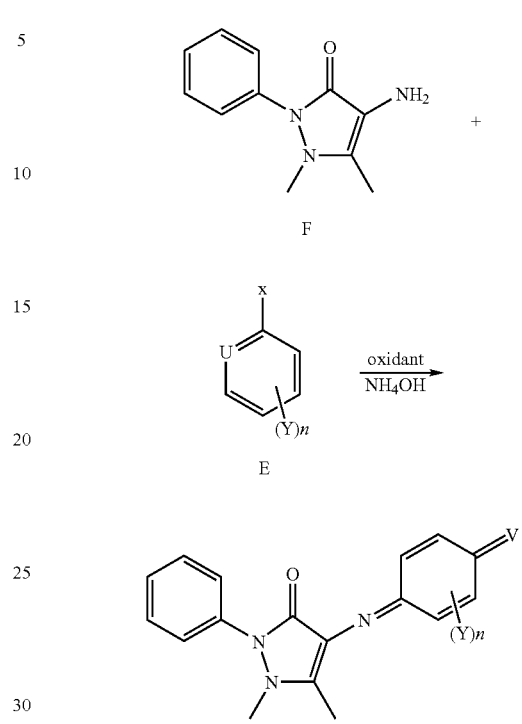

The 4-amino-1,5-dimethyl-2-phenyl-1,2-dihydro-3H-pyrazol-3-one (compound F) was weighed out into a 25 ml beaker and was dissolved in water and ethanol at ambient temperature. Subsequently the meta-aminophenol or meta-phenylenediamine or hydroxynaphthalene (compound E) was added, followed by aqueous ammonia and, finally, by the oxidant water.

The reaction mixture, which was initially light yellow, became colored when the last two reactants were added. The rapid formation of a precipitate is observed.

The reaction mixture thus obtained was stirred for a time ranging from 30 minutes to 12 hours. The product formed was isolated by filtration and then washed with water, with ethanol and with isopropyl ether. The compound recovered in powder form was dried at 20° C. under vacuum to constant weight.

Characterization was performed by NMR spectroscopy analysis and mass spectrometry.

Example 13

Synthesis of 4-{[(1E)-2-amino-4-iminocyclohexa-2,5-dien-1-ylidene]amino}-1,5-dimethyl-2-phenyl-1,2-dihydro-3H-pyrazol-3-one

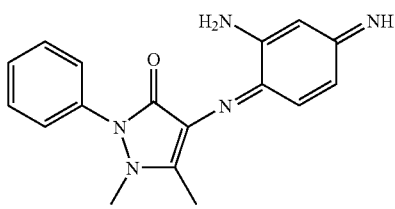

-continued

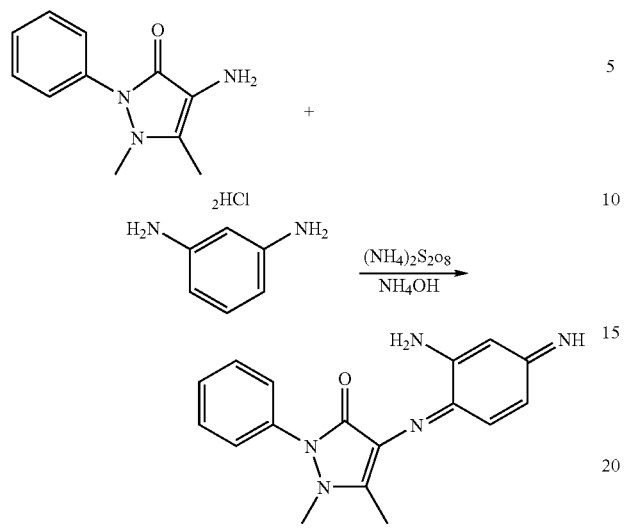

20 mmol of 4-amino-1,5-dimethyl-2-phenyl-1,2-dihydro-3H-pyrazol-3-one and 20 mmol of meta-phenylene diamine was dissolved in 30 g of an ice/water mixture and the pH was adjusted to 10 using 20 ml of 20% aqueous ammonia. While stirring, a solution of 24 mmol of ammonium persulfate in 10 ml of water was added dropwise over 30 minutes. The mixture was stirred at 0° C. for 1 h 30 min and the solid formed was separated by filtration and washed with water and acetone and dried in a desiccator under vacuum for 12 hours, which resulted in 1.8 g of expected product, or a yield of 30%.

Analysis was performed by mass spectrometry.

The quasi-molecular ions [M+H]+, [M+Na]+, [2M+H]+, [2M+Na]+, of the expected molecule $C_{10}H_{17}N_5O$ were principally detected.

Example 14

Synthesis of 4-{[(1E)-2-amino-4-imino-3,5-dimethylcyclohexa-2,5-dien-1-ylidene]amino}-1,5-dimethyl-2-phenyl-1,2-dihydro-3H-pyrazol-3-one hydrochloride

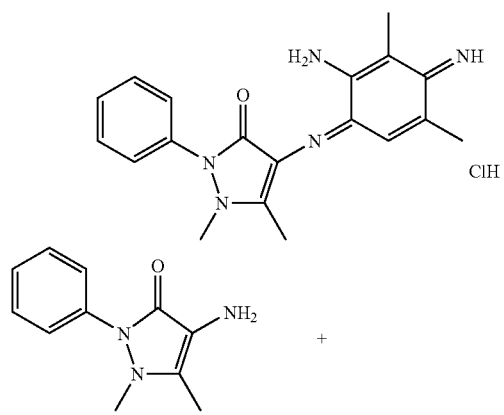

-continued

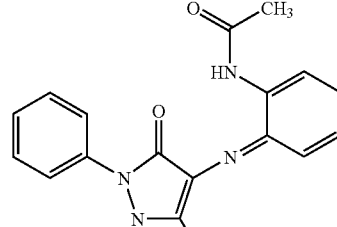

60 mmol of 4-amino-1,5-dimethyl-2-phenyl-1,2-dihydro-3H-pyrazol-3-one was dissolved in 100 ml of water and 200 g of ice. This solution was admixed with 24 mmol of ferric chloride hexahydrate in a single addition, followed by 300 ml of saturated aqueous sodium chloride. After 15 minutes, sodium chloride was added to saturation, and the mixture was cooled at 0° C. for 4 hours.

The precipitate formed was filtered off with suction, washed with water and dried in a desiccator under vacuum for 12 hours, which resulted in 3.5 g of expected product, or a yield of 16%. Analysis was performed by mass spectrometry.

The quasi-molecular ions [M+H]+, [M+Na]+, [2M+H]+, [2M+Na]+, of the expected molecule $C_{19}H_{21}N_5O$ were principally detected.

Example 15

Synthesis of N-{(6E)-6-[(1,5-dimethyl-3-oxo-2-phenyl-2,3-dihydro-1H-pyrazol-4-yl)imino]-3-oxocyclohexa-1,4-dien-1-yl}acetamide

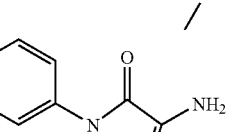

-continued

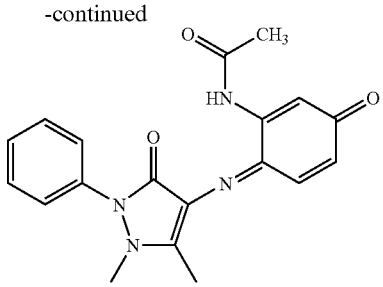

10 mmol of 4-amino-1,5-dimethyl-2-phenyl-1,2-dihydro-3H-pyrazol-3-one was dissolved in 30 ml of water. This solution was admixed with 10 mmol of N-(3-hydroxyphenyl)acetamide in solution in 30 ml of 2-propanol, 3 ml of 20% aqueous ammonia and 22 mmol of potassium ferricyanide at a temperature ranging from 5 to 10° C.

After 15 minutes, the precipitate formed was filtered off with suction, washed with water and dried in a desiccator under vacuum for 12 hours, which resulted in 1.42 g of expected product, or a yield of 40%.

Analysis was performed by mass spectrometry.

The quasi-molecular ions [M+H]+, [M+Na]+, [2M+H]+, [2M+Na]+, of the expected molecule $C_{19}H_{18}N_4O_3$ were principally detected.

Example 16

Synthesis of 1,5-dimethyl-4-{[(1Z)-3-methyl-4-oxo-cyclohexa-2,5-dien-1-ylidene]amino}-2-phenyl-1,2-dihydro-3H-pyrazol-3-one

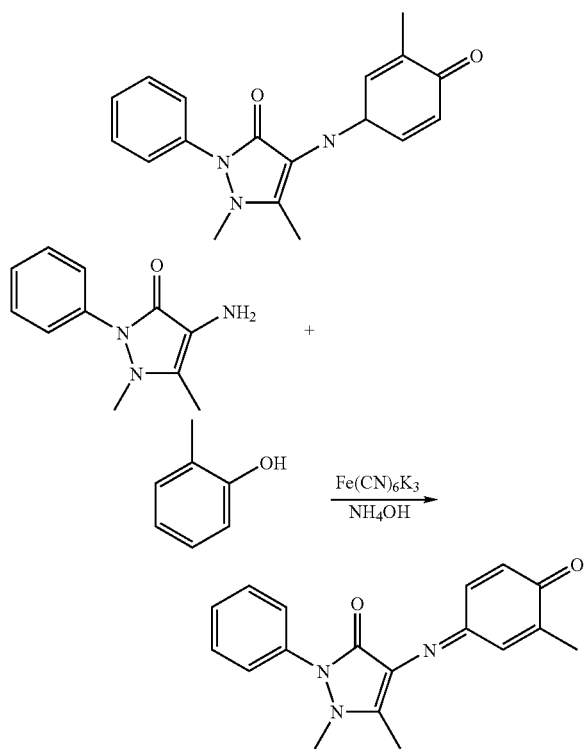

10 mmol of 4-amino-1,5-dimethyl-2-phenyl-1,2-dihydro-3H-pyrazol-3-one was dissolved in 30 ml of water. This solution was admixed with 10 mmol of o-cresol in solution in 30 ml of 2-propanol, 3 ml of 20% aqueous ammonia and 22 mmol of potassium ferricyanide at a temperature ranging from 5 to 10° C.

After 15 minutes, the precipitate formed was filtered off with suction, washed with water and dried in a desiccator under vacuum for 12 hours, which resulted in 1 g of expected product, or a yield of 32%.

Analysis was performed by mass spectrometry.

The quasi-molecular ions [M+H]+, [M+Na]+, [2M+H]+, [2M+Na]+, of the expected molecule $C_{18}H_{17}N_3O_2$ were principally detected.

Example 17

Synthesis of 1,5-dimethyl-4-{[(1Z)-2-methyl-4-oxo-cyclohexa-2,5-dien-1-ylidene]amino}-2-phenyl-1,2-dihydro-3H-pyrazol-3-one

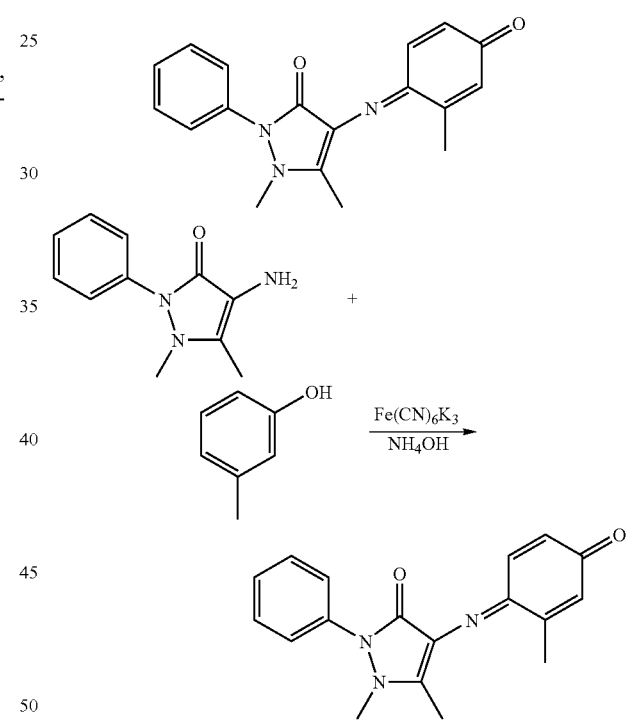

10 mmol of 4-amino-1,5-dimethyl-2-phenyl-1,2-dihydro-3H-pyrazol-3-one was dissolved in 30 ml of water. This solution was admixed with 10 mmol of meta-cresol in solution in 30 ml of 2-propanol, 3 ml of 20% aqueous ammonia and 22 mmol of potassium ferricyanide at a temperature ranging from 5 to 10° C.

After 15 minutes, the precipitate formed was filtered off with suction, washed with water and dried in a desiccator under vacuum for 12 hours, which resulted in 1.7 g of expected product, or a yield of 54%.

Analysis was performed by mass spectrometry.

The quasi-molecular ions [M+H]+, [M+Na]+, [2M+H]+, [2M+Na]+, of the expected molecule $C_{18}H_{17}N_3O_2$ were principally detected.

Example 18

Synthesis of 4-{[(1E)-2-chloro-4-oxocyclohexa-2,5-dien-1-ylidene]amino}-1,5-dimethyl-2-phenyl-1,2-dihydro-3H-pyrazol-3-one

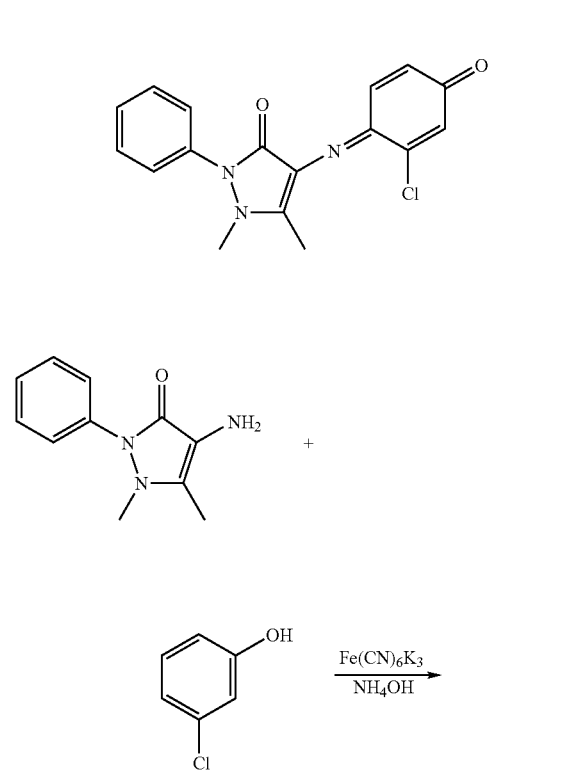

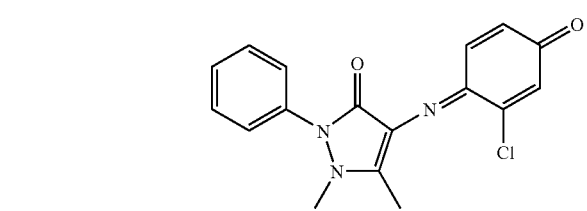

10 mmol of 4-amino-1,5-dimethyl-2-phenyl-1,2-dihydro-3H-pyrazol-3-one was dissolved in 30 ml of water. This solution was admixed with 10 mmol of 3-chlorophenol in solution in 30 ml of 2-propanol, 3 ml of 20% aqueous ammonia and 22 mmol of potassium ferricyanide at a temperature ranging from 5 to 10° C.

After 15 minutes, the precipitate formed was filtered off with suction, washed with water and dried in a desiccator under vacuum for 12 hours, which resulted in 1.45 g of expected product, or a yield of 43%.

Analysis was performed by mass spectrometry.

The quasi-molecular ions [M+H]+, [M+Na]+, [2M+H]+, [2M+Na]+, of the expected molecule $C_{17}H_{14}ClN_3O_2$ were principally detected.

Example 19

Synthesis of 4-{[(1Z)-3-chloro-4-oxocyclohexa-2,5-dien-1-ylidene]amino}-1,5-dimethyl-2-phenyl-1,2-dihydro-3H-pyrazol-3-one

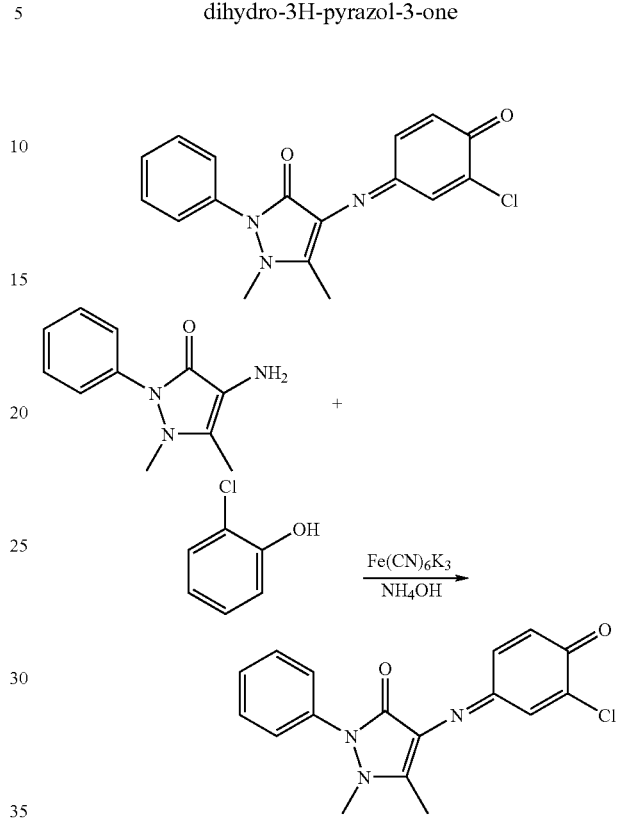

10 mmol of 4-amino-1,5-dimethyl-2-phenyl-1,2-dihydro-3H-pyrazol-3-one was dissolved in 30 ml of water. This solution was admixed with 10 mmol of 2-chlorophenol in solution in 30 ml of 2-propanol, 3 ml of 20% aqueous ammonia and 22 mmol of potassium ferricyanide at a temperature ranging from 5 to 10° C.

After 15 minutes, the precipitate formed was filtered off with suction, washed with water and dried in a desiccator under vacuum for 12 hours, which resulted in 1.4 g of expected product, or a yield of 42%.

Analysis was performed by mass spectrometry.

The quasi-molecular ions [M+H]+, [M+Na]+, [2M+H]+, [2M+Na]+, of the expected molecule $C_{17}H_{14}ClN_3O_2$ were principally detected.

Example 20

Synthesis of 4-{[(1E)-3-methoxy-4-oxocyclohexa-2,5-dien-1-ylidene]amino}-1,5-dimethyl-2-phenyl-1,2-dihydro-3H-pyrazol-3-one

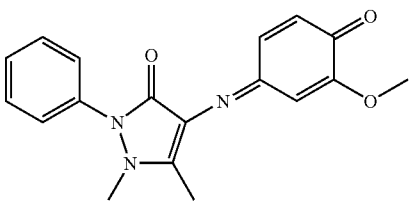

-continued

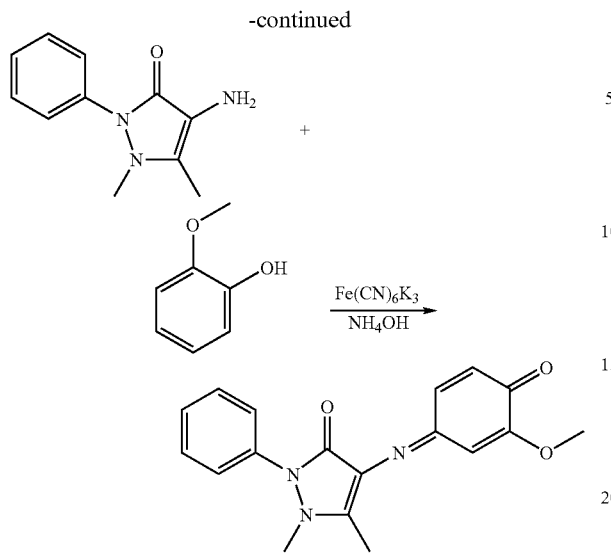

10 mmol of 4-amino-1,5-dimethyl-2-phenyl-1,2-dihydro-3H-pyrazol-3-one was dissolved in 30 ml of water. This solution was admixed with 10 mmol of 2-methoxyphenol in solution in 30 ml of 2-propanol, 3 ml of 20% aqueous ammonia and 22 mmol of potassium ferricyanide at a temperature ranging from 5 to 10° C.

After 15 minutes, the precipitate formed was filtered off with suction, washed with water and dried in a desiccator under vacuum for 12 hours, which resulted in 1.6 g of expected product, or a yield of 47%.

Analysis was performed by mass spectrometry.

The quasi-molecular ions [M+H]+, [M+Na]+, [2M+H]+, [2M+Na]+, of the expected molecule $C_{18}H_{17}ClN_3O_3$ were principally detected.

Example 21

Synthesis of N-{(4E)-3-amino-4-[(1,5-dimethyl-3-oxo-2-phenyl-2,3-dihydro-1H-pyrazol-4-yl) imino] cyclohexa-2,5-dien-1-ylidene}-N-methylmethanaminium perchlorate

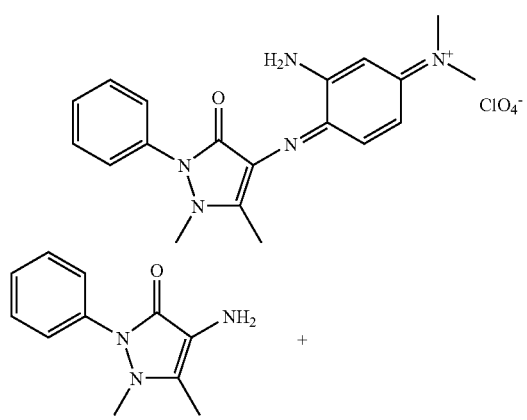

-continued

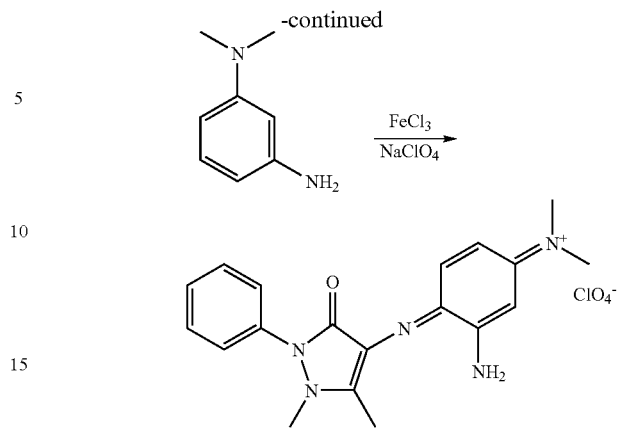

60 mmol of 4-amino-1,5-dimethyl-2-phenyl-1,2-dihydro-3H-pyrazol-3-one and 60 mmol of N,N-dimethylbenzene-1,3-diamine was dissolved in 300 ml of ice-water. This solution was admixed with 60 mmol of ferric chloride and 300 ml of saturated aqueous sodium chloride. Sodium perchlorate was added to saturation, and the mixture was left to stand for 30 minutes at zero degrees.

After 15 minutes, the precipitate formed was filtered off with suction, washed with water and dried in a desiccator under vacuum for 12 hours, which resulted in 3 g of expected product, or a yield of 12%.

Analysis was performed by mass spectrometry.

The expected cation $[C_{19}H_{12}ClN_5O]+$ was principally detected.

Example 22

Synthesis of (4E)-5-amino-4-[(1,5-dimethyl-3-oxo-2-phenyl-2,3-dihydro-1H-pyrazol-4-yl)imino]-2-methylcyclohexa-2,5-dien-1-iminium perchlorate

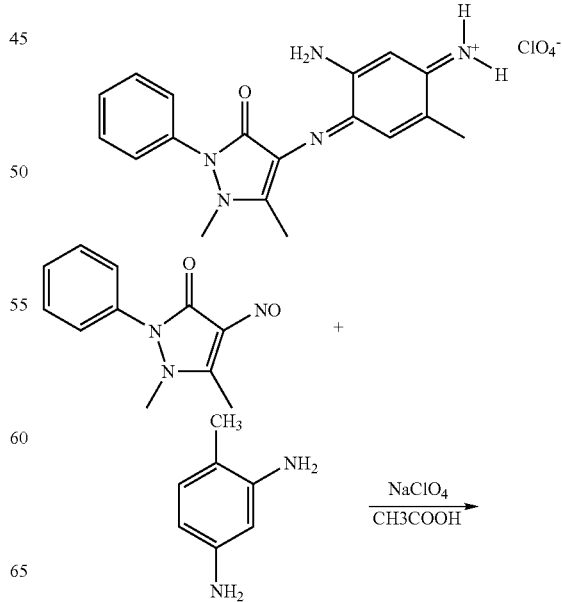

-continued

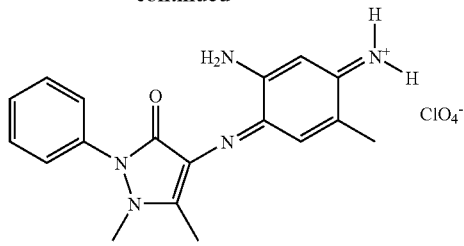

50 mmol of 1,5-dimethyl-4-nitroso-2-phenyl-1,2-dihydro-3H-pyrazol-3-one was dissolved in a solution of 850 ml of acetic acid and 1250 ml of water. This solution was admixed with 50 mmol of 4-methylbenzene-1,3-diamine and stirring was continued for 2 h 30 min. Sodium perchlorate was added to saturation, and the mixture was left to stand for 30 minutes at zero degrees.

The precipitate formed was filtered off with suction, washed with water and dried in a desiccator under vacuum for 12 hours, which resulted in 10 g of expected product, or a yield of 57%. Analysis was performed by mass spectrometry.

The expected cation $[C_{19}H_{22}N_5O]+$ was principally detected.

Dyeing Examples

Dye 1
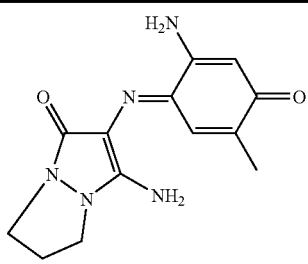

Dye 2
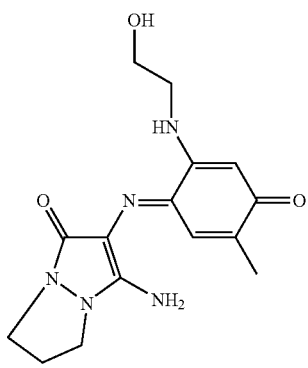

Dye 3
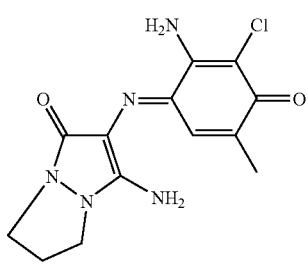

-continued

Dye 4
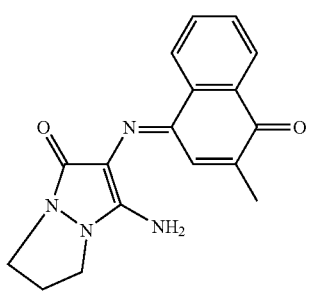

Dye 5
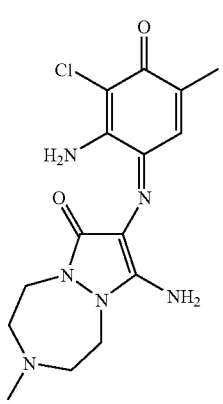

Dye 6
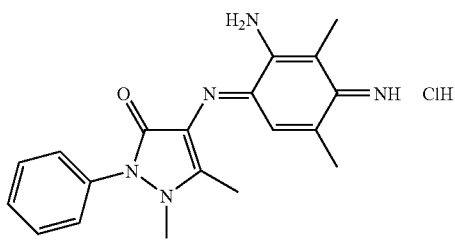

Dye 7
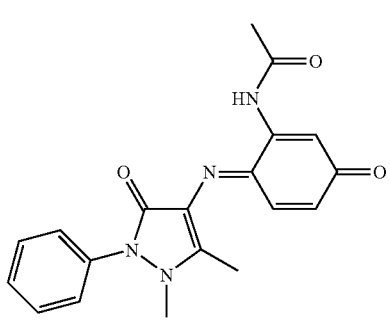

Dye 8
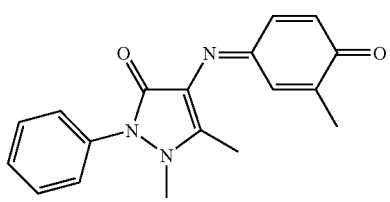

-continued

Dye 9
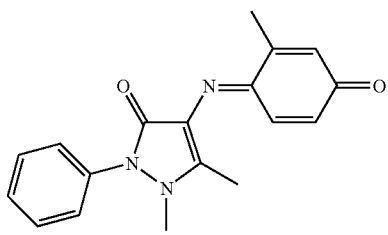

Dye 10
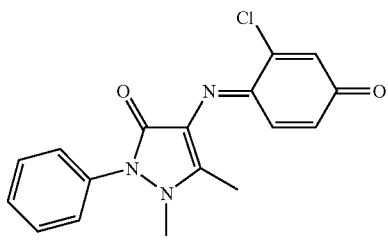

Dye 11
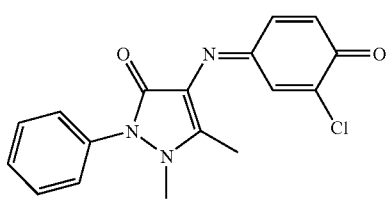

-continued

Dye 12
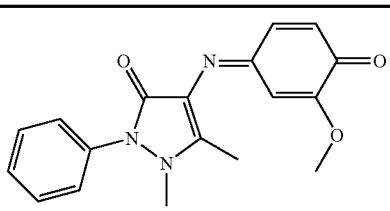

Dye 13
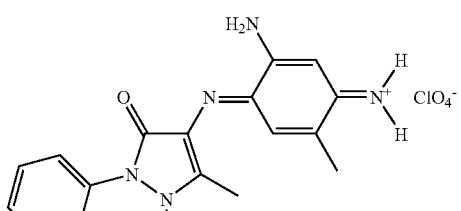

Dyeing in Acidic Medium

The following dyeing compositions were prepared:

| Composition | 1 | 2 | 3 | 4 | 5 | 6 | 7 | 8 | 9 | 10 | 11 | 12 | 13 |
|---|---|---|---|---|---|---|---|---|---|---|---|---|---|
| Dye 1 | $10^{-3}$ mol | — | — | — | — | — | | | | | | | |
| Dye 2 | — | $10^{-3}$ mol | — | — | — | — | | | | | | | |
| Dye 3 | — | — | $10^{-3}$ mol | — | — | — | | | | | | | |
| Dye 4 | — | — | — | $10^{-3}$ mol | — | — | | | | | | | |
| Dye 5 | — | — | — | — | $10^{-3}$ mol | — | | | | | | | |
| Dye 6 | — | — | — | — | — | $10^{-3}$ mol | | | | | | | |
| Dye 7 | | | | | | | $10^{-3}$ mol | | | | | | |
| Dye 8 | | | | | | | | $10^{-3}$ mol | | | | | |
| Dye 9 | | | | | | | | | $10^{-3}$ mol | | | | |
| Dye 10 | | | | | | | | | | $10^{-3}$ mol | | | |
| Dye 11 | | | | | | | | | | | $10^{-3}$ mol | | |
| Dye 12 | | | | | | | | | | | | $10^{-3}$ mol | |
| Dye 13 | | | | | | | | | | | | | $10^{-3}$ mol |
| Dyeing support (1) | (*) | (*) | (*) | (*) | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g | 100 g | 100 g | 100 g | 100 g |

(*): acidic dyeing support pH 4 (1): 50% A/50% B mixture

BUFFER solution A

| | |
|---|---|
| Alkyl (C8/C10 50/50) polyglucoside (2) in buffered 60% aqueous solution | 12 g |
| Demineralized water | 20 g |
| Pure absolute ethanol | 20 g |
| Benzyl alcohol | 4.0 g |
| Polyethylene glycol (8 EO) 400 | 3.0 g |
| Demineralized water | qs 100 g (30 g) |

BUFFER solution B

BUFFER P = 4
Ampoule TITRISOL [HOC(CO2H)(CH2CO2H)2] = 0.056 mol/l [NaOH] = 0.11 mol/l [HCl] = 0.044 mol/l
For the preparation of 500 ml of buffer with demineralized water The following dyeing results were obtained:

| | |
|---|---|
| Composition 1 | chromatic red |
| Composition 2 | dull brown |
| Composition 3 | beige brown |
| Composition 4 | mahogany yellow |
| Composition 5 | grey |
| Composition 6 | chromatic red |
| Composition 7 | brown |
| Composition 8 | light red |
| Composition 9 | light brown |
| Composition 10 | grey brown |
| Composition 11 | brown |
| Composition 12 | orange |
| Composition 13 | red |

Dyeing in Neutral Medium at pH=7
The following dyeing compositions were prepared:

| | |
|---|---|
| 96° ethyl alcohol | 20.8 g |
| Pentasodium salt of diethylenetriaminepentaacetic acid in aqueous solution at 40% | 0.48 g a.i. |
| $C_8$-$C_{10}$ alkyl polyglucoside in aqueous solution at 60% | 3.6 g a.i. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

For dyeings carried out under non-lightening conditions (without oxidant) these compositions were applied directly to the hair.

The following dyeing results were obtained:

| | |
|---|---|
| Composition 1 | intense chromatic red |
| Composition 2 | grey brown |
| Composition 3 | brown |
| Composition 4 | mahogany yellow |
| Composition 5 | intense grey |
| Composition 6 | chromatic red |
| Composition 7 | brown |
| Composition 8 | chromatic red |
| Composition 9 | light brown |
| Composition 10 | grey brown |
| Composition 11 | light red |

| Composition | 1 | 2 | 3 | 4 | 5 | 6 | 7 | 8 | 9 | 10 | 11 | 12 | 13 |
|---|---|---|---|---|---|---|---|---|---|---|---|---|---|
| Dye 1 | $10^{-3}$ mol | — | — | — | — | | | | | | | | |
| Dye 2 | — | $10^{-3}$ mol | — | — | — | | | | | | | | |
| Dye 3 | — | — | $10^{-3}$ mol | — | — | | | | | | | | |
| Dye 4 | — | — | — | $10^{-3}$ mol | — | — | | | | | | | |
| Dye 5 | — | — | — | — | $10^{-3}$ mol | — | | | | | | | |
| Dye 6 | — | — | — | — | — | $10^{-3}$ mol | | | | | | | |
| Dye 7 | | | | | | | $10^{-3}$ mol | | | | | | |
| Dye 8 | | | | | | | | $10^{-3}$ mol | | | | | |
| Dye 9 | | | | | | | | | $10^{-3}$ mol | | | | |
| Dye 10 | | | | | | | | | | $10^{-3}$ mol | | | |
| Dye 11 | | | | | | | | | | | $10^{-3}$ mol | | |
| Dye 12 | | | | | | | | | | | | $10^{-3}$ mol | |
| Dye 13 | | | | | | | | | | | | | $10^{-3}$ mol |
| Dyeing support (2) | (*) | (*) | (*) | (*) | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g | 100 g | 100 g | 100 g | 100 g |

(*): neutral support at pH 7:

-continued

| | |
|---|---|
| Composition 12 | red |
| Composition 13 | chromatic red |

For dyeings carried out under lightening conditions, an oxidant medium is used. In that case, at the time of use, each composition was mixed with an equal weight of 20-volumes hydrogen peroxide (6% by weight), which gave a final pH of 7.

Each composition was applied to locks of grey hair containing 90% white hairs, at a rate of 6 g of composition per 1 g of hair. After the composition was left on for 30 minutes, the locks were rinsed, washed with a standard shampoo, rinsed again and then dried.

The following dyeing results were obtained:

| | |
|---|---|
| Composition 1 | chromatic red |
| Composition 2 | grey brown |
| Composition 3 | light brown |
| Composition 4 | brown |
| Composition 5 | grey |
| Composition 6 | chromatic red |
| Composition 7 | light brown |
| Composition 8 | chromatic red |
| Composition 9 | light brown |
| Composition 10 | brown |
| Composition 11 | red |
| Composition 12 | orange |
| Composition 13 | chromatic red |

Dyeing in Basic Medium

The following dyeing compositions were prepared:

| | |
|---|---|
| 96° ethyl alcohol | 20.8 g |
| Pentasodium salt of diethylenetriaminepentaacetic acid in aqueous solution at 40% | 0.48 g a.i. |
| $C_8$-$C_{10}$ alkyl polyglucoside in aqueous solution at 60% | 3.6 g a.i. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

For dyeings carried out under non-lightening conditions (without oxidant), these compositions were applied directly to the hair.

The following dyeing results were obtained:

| | |
|---|---|
| Composition 1 | chromatic red |
| Composition 2 | light brown |
| Composition 3 | light brown |
| Composition 4 | rust brown |
| Composition 5 | grey |
| Composition 6 | chromatic red |
| Composition 7 | brown |
| Composition 8 | chromatic red |
| Composition 9 | brown |
| Composition 10 | red brown |
| Composition 11 | red |
| Composition 12 | light orange |
| Composition 13 | red |

What is claimed is:

1. A dyeing composition comprising, in an appropriate dyeing medium, at least one compound chosen from leuco

| Composition | 1 | 2 | 3 | 4 | 5 | 6 | 7 | 8 | 9 | 10 | 11 | 12 | 13 |
|---|---|---|---|---|---|---|---|---|---|---|---|---|---|
| Dye 1 | $10^{-3}$ mol | — | — | — | — | — | | | | | | | |
| Dye 2 | — | $10^{-3}$ mol | — | — | — | — | | | | | | | |
| Dye 3 | — | — | $10^{-3}$ mol | — | — | — | | | | | | | |
| Dye 4 | — | — | — | $10^{-3}$ mol | — | — | | | | | | | |
| Dye 5 | — | — | — | — | $10^{-3}$ mol | — | | | | | | | |
| Dye 6 | — | — | — | — | — | $10^{-3}$ mol | | | | | | | |
| Dye 7 | | | | | | | $10^{-3}$ mol | | | | | | |
| Dye 8 | | | | | | | | $10^{-3}$ mol | | | | | |
| Dye 9 | | | | | | | | | $10^{-3}$ mol | | | | |
| Dye 10 | | | | | | | | | | $10^{-3}$ mol | | | |
| Dye 11 | | | | | | | | | | | $10^{-3}$ mol | | |
| Dye 12 | | | | | | | | | | | | $10^{-3}$ mol | |
| Dye 13 | | | | | | | | | | | | | $10^{-3}$ mol |
| Dyeing support (3) | (*) | (*) | (*) | (*) | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g | 100 g | 100 g | 100 g | 100 g |

(*): dyeing support (3) pH 9.5:

compounds of formula (I), azomethine dyes with a pyrazolinone unit of formula (II), their mesomeric forms, and acid addition salts and solvates thereof:

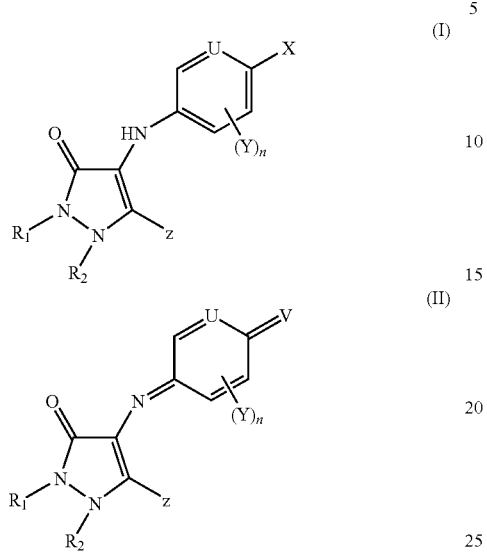

wherein:
n is an integer ranging from 0 to 3;
U is CR or N;
R is chosen from:
  a hydrogen atom;
  $C_1$-$C_4$ alkyl radicals optionally substituted by a hydroxyl radical,
  $C_1$-$C_4$ alkoxy radicals optionally substituted by a hydroxyl radical; and
  (di)alkyl($C_1$-$C_4$)amino radicals wherein the alkyl moiety is optionally substituted by a hydroxyl radical;
X is chosen from:
  a hydroxyl radical; and
  $NR'_1R''_2$ radicals, wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; phenyl radicals optionally substituted by at least one radical chosen from hydroxyl, amino, and ($C_1$-$C_2$)alkoxy radicals; and
  when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, carboxamide, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;
  when X is $NHR'_1$ and when U is CR wherein R is an alkoxy radical, then X and U may form a 6-membered ring of morpholine type which is optionally substituted by at least one $C_1$-$C_4$ alkyl group,
V is chosen from:
  an oxygen atom;
  $NR'_1$ radicals wherein $R'_1$ is chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$)amino radicals; and phenyl radicals optionally substituted by at least one radical chosen from hydroxyl, amino, and ($C_1$-$C_2$)alkoxy radicals,
  $N^+R'_1R''_1$ radicals wherein $R'_1$ and $R''_1$ are each independently chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$) amino radicals; and phenyl radicals optionally substituted by at least one radical chosen from hydroxyl, amino, and ($C_1$-$C_2$)alkoxy radicals;
  when V is $N^+R'_1R''_1$ the electroneutrality of the structure (II) is ensured by an anion An-;
  when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;
  when V is $NR'_1$ and when U is CR wherein R is an alkoxy radical, then V and U may form a 6-membered ring of morpholine type which is optionally substituted by at least one $C_1$-$C_4$ alkyl group,
each instance of Y, which may be identical or different, is chosen from:
  a hydroxyl radical;
  $C_1$-$C_4$ alkyl radicals;
  $C_1$-$C_4$ hydroxyalkyl radicals;
  halogen atoms;
  an oxygen atom substituted by a radical chosen from $C_1$-$C_4$ alkyl, aryl, and heteroaryl radicals, it being possible for the $C_1$-$C_4$ alkyl, aryl, and heteroaryl radicals to be substituted by at least one hydroxyl radical;
  $NR'_2R'_3$ radicals;
  wherein $R'_2$ and $R'_3$, which are identical or different, arechosen from
  a hydrogen atom;
  $C_1$-$C_4$ alkylcarbonyl radicals optionally substituted by a quaternary ammonium group or by a cationic or non-cationic nitrogen-containing heterocycle, wherein these nitrogen-containing heterocycles are optionally substituted by at least one $C_1$-$C_4$ alkyl radical;
  aminocarbonyl radicals;
  $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and
  phenyl radicals optionally substituted by at least one radical chosen from hydroxyl, amino, and ($C_1$-$C_2$) alkoxy radicals;
  $R'_2$ and $R'_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals; and when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, optionally substituted by at least one $C_1$-$C_4$ alkyl radical;

Z is chosen from:
  linear and branched $C_1$-$C_4$ alkyl radicals;
  $NR_3R_4$ radicals; and
  $OR_5$ radicals;

$R_1$, $R_2$, $R_3$, $R_4$ and $R_5$, which are identical or different, are chosen from:
  $C_1$-$C_6$ alkyl radicals optionally substituted by at least one radical chosen from $OR_6$, $NR_7R_8$, carboxyl, $C_1$-$C_4$ alkyl carboxylate, sulfonic, (di)alkylcarboxamido $CONR_7R_8$, sulfonamido $SO_2NR_7R_8$ radicals; and 5- or 6-membered heteroaryl and phenyl radicals optionally substituted by at least one radical chosen from ($C_1$-$C_4$)alkyl, hydroxyl, $C_1$-$C_2$ alkoxy, amino, (di)alkyl($C_1$-$C_2$)amino and $C_1$-$C_4$ hydroxyalkyl radicals;
  phenyl radicals optionally substituted by at least one radical chosen from ($C_1$-$C_4$)alkyl, hydroxy($C_1$-$C_4$) alkyl, hydroxyl, $C_1$-$C_2$ alkoxy, amino, and (di)alkyl ($C_1$-$C_2$)amino radicals;
  5- or 6-membered heteroaryl radicals optionally substituted by at least one radical chosen from ($C_1$-$C_4$)alkyl radicals and ($C_1$-$C_2$)alkoxy radicals;

$R_3$, $R_4$ and $R_5$ may also be chosen from a hydrogen atom;

$R_6$, $R_7$ and $R_8$, which are identical or different, are chosen from a hydrogen atom; linear and branched $C_1$-$C_4$ alkyl radicals optionally substituted by at least one radical chosen from hydroxyl, $C_1$-$C_2$ alkoxy, (di)alkylcarboxamido $CONR_9R_{10}$, sulfonyl $SO_2R_9$, and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals; and phenyl radicals optionally substituted by at least one radical chosen from ($C_1$-$C_4$)alkyl, a hydroxyl radical, $C_1$-$C_2$ alkoxy, amino, and (di)alkyl($C_1$-$C_2$)amino radicals;

$R_7$ and $R_8$, which are identical or different, are chosen from (di)alkylcarboxamido $CONR_9R_{10}$ radicals and sulfonyl $SO_2R_9$ radicals;

$R_9$ and $R_{10}$, which are identical or different, are chosen from a hydrogen atom, and linear and branched $C_1$-$C_4$ alkyl radicals optionally substituted by at least one radical chosen from a hydroxyl radical and $C_1$-$C_2$ alkoxy radicals;

$R_1$ and $R_2$, and independently $R_3$ and $R_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl($C_1$-$C_4$) amino, (di)hydroxyalkyl($C_1$-$C_4$)amino, hydroxyl, carboxyl, (di)alkylcarboxamido, ($C_1$-$C_2$)alkoxy, and $C_1$-$C_4$ alkyl radicals optionally substituted by at least one radical chosen from hydroxyl, amino, (di)alkyl($C_1$-$C_4$) amino, $C_1$-$C_2$ alkoxy, carboxyl, and sulfonyl radicals;

An- is an anion or a mixture of anions which allows the electroneutrality of the structures to be ensured;

with the proviso that, when Z is an alkyl radical, $R_1$ is not an optionally substituted phenyl radical and $R_2$ is not an alkyl radical;

with the exception of the following compound:

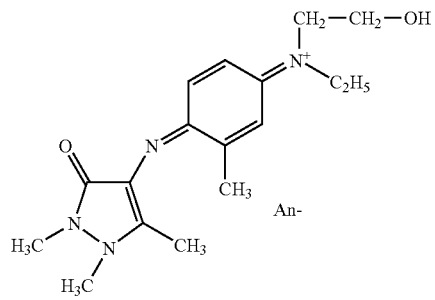

and also its mesomeric forms, its acid addition salts and its solvates thereof.

2. The composition according to claim 1, wherein the at least one compound is chosen from leuco compounds of formula (I), azomethine dyes with a pyrazolinone unit of formula (II), their mesomeric forms, acid addition salts and solvates thereof:

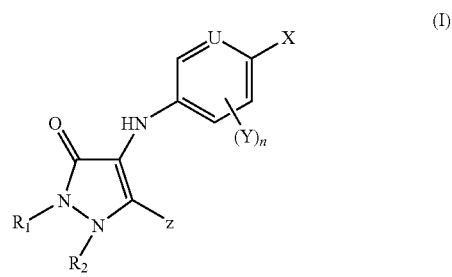

(I)

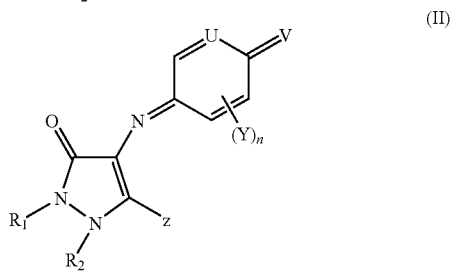

(II)

wherein:
  n is an integer ranging from 0 to 3;
  U is CR or N;
  R is chosen from:
    a hydrogen atom;
    $C_1$-$C_4$ alkyl radicals optionally substituted by a hydroxyl radical;
    $C_1$-$C_4$ alkoxy radicals optionally substituted by a hydroxyl radical; and
    (di)alkyl($C_1$-$C_4$)amino radicals wherein the alkyl moiety is optionally substituted by a hydroxyl radical;
  X is chosen from:
    a hydroxyl radical; and
    $NR'_1R''_1$ wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; phenyl radicals optionally substituted by at least one radical chosen from hydroxyl, amino, and ($C_1$-$C_2$)alkoxy radicals; and when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, carboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;

when X is $NHR'_1$ and when U is a group CR wherein R is an alkoxy radical, then X and U may form a 6-membered ring of morpholine type which is optionally substituted by at least one $C_1$-$C_4$ alkyl group;

V is chosen from:
  an oxygen atom;
  $NR'_1$ radicals wherein $R'_1$ is chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$)amino radicals; and phenyl radicals optionally substituted by at least one radical chosen from hydroxyl, amino, and ($C_1$-$C_2$)alkoxy radicals; and
  $N^+R'_1R''_1$ wherein $R'_1$ and $R''_1$ are independently chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$)amino radicals; and phenyl radicals optionally substituted by at least one radical chosen from hydroxyl, amino, and ($C_1$-$C_2$)alkoxy radicals;
  when V is $N^+R'_1R''_1$, the electroneutrality of the structure (II) is ensured by an anion An-,
  when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;
  when V is $NR'_1$ and when U is CR wherein R is an alkoxy radical, then V and U may form a 6-membered ring of morpholine type which is optionally substituted by at least one $C_1$-$C_4$ alkyl group, each instance of Y, which may be identical or different, is chosen from:
  a hydroxyl radical;
  $C_1$-$C_4$ alkyl radicals;
  $C_1$-$C_4$ hydroxyalkyl radicals;
  halogen atoms;
  an oxygen atom substituted by a radical chosen from a $C_1$-$C_4$ alkyl, aryl and heteroaryl radical, it being possible for the $C_1$-$C_4$ alkyl, aryl and heteroaryl radical to be substituted by at least one hydroxyl radical; and
  $NR'_2R''_3$;
    wherein $R'_2$ and $R'_3$, which are identical or different, are chosen from:
      a hydrogen atom;
      $C_1$-$C_4$ alkylcarbonyl radicals optionally substituted by a quaternary ammonium group or by a cationic or non-cationic nitrogen-containing heterocycle, wherein these nitrogen-containing heterocycles are substituted by at least one $C_1$-$C_4$ alkyl radical;
      aminocarbonyl radicals;
      $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and
      phenyl radicals optionally substituted by at least one radical chosen from hydroxyl, amino, and ($C_1$-$C_2$) alkoxy radicals;
    $R'_2$ and $R'_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals; and when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, optionally substituted by at least one $C_1$-$C_4$ alkyl radical;

Z is chosen from:
  $NR_3R_4$ radicals; and
  $OR_5$ radicals;

$R_1$, $R_2$, $R_3$, $R_4$ and $R_5$, which are identical or different, are chosen from:
  $C_1$-$C_6$ alkyl radicals optionally substituted by at least one radical chosen from $OR_6$ radicals, $NR_7R_8$ radicals, carboxyl radicals, $C_1$-$C_4$ alkyl carboxylate radicals, sulfonic radicals, (di)alkylcarboxamido $CONR_7R_8$ radicals, sulfonamido $SO_2NR_7R_8$ radicals; and 5- or 6-membered heteroaryl and phenyl radicals optionally substituted by at least one radical chosen from ($C_1$-$C_4$)alkyl, hydroxyl, $C_1$-$C_2$ alkoxy, amino, (di)alkyl($C_1$-$C_2$)amino and $C_1$-$C_4$ hydroxyalkyl radicals;
  phenyl radicals optionally substituted by at least one radical chosen from ($C_1$-$C_4$)alkyl, hydroxy($C_1$-$C_4$)alkyl, hydroxyl, $C_1$-$C_2$ alkoxy, amino, and (di)alkyl($C_1$-$C_2$)amino radicals; and
  5- or 6-membered heteroaryl radicals optionally substituted by at least one radical chosen from ($C_1$-$C_4$)alkyl radicals and ($C_1$-$C_2$)alkoxy radicals;

$R_3$, $R_4$ and $R_5$ may also be chosen from a hydrogen atom;

$R_6$, $R_7$ and $R_8$, which are identical or different, are chosen from a hydrogen atom; linear and branched $C_1$-$C_4$ alkyl radicals optionally substituted by at least one radical chosen from hydroxyl, $C_1$-$C_2$ alkoxy, (di)alkylcarboxamido $CONR_9R_{10}$, sulfonyl $SO_2R_9$, and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals; and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals;

R$_7$ and R$_8$, which are identical or different, may also be chosen from (di)alkylcarboxamido CONR$_9$R$_{10}$ radicals and sulfonyl SO$_2$R$_9$ radicals;

R$_9$ and R$_{10}$, which are identical or different, are chosen from a hydrogen atom, and linear and branched C$_1$-C$_4$ alkyl radicals optionally substituted by at least one radical chosen from a hydroxyl radical and C$_1$-C$_2$ alkoxy radicals;

R$_1$ and R$_2$, and independently R$_3$ and R$_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl(C$_1$-C$_4$)amino, (di)hydroxyalkyl(C$_1$-C$_4$)amino, hydroxyl, carboxyl, (di)alkylcarboxamido, (C$_1$-C$_2$)alkoxy, and C$_1$-C$_4$ alkyl radicals optionally substituted by at least one radical chosen from hydroxyl, amino, (di)alkyl(C$_1$-C$_4$) amino, C$_1$-C$_2$ alkoxy, carboxyl, and sulfonyl radicals; and An- is an anion or a mixture of anions which allows the electroneutrality of the structures to be ensured.

3. The composition according to claim 1, wherein R$_1$ and R$_2$ of formula (I), which are identical or different, are chosen from:
C$_1$-C$_4$ alkyl radicals optionally substituted by at least one radical chosen from hydroxyl, (C$_1$-C$_2$)alkoxy, amino, and (di)alkyl(C$_1$-C$_2$)amino radicals; and
phenyl radicals optionally substituted by at least one radical chosen from C$_1$-C$_4$ alkyl radicals and C$_1$-C$_4$ hydroxyalkyl radicals.

4. The composition according to claim 3, wherein R$_1$ and R$_2$ of formula (I), which are identical or different, are chosen from methyl, ethyl, 2-hydroxyethyl, 3-hydroxypropyl, 2-hydroxypropyl, and phenyl radicals.

5. The composition according to claim 1, wherein R$_1$ and R$_2$ form, together with the nitrogen atoms to which they are attached, a saturated or unsaturated 5- or 6-membered ring which is optionally substituted.

6. The composition according to claim 5, wherein R$_1$ and R$_2$ form, together with the nitrogen atoms to which they are attached, a pyrazolidine, pyridazolidine, triazepine ring optionally substituted by at least one radical chosen from C$_1$-C$_4$ alkyl, hydroxyl, (C$_1$-C$_2$)alkoxy, carboxyl, (di)alkylcarboxamido, amino, and (di)alkyl(C$_1$-C$_2$)amino radicals.

7. The composition according to claim 1, wherein Z of formula (I) or (II), is chosen from NR$_3$R$_4$ radicals.

8. The composition according to claim 7, wherein R$_3$ and R$_4$, which are identical or different, are chosen from a hydrogen atom; C$_1$-C$_4$ alkyl radicals optionally substituted by at least one radical chosen from hydroxyl, (C$_1$-C$_2$)alkoxy, amino, (di)alkyl(C$_1$-C$_2$)amino, carboxyl, and C$_1$-C$_4$ alkyl carboxylate radicals; and phenyl radicals optionally substituted by at least one radical chosen from hydroxyl, amino, and (C$_1$-C$_2$)alkoxy radicals.

9. The composition according to claim 8, wherein R$_3$ and R$_4$, which are identical or different, are chosen from a hydrogen atom; methyl, ethyl, isopropyl, 2-hydroxyethyl, 3-hydroxypropyl, and 2-hydroxypropyl radicals; ethyl radicals substituted by an ethyl carboxylate radical; and ethyl radicals substituted by a carboxyl radical.

10. The composition according to claim 1, wherein Z is chosen from NR$_3$R$_4$ radicals, wherein R$_3$ and R$_4$ form, together with the nitrogen atom to which they are attached, a heterocyclic ring of 5 to 7 members chosen from pyrrolidine, piperidine, homopiperidine, piperazine, homopiperazine, and morpholine; wherein the heterocycles may be substituted by at least one radical chosen from hydroxyl, amino, (di)alkyl (C$_1$-C$_2$)amino, (di)hydroxy-alkyl(C$_1$-C$_2$)amino, (di)alkyl (C$_1$-C$_2$)carboxamido, carboxyl, and C$_1$-C$_4$ alkyl radicals optionally substituted by at least one radical chosen from hydroxyl, amino, and C$_1$-C$_2$ (di)alkylamino radicals.

11. The composition according to claim 10, wherein R$_3$ and R$_4$ form, together with the nitrogen atom to which they are attached, a 5- to 7-membered ring chosen from pyrrolidine, 3-hydroxypyrrolidine, 3-aminopyrrolidine, 3-dimethyl-aminopyrrolidine, pyrrolidine-2-carboxylic acid, 3-hydroxypyrrolidine-2-carboxylic acid, piperidine, 4-hydroxypiperidine, homopiperidine, homopiperazine, N-methylhomopiperazine, N-(2-hydroxyethyl)homopiper-azine, and morpholine.

12. The composition according to claim 1, wherein Z is a radical chosen from methyl, amino, ethylamino, isopropylamino, and pyrrolidine radicals.

13. The composition according to claim 1, wherein U is CR or N, and R is chosen from a hydrogen atom, and methyl, methoxy, 2-hydroxyethoxy, methylamino, dimethylamino, hydroxyethylamino, dihydroxyethylamino, and methyl(hydroxyethyl)amino radicals.

14. The composition according to claim 1, wherein X is chosen from hydroxyl radicals and NR'$_1$R"$_1$ radicals, wherein R'$_1$ and R"$_1$ are each independently chosen from a hydrogen atom and C$_1$-C$_6$ alkyl radicals optionally substituted by at least one hydroxyl radical.

15. The composition according to claim 1, wherein X is chosen from NR'$_1$ R"$_1$ radicals, wherein R'$_1$ and R"$_1$ form a heterocycle chosen from pyrrolidine, piperidine, homopiperidine, piperazine, homopiperazine, and morpholine; wherein the heterocycles may be substituted by at least one radical chosen from halogen atoms, amino, (di)alkyl(C$_1$-C$_4$)amino, hydroxyl, carboxyl, (di)alkylcarboxamido, (C$_1$-C$_2$)alkoxy, and C$_1$-C$_4$ alkyl radicals which are optionally substituted by at least one radical chosen from hydroxyl, amino, (di)alkylamino, alkoxy, carboxyl, and sulfonyl radicals.

16. The composition according to claim 1, wherein V of formula (I) and (II) is chosen from an oxygen atom; NR'$_1$ radicals wherein R'$_1$ is chosen from a hydrogen atom and C$_1$-C$_6$ alkyl radicals optionally substituted by at least one hydroxyl radical; N+R'$_1$R"$_1$ radicals wherein R'$_1$ and R"$_1$ are each independently chosen from a hydrogen atom, and C$_1$-C$_6$ alkyl radicals optionally substituted by at least one hydroxyl radical, or wherein R'$_1$ and R"$_1$ may form, together with the nitrogen atom to which they are attached, a saturated or unsaturated heterocycle comprising 5 to 7 members.

17. The composition according to claim 1, wherein Y, which are identical or different, are chosen from a hydroxyl radical; C$_1$-C$_4$ alkyl radicals; halogen atoms; an oxygen atom substituted by a C$_1$-C$_4$ alkyl radical that may be substituted by at least one hydroxyl radical; NR'$_2$R'$_3$; R'$_2$ and R'$_3$, which are identical or different, may be chosen from a hydrogen atom; and C$_1$-C$_4$ alkylcarbonyl radicals optionally substituted by a quaternary ammonium group or R'$_2$ and R'$_3$ may form, together with the nitrogen atom to which they are attached, a saturated heterocycle comprising 5 to 7 members.

18. The composition according to claim 1, wherein the composition further comprises at least one oxidant.

19. A compound chosen from leuco compounds of formula (I), azomethine dyes with a pyrazolinone unit of formula (II), their mesomeric forms, acid addition salts and solvates thereof:

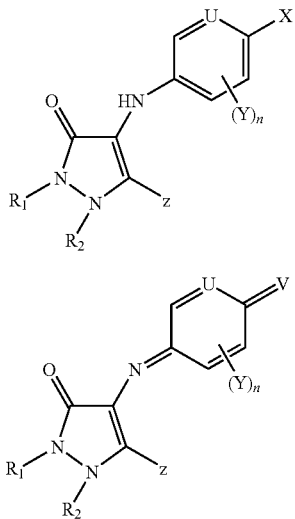

n is an integer ranging from 0 to 3;
U is CR or N;
R is chosen from:
  a hydrogen atom;
  $C_1$-$C_4$ alkyl radicals optionally substituted by a hydroxyl radical,
  $C_1$-$C_4$ alkoxy radicals optionally substituted by a hydroxyl radical; and
  (di)alkyl($C_1$-$C_4$)amino radicals wherein the alkyl moiety is optionally substituted by a hydroxyl radical;
X is chosen from:
  a hydroxyl radical; and
  $NR'_1R''_1$ radicals, wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; phenyl radicals optionally substituted by at least one radical chosen from hydroxyl, amino, and ($C_1$-$C_2$)alkoxy radicals; and
  when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, carboxamide, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;
  when X is $NHR'_1$ and when U is CR wherein R is an alkoxy radical, then X and U may form a 6-membered ring of morpholine type which is optionally substituted by at least one $C_1$-$C_4$ alkyl group,
V is chosen from:
  an oxygen atom;
  $NR'_1$ radicals wherein $R'_1$ is chosen from a hydrogen atom; $C_1$-$C_6$ alkyl radicals optionally substituted by at least one radical chosen from hydroxyl, ($C_1$-$C_2$)alkoxy, amino, and (di)alkyl($C_1$-$C_2$)amino radicals;
  and phenyl radicals optionally substituted by at least one radical chosen from hydroxyl, amino, and ($C_1$-$C_2$)alkoxy radicals,
  $N^+R'_1R''_1$ radicals wherein $R'_1$ and $R''_1$ are each independently chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$) amino radicals; and phenyl radicals optionally substituted by at least one radical chosen from hydroxyl, amino, and ($C_1$-$C_2$)alkoxy radicals;
  when V is $N^+R'_1R''_1$, the electroneutrality of the structure (II) is ensured by an anion An-;
  when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di) alkylamino, alkoxy, carboxyl, and sulfonyl radicals;
  when V is $NR'_1$ and when U is CR wherein R is an alkoxy radical, then V and U may form a 6-membered ring of morpholine type which is optionally substituted by at least one $C_1$-$C_4$ alkyl group,
each instance of Y, which may be identical or different, is chosen from:
  a hydroxyl radical;
  $C_1$-$C_4$ alkyl radicals;
  $C_1$-$C_4$ hydroxyalkyl radicals;
  halogen atoms;
  an oxygen atom substituted by a radical chosen from $C_1$-$C_4$ alkyl, aryl, and heteroaryl radicals, it being possible for the $C_1$-$C_4$ alkyl, aryl, and heteroaryl radicals to be substituted by at least one hydroxyl radical;
  $NR'_2R'_3$ radicals;
  wherein $R'_2$ and $R'_3$, which are identical or different, are chosen from
  a hydrogen atom;
  $C_1$-$C_4$ alkylcarbonyl radicals optionally substituted by a quaternary ammonium group or by a cationic or non-cationic nitrogen-containing heterocycle, wherein these nitrogen-containing heterocycles are optionally substituted by at least one $C_1$-$C_4$ alkyl radical;
  aminocarbonyl radicals;
  $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and
  phenyl radicals optionally substituted by at least one radical chosen from hydroxyl, amino, and ($C_1$-$C_2$) alkoxy radicals;
  $R'_2$ and $R'_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals; and when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, optionally substituted by at least one $C_1$-$C_4$ alkyl radical;

Z is chosen from:
linear and branched $C_1$-$C_4$ alkyl radicals;
$NR_3R_4$ radicals; and
$OR_5$ radicals;

$R_1$, $R_2$, $R_3$, $R_4$ and $R_5$, which are identical or different, are chosen from:
$C_1$-$C_6$ alkyl radicals optionally substituted by at least one radical chosen from $OR_6$, $NR_7R_8$, carboxyl, $C_1$-$C_4$ alkyl carboxylate, sulfonic, (di)alkylcarboxamido $CONR_7R_8$, sulfonamido $SO_2NR_7R_8$ radicals; and 5- or 6-membered heteroaryl and phenyl radicals optionally substituted by at least one radical chosen from ($C_1$-$C_4$)alkyl, hydroxyl, $C_1$-$C_2$ alkoxy, amino, (di)alkyl($C_1$-$C_2$)amino and $C_1$-$C_4$ hydroxyalkyl radicals;

phenyl radicals optionally substituted by at least one radical chosen from ($C_1$-$C_4$)alkyl, hydroxy($C_1$-$C_4$) alkyl, hydroxyl, $C_1$-$C_2$ alkoxy, amino, and (di)alkyl ($C_1$-$C_2$)amino radicals;

5- or 6-membered heteroaryl radicals optionally substituted by at least one radical chosen from ($C_1$-$C_4$)alkyl radicals and ($C_1$-$C_2$)alkoxy radicals;

$R_3$, $R_4$ and $R_5$ may also be chosen from a hydrogen atom;

$R_6$, $R_7$ and $R_8$, which are identical or different, are chosen from a hydrogen atom; linear and branched $C_1$-$C_4$ alkyl radicals optionally substituted by at least one radical chosen from hydroxyl, $C_1$-$C_2$ alkoxy, (di)alkylcarboxamido $CONR_9R_{10}$, sulfonyl $SO_2R_9$, and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals; and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals;

$R_7$ and $R_8$, which are identical or different, are chosen from (di)alkylcarboxamido $CONR_9R_{10}$ radicals and sulfonyl $SO_2R_9$ radicals;

$R_9$ and $R_{10}$, which are identical or different, are chosen from a hydrogen atom, and linear and branched $C_1$-$C_4$ alkyl radicals optionally substituted by at least one radical chosen from a hydroxyl radical and $C_1$-$C_2$ alkoxy radicals;

$R_1$ and $R_2$, and independently $R_3$ and $R_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl($C_1$-$C_4$) amino, (di)hydroxyalkyl($C_1$-$C_4$)amino, hydroxyl, carboxyl, (di)alkylcarboxamido, ($C_1$-$C_2$)alkoxy, and $C_1$-$C_4$ alkyl radicals optionally substituted by at least one radical chosen from hydroxyl, amino, (di)alkyl($C_1$-$C_4$) amino, $C_1$-$C_2$ alkoxy, carboxyl, and sulfonyl radicals;

An- is an anion or a mixture of anions which allows the electroneutrality of the structures to be ensured;

with the proviso that, when Z is an alkyl radical, $R_1$ is not an optionally substituted phenyl radical and $R_2$ is not an alkyl radical;

with the exception of the following compound:

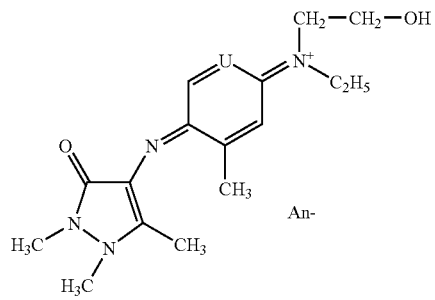

and also its mesomeric forms, its acid addition salts and its solvates thereof.

20. A method for dyeing keratin fibers, comprising applying to the keratin fibers at least one dyeing composition comprising at least one compound chosen from leuco compounds of formula (I), azomethine dyes with a pyrazolinone unit of formula (II), their mesomeric forms, acid addition salts and solvates thereof:

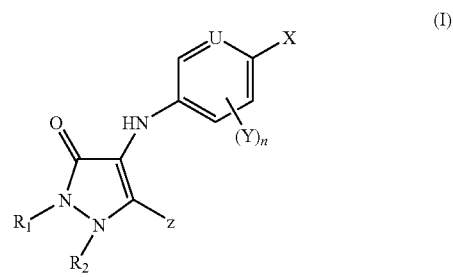

(I)

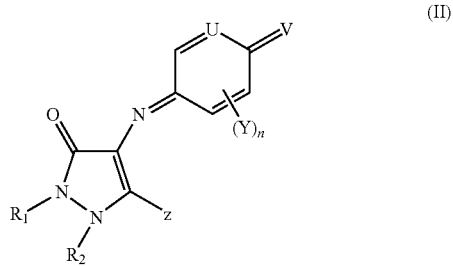

(II)

wherein:
n is an integer ranging from 0 to 3;
U is CR or N;
R is chosen from:
a hydrogen atom;
$C_1$-$C_4$ alkyl radicals optionally substituted by a hydroxyl radical,
$C_1$-$C_4$ alkoxy radicals optionally substituted by a hydroxyl radical; and
(di)alkyl($C_1$-$C_4$)amino radicals wherein the alkyl moiety is optionally substituted by a hydroxyl radical;
X is chosen from:
a hydroxyl radical; and
$NR'_1R''_1$ radicals, wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino, and (di)alkyl ($C_1$-$C_2$)amino radicals; phenyl radicals optionally substituted by at least one radical chosen from hydroxyl, amino, and ($C_1$-$C_2$)alkoxy radicals; and when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, carboxamide, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;

when X is $NHR'_1$ and when U is CR wherein R is an alkoxy radical, then X and U may form a 6-membered ring of morpholine type which is optionally substituted by at least one $C_1$-$C_4$ alkyl group, V is chosen from:
  an oxygen atom;
  $NR'_1$ radicals wherein $R'_1$ is chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$)amino radicals; and phenyl radicals optionally substituted by at least one radical chosen from hydroxyl, amino, and ($C_1$-$C_2$)alkoxy radicals,
  $N^+R'_1R''_1$ radicals wherein $R'_1$ and $R''_1$ are each independently chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$) amino radicals; and phenyl radicals optionally substituted by at least one radical chosen from hydroxyl, amino, and ($C_1$-$C_2$)alkoxy radicals;
  when V is $N^+R'_1R''_1$ the electroneutrality of the structure (II) is ensured by an anion An-;
  when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di) alkylamino, alkoxy, carboxyl, and sulfonyl radicals;
  when V is $NR'_1$ and when U is CR wherein R is an alkoxy radical, then V and U may form a 6-membered ring of morpholine type which is optionally substituted by at least one $C_1$-$C_4$ alkyl group, each instance of Y, which may be identical or different, is chosen from:
  a hydroxyl radical;
  $C_1$-$C_4$ alkyl radicals;
  $C_1$-$C_4$ hydroxyalkyl radicals;
  halogen atoms;
  an oxygen atom substituted by a radical chosen from $C_1$-$C_4$ alkyl, aryl, and heteroaryl radicals, it being possible for the $C_1$-$C_4$ alkyl, aryl, and heteroaryl radicals to be substituted by at least one hydroxyl radical;
  $NR'_2R'_3$ radicals;
    wherein $R'_2$ and $R'_3$, which are identical or different, arechosen from
      a hydrogen atom;
      $C_1$-$C_4$ alkylcarbonyl radicals optionally substituted by a quaternary ammonium group or by a cationic or non-cationic nitrogen-containing heterocycle, wherein these nitrogen-containing heterocycles are optionally substituted by at least one $C_1$-$C_4$ alkyl radical;
      aminocarbonyl radicals;
      $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and
      phenyl radicals optionally substituted by at least one radical chosen from hydroxyl, amino, and ($C_1$-$C_2$) alkoxy radicals;
    $R'_2$ and $R'_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals; and
  when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, optionally substituted by at least one $C_1$-$C_4$ alkyl radical;

Z is chosen from:
  linear and branched $C_1$-$C_4$ alkyl radicals;
  $NR_3R_4$ radicals; and
  $OR_5$ radicals;

$R_1$, $R_2$, $R_3$, $R_4$ and $R_5$, which are identical or different, are chosen from:
  $C_1$-$C_6$ alkyl radicals optionally substituted by at least one radical chosen from $OR_6$, $NR_7R_8$, carboxyl, $C_1$-$C_4$ alkyl carboxylate, sulfonic, (di)alkylcarboxamido $CONR_7R_8$, sulfonamido $SO_2NR_7R_8$ radicals; and 5- or 6-membered heteroaryl and phenyl radicals optionally substituted by at least one radical chosen from ($C_1$-$C_4$)alkyl, hydroxyl, $C_1$-$C_2$ alkoxy, amino, (di)alkyl($C_1$-$C_2$)amino and $C_1$-$C_4$ hydroxyalkyl radicals;
  phenyl radicals optionally substituted by at least one radical chosen from ($C_1$-$C_4$)alkyl, hydroxy($C_1$-$C_4$) alkyl, hydroxyl, $C_1$-$C_2$ alkoxy, amino, and (di)alkyl ($C_1$-$C_2$)amino radicals;
  5- or 6-membered heteroaryl radicals optionally substituted by at least one radical chosen from ($C_1$-$C_4$)alkyl radicals and ($C_1$-$C_2$)alkoxy radicals;

$R_3$, $R_4$ and $R_5$ may also be chosen from a hydrogen atom;

$R_6$, $R_7$ and $R_8$, which are identical or different, are chosen from a hydrogen atom; linear and branched $C_1$-$C_4$ alkyl radicals optionally substituted by at least one radical chosen from hydroxyl, $C_1$-$C_2$ alkoxy, (di)alkylcarboxamido $CONR_9R_{10}$, sulfonyl $SO_2R_9$, and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals; and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals;

$R_7$ and $R_8$, which are identical or different, are chosen from (di)alkylcarboxamido $CONR_9R_{10}$ radicals and sulfonyl $SO_2R_9$ radicals;

$R_9$ and $R_{10}$, which are identical or different, are chosen from a hydrogen atom, and linear and branched $C_1$-$C_4$ alkyl radicals optionally substituted by at least one radical chosen from a hydroxyl radical and $C_1$-$C_2$ alkoxy radicals;

$R_1$ and $R_2$, and independently $R_3$ and $R_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl($C_1$-$C_4$) amino, (di)hydroxyalkyl($C_1$-$C_4$)amino, hydroxyl, carboxyl, (di)alkylcarboxamido, ($C_1$-$C_2$)alkoxy, and $C_1$-$C_4$ alkyl radicals optionally substituted by at least one radical chosen from hydroxyl, amino, (di)alkyl($C_1$-$C_4$) amino, $C_1$-$C_2$ alkoxy, carboxyl, and sulfonyl radicals;

An- is an anion or a mixture of anions which allows the electroneutrality of the structures to be ensured;

with the exception of the following compounds:

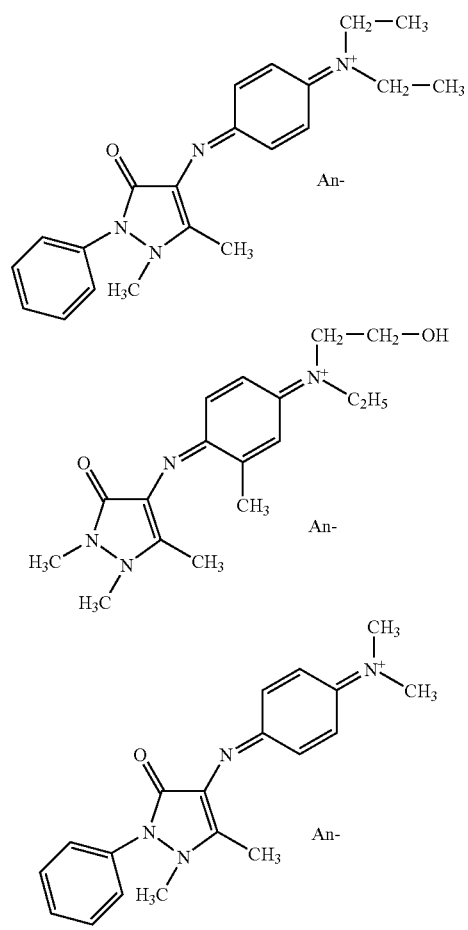

and also their mesomeric forms, their acid addition salts and their solvates thereof.

21. The method according to claim 20, wherein the at least one composition comprises compounds of formula (II).

22. A multi-compartment device comprising, in at least one first compartment, at least one composition comprising at least one compound of formula (I) and in at least one second compartment, at least one oxidant, and optionally a compound of formula (II), and at least one alkaline agent, wherein the at least one compound is chosen from leuco compounds of formula (I), azomethine dyes with a pyrazolinone unit of formula (II), their mesomeric forms, acid addition salts and solvates thereof:

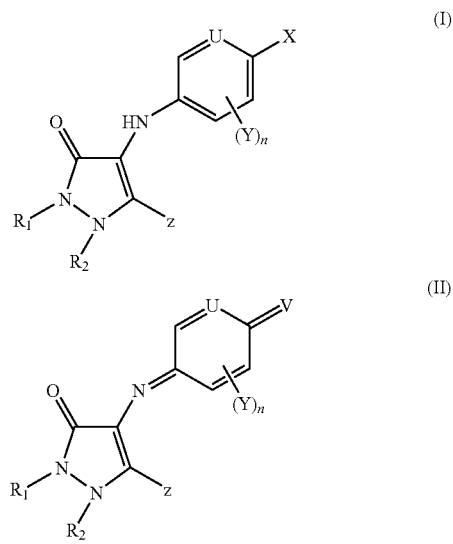

wherein:
n is an integer ranging from 0 to 3;
U is CR or N;
R is chosen from:
 a hydrogen atom;
 $C_1$-$C_4$ alkyl radicals optionally substituted by a hydroxyl radical,
 $C_1$-$C_4$ alkoxy radicals optionally substituted by a hydroxyl radical; and
 (di)alkyl($C_1$-$C_4$)amino radicals wherein the alkyl moiety is optionally substituted by a hydroxyl radical;
X is chosen from:
 a hydroxyl radical; and
 $NR'_1R''_1$ radicals, wherein $R'_1$ and $R''_1$ are independently chosen from a hydrogen atom; $C_1$-$C_6$ alkyl radicals optionally substituted by at least one radical chosen from hydroxyl, ($C_1$-$C_2$)alkoxy, amino, and (di)alkyl ($C_1$-$C_2$)amino radicals; phenyl radicals optionally substituted by at least one radical chosen from hydroxyl, amino, and ($C_1$-$C_2$)alkoxy radicals; and
 when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, carboxamide, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;
 when X is $NHR'_1$ and when U is CR wherein R is an alkoxy radical, then X and U may form a 6-membered ring of morpholine type which is optionally substituted by at least one $C_1$-$C_4$ alkyl group,
V is chosen from:
 an oxygen atom;
 $NR'_1$ radicals wherein $R'_1$ is chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$)amino radicals; and phenyl radicals optionally substituted by at least one radical chosen from hydroxyl, amino, and ($C_1$-$C_2$)alkoxy radicals, $N^+R'_1R''_1$ radicals wherein $R'_1$ and $R''_1$ are each independently chosen from a hydrogen atom; $C_1$-$C_6$ alkyl radicals optionally substituted by at least one radical chosen from hydroxyl, ($C_1$-$C_2$) alkoxy, amino, and (di)alkyl($C_1$-$C_2$) amino radicals; and phenyl radicals optionally substituted by at least one radical chosen from hydroxyl, amino, and ($C_1$-$C_2$)alkoxy radicals;

when V is $N^+R'_1R''_1$ the electroneutrality of the structure (II) is ensured by an anion An-;

when $R'_1$ and $R''_1$ are other than hydrogen, $R'_1$ and $R''_1$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals;

when V is $NR'_1$ and when U is CR wherein R is an alkoxy radical, then V and U may form a 6-membered ring of morpholine type which is optionally substituted by at least one $C_1$-$C_4$ alkyl group, each instance of Y, which may be identical or different, is chosen from:
  a hydroxyl radical;
  $C_1$-$C_4$ alkyl radicals;
  $C_1$-$C_4$ hydroxyalkyl radicals;
  halogen atoms;
  an oxygen atom substituted by a radical chosen from $C_1$-$C_4$ alkyl, aryl, and heteroaryl radicals, it being possible for the $C_1$-$C_4$ alkyl, aryl, and heteroaryl radicals to be substituted by at least one hydroxyl radical;
  $NR'_2R'_3$ radicals;
  wherein $R'_2$ and $R'_3$, which are identical or different, arechosen from
  a hydrogen atom;
  $C_1$-$C_4$ alkylcarbonyl radicals optionally substituted by a quaternary ammonium group or by a cationic or non-cationic nitrogen-containing heterocycle, wherein these nitrogen-containing heterocycles are optionally substituted by at least one $C_1$-$C_4$ alkyl radical;
  aminocarbonyl radicals;
  $C_1$-$C_6$ alkyl radicals optionally substituted by at least one radical chosen from hydroxyl, ($C_1$-$C_2$)alkoxy, amino, and (di)alkyl($C_1$-$C_2$)amino radicals; and
  phenyl radicals optionally substituted by at least one radical chosen from hydroxyl, amino, and ($C_1$-$C_2$) alkoxy radicals;
  $R'_2$ and $R'_3$ may form, together with the nitrogen atom to which they are attached, a saturated or unsaturated heterocycle, comprising 5 to 7 members, wherein the carbon atoms may be replaced by an oxygen or nitrogen atom, this heterocycle being optionally substituted by at least one radical chosen from halogen atoms, amino, (di)alkyl($C_1$-$C_4$)amino, hydroxyl, carboxyl, (di)alkylcarboxamido, ($C_1$-$C_2$)alkoxy, and $C_1$-$C_4$ alkyl radicals which are optionally substituted by at least one radical chosen from hydroxyl, amino, (di)alkylamino, alkoxy, carboxyl, and sulfonyl radicals; and when two radicals Y are carried by two adjacent carbon atoms, they may form, together with the carbon atoms to which they are attached, a saturated or unsaturated, aromatic or non-aromatic, cyclic or heterocyclic group comprising 5 to 6 members, optionally substituted by at least one $C_1$-$C_4$ alkyl radical;

Z is chosen from:
  linear and branched $C_1$-$C_4$ alkyl radicals;
  $NR_3R_4$ radicals; and
  $OR_5$ radicals;

$R_1$, $R_2$, $R_3$, $R_4$ and $R_5$, which are identical or different, are chosen from:
  $C_1$-$C_6$ alkyl radicals optionally substituted by at least one radical chosen from $OR_6$, $NR_7R_8$, carboxyl, $C_1$-$C_4$ alkyl carboxylate, sulfonic, (di)alkylcarboxamido $CONR_7R_8$, sulfonamido $SO_2NR_7R_8$ radicals; and 5- or 6-membered heteroaryl and phenyl radicals optionally substituted by at least one radical chosen from ($C_1$-$C_4$)alkyl, hydroxyl, $C_1$-$C_2$ alkoxy, amino, (di)alkyl($C_1$-$C_2$)amino and $C_1$-$C_4$ hydroxyalkyl radicals;
  phenyl radicals optionally substituted by at least one radical chosen from ($C_1$-$C_4$)alkyl, hydroxy($C_1$-$C_4$) alkyl, hydroxyl, $C_1$-$C_2$ alkoxy, amino, and (di)alkyl ($C_1$-$C_2$)amino radicals;
  5- or 6-membered heteroaryl radicals optionally substituted by at least one radical chosen from ($C_1$-$C_4$)alkyl radicals and ($C_1$-$C_2$)alkoxy radicals;

$R_3$, $R_4$ and $R_5$ may also be chosen from a hydrogen atom;

$R_6$, $R_7$ and $R_8$, which are identical or different, are chosen from a hydrogen atom; linear and branched $C_1$-$C_4$ alkyl radicals optionally substituted by at least one radical chosen from hydroxyl, $C_1$-$C_2$ alkoxy, (di)alkylcarboxamido $CONR_9R_{10}$, sulfonyl $SO_2R_9$, and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals; and phenyl radicals optionally substituted by at least one radical chosen from ($C_1$-$C_4$)alkyl, hydroxyl, $C_1$-$C_2$ alkoxy, amino, and (di)alkyl($C_1$-$C_2$)amino radicals;

$R_7$ and $R_8$, which are identical or different, are chosen from (di)alkylcarboxamido $CONR_9R_{10}$ radicals and sulfonyl $SO_2R_9$ radicals;

$R_9$ and $R_{10}$, which are identical or different, are chosen from a hydrogen atom, and linear and branched $C_1$-$C_4$ alkyl radicals optionally substituted by at least one radical chosen from a hydroxyl radical and $C_1$-$C_2$ alkoxy radicals;

$R_1$ and $R_2$, and independently $R_3$ and $R_4$, may form, together with the nitrogen atoms to which they are attached, a saturated or unsaturated heterocycle, comprising 5 to 7 members, wherein the carbon atoms may be replaced by an oxygen or nitrogen atom, said heterocycle being optionally substituted by at least one radical chosen from halogen atoms, amino, (di)alkyl($C_1$-$C_4$) amino, (di)hydroxyalkyl($C_1$-$C_4$)amino, hydroxyl, carboxyl, (di)alkylcarboxamido, ($C_1$-$C_2$)alkoxy, and $C_1$-$C_4$ alkyl radicals optionally substituted by at least one radical chosen from hydroxyl, amino, (di)alkyl($C_1$-$C_4$) amino, $C_1$-$C_2$ alkoxy, carboxyl, and sulfonyl radicals;

An- is an anion or a mixture of anions which allows the electroneutrality of the structures to be ensured;

with the exception of the following compounds:
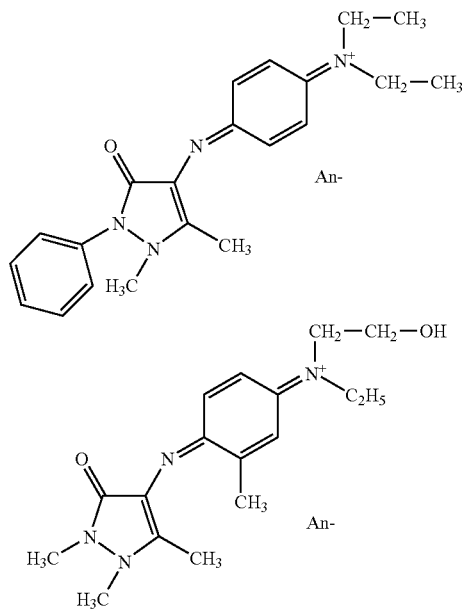
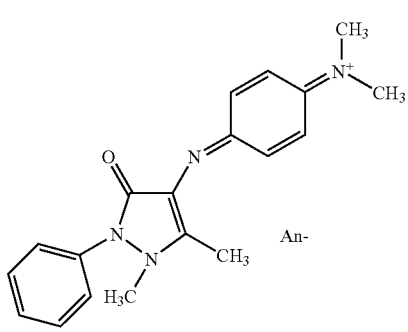
and also their mesomeric forms, their acid addition salts and their solvates thereof.
* * * * *

UNITED STATES PATENT AND TRADEMARK OFFICE
CERTIFICATE OF CORRECTION

PATENT NO. : 7,582,123 B2  
APPLICATION NO. : 12/213441  
DATED : September 1, 2009  
INVENTOR(S) : Aziz Fadli and Eric Metais It is certified that error appears in the above-identified patent and that said Letters Patent is hereby corrected as shown below:

On the title page, item (57), formula (I),

" 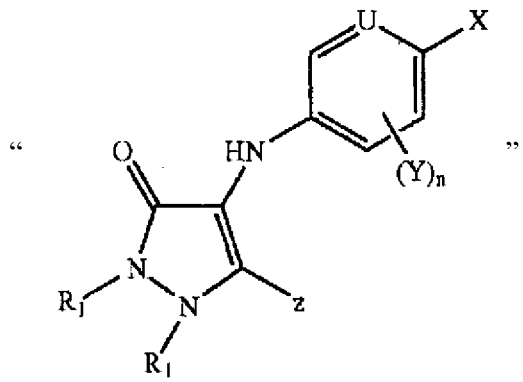 "

should read

-- 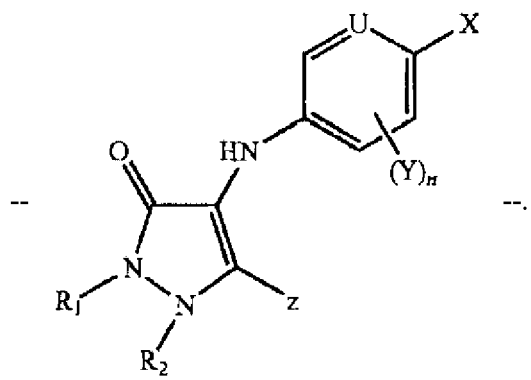 --.

UNITED STATES PATENT AND TRADEMARK OFFICE
CERTIFICATE OF CORRECTION

PATENT NO. : 7,582,123 B2  Page 2 of 5
APPLICATION NO. : 12/213441
DATED : September 1, 2009
INVENTOR(S) : Aziz Fadli and Eric Metais It is certified that error appears in the above-identified patent and that said Letters Patent is hereby corrected as shown below:

On the title page, item (57), formula (II),

"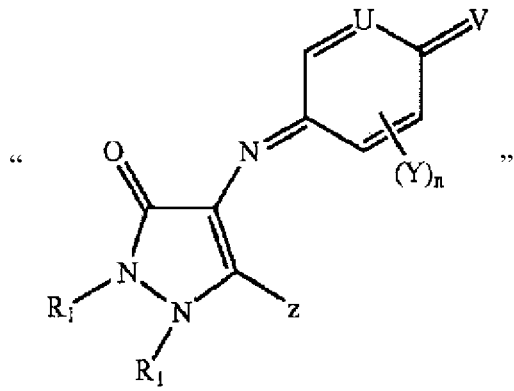"

should read

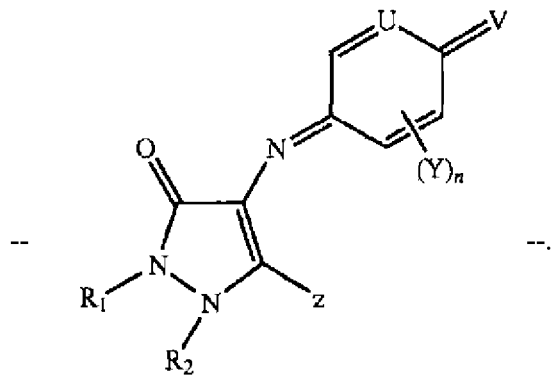

--     --.

UNITED STATES PATENT AND TRADEMARK OFFICE
CERTIFICATE OF CORRECTION

PATENT NO.       : 7,582,123 B2
APPLICATION NO.  : 12/213441
DATED            : September 1, 2009
INVENTOR(S)      : Aziz Fadli and Eric Metais It is certified that error appears in the above-identified patent and that said Letters Patent is hereby corrected as shown below:

In claim 1, column 135, line 41, "$NR'_1R''_2$" should read --$NR'_1R''_1$--.

In claim 1, column 136, line 13, "$N^+R'_1R''_1$ the" should read --$N^+R'_1R''_1$, the--.

In claim 1, column 136, line 44, "arechosen" should read --are chosen--.

In claim 2, column 138, line 63, "$NR'_1R''_1$ wherein" should read --$NR'_1R''_1$, wherein--.

In claim 2, column 139, line 37, "An- ," should read --An-,--.

In claim 2, column 139, line 65, "$NR'_2R''_3$;" should read --$NR'_2R'_3$;--.

In claim 10, column 142, line 3, "(di)hydroxy-alkyl($C_1$-$C_2$)amino," should read --(di)hydroxyalkyl($C_1$-$C_2$)amino,--.

In claim 11, column 142, line 15, "N-(2-hydroxyethyl)homopiper-azine," should read --N-(2-hydroxyethyl)homopiperazine,--.

In claim 15, column 142, line 31, "$NR'_1\ R''_1$" should read --$NR'_1R''_1$--.

In claim 16, column 142, line 42, "formula" should read --formulae--.

In claim 16, column 142, line 45, "$N+R'_1R''_1$" should read --$N^+R'_1R''_1$--.

In claim 19, column 144, line 42, "arechosen" should read --are chosen--.

UNITED STATES PATENT AND TRADEMARK OFFICE
CERTIFICATE OF CORRECTION

PATENT NO. : 7,582,123 B2 Page 4 of 5
APPLICATION NO. : 12/213441
DATED : September 1, 2009
INVENTOR(S) : Aziz Fadli and Eric Metais It is certified that error appears in the above-identified patent and that said Letters Patent is hereby corrected as shown below:

In claim 19, column 146, lines 4-14,

" 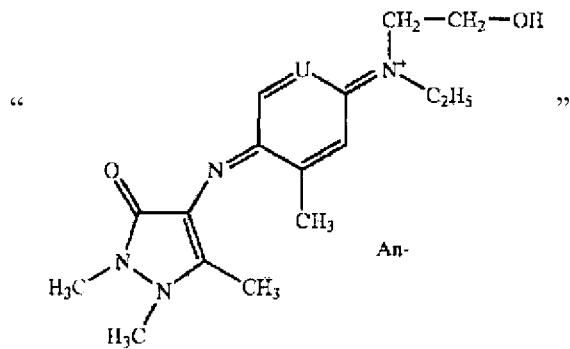 "   should read

-- 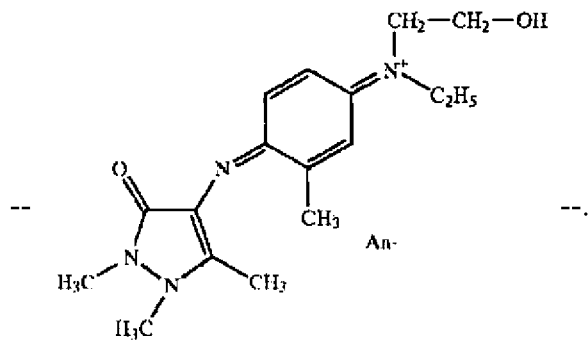 --.

UNITED STATES PATENT AND TRADEMARK OFFICE
CERTIFICATE OF CORRECTION

PATENT NO. : 7,582,123 B2
APPLICATION NO. : 12/213441
DATED : September 1, 2009
INVENTOR(S) : Aziz Fadli and Eric Metais It is certified that error appears in the above-identified patent and that said Letters Patent is hereby corrected as shown below:

In claim 20, column 147, line 33, "$N^+R'_1R''_1$ the" should read --$N^+R'_1R''_1$, the--.

In claim 20, column 147, line 63, "arechosen" should read --are chosen--.

In claim 22, column 151, line 13, "$N^+R'_1R''_1$ the" should read --$N^+R'_1R''_1$, the--.

In claim 22, column 151, line 44, "arechosen" should read --are chosen--.

Signed and Sealed this

Eighth Day of December, 2009

David J. Kappos
*Director of the United States Patent and Trademark Office*